(12) United States Patent
Biggadike et al.

(10) Patent No.: US 7,592,329 B2
(45) Date of Patent: *Sep. 22, 2009

(54) CRYSTALLINE COMPLEXES OF FLUTICASONE-2-FUROATE

(75) Inventors: Keith Biggadike, Stevenage (GB); Steven John Coote, Stevenage (GB); Andrew Craig, Tonbridge (GB); David Malcolm Crowe, Tonbridge (GB); Victor Witold Jacewicz, Tonbridge (GB); Michael John Millan, Tonbridge (GB); Rosalyn Kay Nice, Stevenage (GB); Brian Noga, Durham, NC (US); John Frederick Seager, Stevenage (GB); Andrew Lewis Theophilus, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 828 days.

This patent is subject to a terminal disclaimer.

(21) Appl. No.: 10/503,114

(22) PCT Filed: Feb. 4, 2003

(86) PCT No.: PCT/GB03/00478

§ 371 (c)(1), (2), (4) Date: Oct. 20, 2004

(87) PCT Pub. No.: WO03/066656

PCT Pub. Date: Aug. 14, 2003

(65) Prior Publication Data

US 2005/0043284 A1 Feb. 24, 2005

(51) Int. Cl.
*A61K 31/58* (2006.01)
*C07J 17/00* (2006.01)
(52) U.S. Cl. ............................. 514/172; 540/114
(58) Field of Classification Search ............ 514/180, 514/179, 171, 172; 424/46, 405
See application file for complete search history.

(56) References Cited

U.S. PATENT DOCUMENTS

| | | |
|---|---|---|
| 2,837,464 A | 6/1958 | Nobile |
| 3,067,197 A | 12/1962 | Agnello et al. |
| 3,312,590 A | 4/1967 | Elks et al. |
| 3,506,694 A | 4/1970 | Oxley |
| 3,557,162 A | 1/1971 | Voorschoten et al. |
| 3,639,434 A | 2/1972 | Oxley et al. |
| 3,755,302 A | 8/1973 | Ercoli et al. |
| 3,828,080 A | 8/1974 | May et al. |
| 3,856,828 A | 12/1974 | Phillipps et al. |
| 3,891,631 A | 6/1975 | Phillipps et al. |
| 3,981,894 A | 9/1976 | Phillipps et al. |
| 3,989,686 A | 11/1976 | Phillipps et al. |
| 4,093,721 A | 6/1978 | Phillipps et al. |
| 4,113,680 A | 9/1978 | Kamano et al. |
| 4,187,301 A | 2/1980 | Edwards |
| 4,188,385 A | 2/1980 | Edwards |
| 4,198,403 A | 4/1980 | Alvarez |
| 4,221,787 A | 9/1980 | Bodor et al. |
| 4,261,984 A | 4/1981 | Alvarez |
| 4,263,289 A | 4/1981 | Edwards |
| 4,267,173 A | 5/1981 | Draper |
| 4,285,937 A | 8/1981 | Kalvoda |
| 4,310,466 A | 1/1982 | Edwards |
| 4,335,121 A | 6/1982 | Phillipps et al. |
| 4,377,575 A | 3/1983 | Haddad et al. |
| 4,472,393 A | 9/1984 | Shapiro |
| 4,607,028 A | 8/1986 | Schmidlin |
| 4,710,495 A | 12/1987 | Bodor |
| 4,861,765 A | 8/1989 | Mitsukuchi et al. |
| 4,992,474 A | 2/1991 | Skidmore et al. |
| 4,994,439 A | 2/1991 | Longenecker et al. |
| 4,996,335 A | 2/1991 | Bodor |
| 5,063,222 A | 11/1991 | Komoto et al. |
| 5,081,113 A | 1/1992 | Claussner et al. |
| 5,202,316 A | 4/1993 | Claussner et al. |
| 5,362,721 A | 11/1994 | Stache et al. |
| 5,420,120 A | 5/1995 | Boltralik |
| 5,608,093 A | 3/1997 | Stache et al. |
| 5,658,549 A | 8/1997 | Akehurst et al. |
| 5,707,984 A | 1/1998 | Tjoeng et al. |
| 5,837,699 A | 11/1998 | Sequeira et al. |

(Continued)

FOREIGN PATENT DOCUMENTS

BE 889563 A 11/1981

(Continued)

OTHER PUBLICATIONS

Jeffrey,"Hydrate Inclusion Compounds." Journal of Inclusion Phenomena 1984:1;211-222.*

(Continued)

*Primary Examiner*—Frederick Krass
*Assistant Examiner*—Walter E Webb
(74) *Attorney, Agent, or Firm*—James P. Riek

(57) ABSTRACT

There is provided a crystalline complex comprising a compound of formula (I)

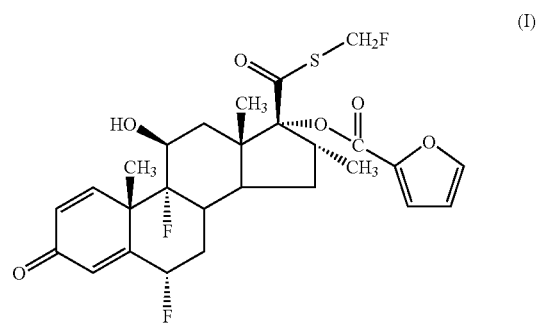

in which the crystal lattice is stabilized by the presence of a guest molecule, characterized in that the crystalline complex is of space group $P2_12_12_1$ having unit cell dimensions of about 12.5±1.0 §, 15±1.0 §, and 16.2±1.0 § when determined at either 120K or 150K.

10 Claims, 36 Drawing Sheets

U.S. PATENT DOCUMENTS

| | | |
|---|---|---|
| 5,849,265 A | 12/1998 | Li-Bovet et al. |
| 5,889,015 A | 3/1999 | Sequeira et al. |
| 5,972,920 A | 10/1999 | Seidel |
| 5,981,517 A | 11/1999 | Bodor |

| | | | | | | |
|---|---|---|---|---|---|---|
| 6,057,307 | A | 5/2000 | Sequeira et al. | WO | 0178745 | 10/2001 |
| 6,127,353 | A | 10/2000 | Yuen et al. | WO | 0200199 | 1/2002 |
| 6,136,294 | A | 10/2000 | Adjei et al. | WO | 0202565 | 1/2002 |
| 6,197,761 | B1 | 3/2001 | Biggadike et al. | WO | 0207767 | 1/2002 |
| 6,261,539 | B1 | 7/2001 | Adjei et al. | WO | 0208243 | 1/2002 |
| 6,395,300 | B1 | 5/2002 | Straub et al. | WO | WO 02/00679 | 1/2002 |
| 6,537,983 | B1 | 3/2003 | Biggadike et al. | WO | 0212266 | 2/2002 |
| 6,777,399 | B2 * | 8/2004 | Biggadike et al. ............ 514/172 | WO | 0213868 | 2/2002 |
| 6,921,757 | B2 | 7/2005 | Cuenoud et al. | WO | WO 02/12265 | 2/2002 |
| 7,244,742 | B2 | 7/2007 | Pieper et al. | WO | 0226723 | 4/2002 |
| 2002/0081266 | A1 | 6/2002 | Woolfe et al. | WO | 0236106 | 5/2002 |
| 2002/0103392 | A1 | 8/2002 | Stache et al. | WO | 0251422 | 7/2002 |
| 2002/0165211 | A1 | 11/2002 | Biggadike | WO | 0253186 | 7/2002 |
| 2002/0173496 | A1 | 11/2002 | Biggadike | WO | 0266422 | 8/2002 |
| 2002/0177581 | A1 | 11/2002 | Biggadike | WO | 0270490 | 9/2002 |
| 2003/0018019 | A1 | 3/2003 | Meade et al. | WO | 0276933 | 10/2002 |
| 2003/0073676 | A1 | 4/2003 | Biggadike et al. | WO | 0285296 | 10/2002 |
| 2003/0109511 | A1 | 6/2003 | Biggadike et al. | WO | 02088167 | 11/2002 |
| 2003/0144257 | A1 | 7/2003 | Biggadike et al. | WO | 0210879 | 12/2002 |
| 2003/0158163 | A1 | 8/2003 | Cuenoud et al. | WO | 0300241 | 1/2003 |
| 2004/0053904 | A1 | 3/2004 | Komoto et al. | WO | 0313427 | 2/2003 |
| 2005/0163724 | A1 | 7/2005 | Miyadai et al. | WO | 0333000 | 4/2003 |
| | | | | WO | 0335668 | 5/2003 |

FOREIGN PATENT DOCUMENTS

| | | | | | |
|---|---|---|---|---|---|
| DE | 1059906 | 6/1959 | WO | 0340691 | 5/2003 |
| EP | 0004773 | 10/1979 | WO | 0342229 | 5/2003 |
| EP | 0057401 | 8/1982 | WO | 0342230 | 5/2003 |
| EP | 0179583 | 4/1986 | WO | 0348181 | 6/2003 |
| EP | 0393658 | 10/1990 | WO | 0362259 | 7/2003 |
| EP | 0416951 | 3/1991 | WO | 0364445 | 8/2003 |
| GB | 1191965 | 5/1970 | WO | 0366656 | 8/2003 |
| GB | 1296458 | 11/1972 | WO | 0372592 | 9/2003 |
| GB | 1384372 | 2/1975 | WO | 0386399 | 10/2003 |
| GB | 1438940 | 6/1976 | WO | 2004013156 | 2/2004 |
| GB | 1517278 | 7/1978 | ZA | 872389 | 4/1987 |
| GB | 2079755 | 1/1982 | | | |
| GB | 2088877 | 6/1982 | | | |
| GB | 2140800 | 12/1984 | | | |
| IL | 109656 | 2/1998 | | | |
| JP | 04208267 | 7/1992 | | | |
| JP | 8291072 | 11/1996 | | | |
| JP | 8291073 | 11/1996 | | | |
| WO | 8903390 | 4/1989 | | | |
| WO | 9015816 | 12/1990 | | | |
| WO | 9104252 | 4/1991 | | | |
| WO | 9214472 | 9/1992 | | | |
| WO | 9531964 | 11/1995 | | | |
| WO | 9619199 | 6/1996 | | | |
| WO | 9705136 | 2/1997 | | | |
| WO | 9715298 | 5/1997 | | | |
| WO | 9721721 | 6/1997 | | | |
| WO | 9721724 | 6/1997 | | | |
| WO | 9724365 | 7/1997 | | | |
| WO | 9740836 | 11/1997 | | | |
| WO | 9746243 | 12/1997 | | | |
| WO | 9817676 | 4/1998 | | | |
| WO | 9834596 | 8/1998 | | | |
| WO | 9901467 | 1/1999 | | | |
| WO | 9925359 | 5/1999 | | | |
| WO | 9932089 | 7/1999 | | | |
| WO | 0016814 | 3/2000 | | | |
| WO | 0033892 | 6/2000 | | | |
| WO | 0038811 | 7/2000 | | | |
| WO | 0049993 | 8/2000 | | | |
| WO | 0066522 | 11/2000 | | | |
| WO | 0120331 | 3/2001 | | | |
| WO | 0154481 | 8/2001 | | | |
| WO | 0154664 | 8/2001 | | | |
| WO | 0162722 | 8/2001 | | | |
| WO | 0178736 | 10/2001 | | | |
| WO | 0178739 | 10/2001 | | | |
| WO | 0178741 | 10/2001 | | | |

OTHER PUBLICATIONS

Phillips, GH et al., "Synthesis and structure activity Relationships in a series of Anti-inflammatory Corticosteroid Analogues, Halomethyl Androstane—17B-carbothioates and—17B-carboselenoates," *Journal of Medicinal Chemistry* 37(22):3717-3729 (Oct. 1994).

Aigbirhio et al.; "Automated Radiosynthesis of No-carrier-added [S-fluoromethyl-18F]Fluticasone Propionate as a Radiotracer for Lung Deposition Studies with PET"; J. Label. Compds. Radiopharm.; 1997; vol. 39, No. 7; pp. 569-584.

Barnes; "Chronic Obstructive Pulmonary Disease: new opportunities for drug development"; Trends in Pharmacological Sciences; 1998; vol. 19, No. 10; pp. 415-423.

Barnes; "Efficacy of Inhaled Corticosteroids in Asthma"; The Journal of Allergy and Clinical Immunology; 1998; vol. 102, No. 4; pp. 531-538.

Barnes; "Novel approaches and targets for treatment of Chronic Obstructive Pulmonary Disease"; Am. J. Respir. Crit. Care Med.; 1999; vol. 160; pp. S72-S79.

Baumgarten et al.; "Initial Treatment of Symptomatic Mild to Moderate Bronchial Asthma with the Salmeterol/Fluticasone Propionate (50/250μg) Combination Product (SAS 40023)"; European Journal of Medical Research; 2002; vol. 7; pp. 1-7.

Bowler; "Long Acting Beta Agonists"; Australian Family Physician; 1998; vol. 27, No. 12; pp. 1114-1118.

Busse et al.; "Steroid-sparing effects of fluticasone propionate 100 μg and salmeterol 50 μg. administered twice daily in a single product in patients previously controlled with fluticasone propionate 250 μg administered twice daily"; J. Allergy Clin. Immunol.; 2003; vol. 111, No. 1; pp. 57-65.

CAS Registry No. 102113-40-6; 2004.

CAS Registry No. 90566-53-3 "Fluticasone"; 1984.

Chapman et al.; "Anti-Inflammatory Activity of Inhaled Mometasone Furoate in Allergic Mice"; Arzneimettelforschung/Drug Res.; 1998; vol. 48, No. 4; pp. 384-391.

Definition of "Fluticasone"; Dictionary of Organic Compounds, 6th ed.; 1996; vol. 1; p. 3234.

Fowler et al.; "Step-down therapy with low-dose fluticasone-salmeterol combination or medium-dose hydrofluoroalkane 134a-beclomethasone alone"; J. Allergy Clin. Immunol.; 2002; vol. 109, No. 6; pp. 929-935.

Garner et al.; "A validation study comparing accelerator MS and liquid scintillation counting for analysis of 14C-labelled drugs in plasma, urine and faecal extracts"; J. Pharm. Biomed. Anal.; 2000; vol. 24; pp. 197-209.

Johansson et al.; "Comparison of Salmeterol/Fluticasone Propionate Combination with Budesonide in Patients with Mild-to-Moderate Asthma"; Clin. Drug Invest.; 2001; vol. 21, No. 9; pp. 633-642.

Juniper et al.; "Impact of Inhaled Salmeterol/Fluticasone Propionate Combination Product versus Budesonide on the Health-Related Quality of Life of Patients with Asthma"; Am. J. Respir. Med.; 2002; vol. 1, No. 6; pp. 435-440.

Kenley et al.; "An Automated, Column-Switching HPLC Method for Analyzing Active and Excipient Materials in Both Cream and Ointment Formulations"; Drug Development and Industrial Pharmacy; 1985; vol. 11 (9 &10); pp. 1781-1796.

Kertesz et al.; "Thiol Esters from Steroid 17-beta-Carboxylic Acids: Carboxylate Activation and Internal Participation by 17-alpha-Acylates"; J. Org. Chem.; 1986; vol. 51; pp. 2315-2328.

Knobil et al.; "Adding Salmeterol Is More Effective Than Increasing the Dose of Fluticasone for Patients with Asthma Who Are Symptomatic on Low Dose Fluticasone"; European Respiratory Review; 1998; vol. 12, No. Suppl 29; pp. 19S-20S.

Kooreman et al.; "The synthesis of 17-esters of corticosteroids protection of 11-beta-hydroxyl of the trimethylsilyl group"; Synthetic Communications; 1971; vol. 1, No. 2; pp. 81-87.

Lane et al.; "Evaluation of a New Capillary Electrochromatography/Mass Spectrometry Interface Using Short Columns and High Field Strengths for Rapid and Efficient Analyses"; Rapid Communications in Mass Spectrometry; 1996; vol. 10; pp. 733-736.

Lewis et al.; "Association of specific allergen sensitization with socioeconomic factors and allergic disease in a population of Boston women"; J. Allergy Clin. Immunol.; 2001; vol. 107, No. 4; pp. 615-622.

Li et al.; "Synthesis of aryl 5-(2-chlorophenyl)-2-furoates under phase transfer catalysis"; Synthetic Communications; 2002; vol. 32, No. 20; pp. 3081-3086.

Lumry; "A review of the preclinical and clinical data of newer intranasal steroids used in the treatment of allergic rhinitis"; J. Allergy Clin. Immunol; 1999; vol. 104, No. 4, Pt. 1; pp. S150-S158.

Lutsky et al.; "A Novel Class of Potent Topical Anti-inflammatory Agents: 17-Benzolylated, 7a-Halogeno Substituted Corticosteroids"; Arzneimettelforschung/Drug Res.; 1978; vol. 29, No. 11; pp. 1662-1667.

Lyseng-Williamson et al.; "Inhaled Salmeterol/Fluticasone Propionate Combination in Chronic Obstructive Pulmonary Disease"; Am. J. Respir. Med.; 2002; vol. 1, No. 4; pp. 273-282.

Mahoney et al.; "Drug effects on the neovascularization response to silver nitrate cauterization of the rat cornea"; Current Eye Research; 1985; vol. 4, No. 5; pp. 531-535.

Millard et al.; "Solubilization by cosolvents establishing useful constants for the log-linear model"; Int'l Journal of Pharmaceutics; 2002; vol. 245; pp. 153-166.

Mistry et al.; "Characterisation of impurities in bulk drug batches of fluticasone propionate using directly coupled HPLC-NMR spectroscopy and HPLC-MS"; J. Pharm. Biomed. Anal.; 1997; vol. 16; pp. 697-705.

Mistry et al.; "Impurity Profiling in Bulk Pharmaceutical Batches Using 19F NMR Spectroscopy and Distinction between Monomeric and Dimeric Impurities by NMR-based Diffusion Measurements"; J. Pharm. Biomed. Anal.; 1999; vol. 19; pp. 511-517.

Mitsutaka et al.; "Binding Affinities of Mometasone Furoate and Related Compounds Including Its Metabolites for the Glucocorticoid Receptor of Rat Skin Tissue"; J. Steroid Biochem. Mol. Biol.; 1993; vol. 44; pp. 141-145.

Mollmann et al.; "Chapter 14: Pharmacokinetic-Pharmacodynamic Correlations of Corticosteroids"; Handbook of Pharmacokinetic/Pharmacodynamic Correlation; 1995; pp. 323-336.

Moreno-Vargas et al.; "Synthesis and glycosidase inhibitory activities of 5-(1,4-dideoxy-1,4-imino-D- erythrosyl)-2-methyl-3-furoic acid (=5-[(3S,4R)-3,4-dihydroxypyrrolidin-2-yl]-2methylfuran-3-carboxylic acid) derivatives: New leads as selective -L-fucosidase and beta-galactosidase inhibitors"; Helvetica Chimica Acta; 2003; vol. 86; pp. 1894-1913.

Naedle-Risha et al.; "Dual components of optimal asthma therapy: scientific and clinical rationale for the use of long acting beta-agonists with inhaled corticosteroids"; The Journal of the American Osteopathic Association; 2001; vol. 101, No. 9; pp. 2001-2009.

Nelson et al.; "Fluticasone propionate/salmeterol combination provides more effective asthma control than low-dose inhaled corticosteroid plus montelukast"; J. Allergy Clin. Immunol.; 2000; vol. 106, No. 6; pp. 1088-1095.

O'Conner; "Combination Therapy"; Pulmonary Pharmacology and Therapeutics; 1998; vol. 11, No. 5/6; pp. 397-399.

Ong et al.; "Intrinsic Potencies of Novel Thiol Ester Corticosteroids RS-85095 and RS-21314 as Compared with Clobetasol 17-Propionate and Fluocinonide"; Arch. Dermatol.; 1989; vol. 125; pp. 1662-1665.

Ong et al.; "Micellar Solubilization of Timobesone Acetate in Aqueous and Aqueous Propylene Glycol Solutions of Nonionic Surfactants"; Pharmaceutical Research; 1988; vol. 5, No. 11; pp. 704-708.

Onrust et al.; "Mometasone Furoate: A Review of its Intranasal Use in Allergic Rhinitis"; Drugs; 1998; vol. 56, No. 4; pp. 725-745.

PCT/GB01/03495—International Preliminary Examination Report mailed Aug. 30, 2002.

PCT/GB01/03495—Written Opinion mailed Apr. 4, 2002.

Pettersson et al.; "Re-evaluation of the classical Mycoplasma lipophilum cluster (Weisburg et al. 1989) and description of two new clusters in the hominis group based on 16S rDNA sequences"; Int'l Journal of Systematic & Evolutionary Microbiology; 2001; vol. 51; pp. 633-643.

Popper et al.; "Structure-Activity Relationship of a Series of Novel Topical Corticosteroids"; J. Steroid Biochem.; 1987; vol. 27; pp. 837-841.

Sakagami et al.; "Mucoadhesive BDP microspheres for powder inhalation-their unique pharmacokinetic- pharmacodynamic profiles"; Respiratory Drug Delivery VI; 1998; pp. 193-199.

Sandham et al.; "Synthesis and Biological Properties of Novel Glucocorticoid Androstene C-17 Furoate Esters"; Bioorg. Med. Chem.; 2004; vol. 12; pp. 5213-5224.

Shapiro et al.; "17-esters and 17,21-diesters of 9a, 11B-dichlorocorticoids. Synthesis and anti-inflammatory activity"; Steroids; 1967; vol. 9, No. 2; pp. 143-156.

Shapiro et al.; "17 Heteroaroyl Esters of Corticosteroids 2. 11Beta Hydroxy Series"; J. Med. Chem.; 1987; vol. 30, No. 9; pp. 1581-1588.

Shapiro et al.; "Synthesis and structure activity studies of corticosteriod 17-heterocyclic aromatic esters. 1. 9a, 11B dichloro series"; J. Med. Chem.; 1987; vol. 30, No. 6; pp. 1068-1073.

Smith et al.; "In vitro Glucocorticoid Receptor Binding and Transcriptional Activation by Topically Active Glucocorticoids"; Arzneimettelforschung/Drug Res.; 1998; vol. 48, No. 4; pp. 956-960.

Smith et al.; "Comparison of the electroosmotic flow profiles and selectivity of stationary phases used in capillary electrochromatography"; Journal of Chromatography A.; 1999; vol. 832; pp. 44-54.

Szefler et al.; "Chapter 21, Glucocorticoids in Severe Asthma: Mechanisms of Action and Route of Administration"; Difficult Asthma; 1999; pp. 371-375.

Tanaka et al.; "Synthesis of 4H-furo[3,2-b]indole derivatives. III (1). Preparation of 4H-furo[3,2-b]indole-2-carboxylic acid derivatives"; J. Heterocyclic Chem.; 1979; vol. 16; pp. 785-788.

Togashi et al.; "9-fluoro-11B, 17, 21-trihyrdroxy-16a-methyl-1,4-pregnadiene-3, 20-dione 21- cyclohexanecarboxylate 17-cyclopropanecarboxylate (ST126)"; Oyo Yakuri; 2002; vol. 63, No. 5/6; pp. 61-77.

Ueno et al.; "Synthesis and Evaluation of Antiinflammatory Activities of a Series of Corticosteroid 17. Alpha—Esters Containing a Functional Group"; J. Med. Chem.; 1991; vol. 34, No. 8; pp. 2468-2473.

Van der Molen et al.; "Effects of the Long Acting Beta Agonist Formoterol on Asthma Control in Asthmatic Patients Using Inhaled Corticosteroids"; Thorax; 1996; vol. 52, No. 6; pp. 535-539.

Wenkert et al.; "Short syntheses of furan and catechol derivatives. A synthesis of hydrourushiol1,2"; J. Am. Chem. Soc.; 1983; vol. 105; pp. 2021-2029.

Woodford et al.; "Activity and bioavailability of a new steroid (Timobesone acetate) in cream and ointment compared with Lidex and Dermovate creams and ointments and Betnovate cream"; Int'l Journal of Pharmaceutics; 1985; vol. 26; pp. 145-155.

"Pharmacokinetics of GW685698X and CC118781 (Fluticasone Propionate) when Co-Administered by the Intratracheal or Intravenous Route to the Anaesthetised White Pig"; Study No. 03DMW062.

"Physical Tests: No. 941 X-Ray Diffraction"; the United States Pharmacopoeia, 23rd ed.; 1995; pp. 1843-1844.

"The Pharmacokinetics of GW685698X and CC118781 Following Intratracheal Co-Administration to the Anaesthetised White Pig"; Study No. B30947.

* cited by examiner

CRYSTALLINE COMPLEXES OF FLUTICASONE-2-FUROATE

This application is filed pursuant to 35 USC 371 as a U.S. National Phase Application of International Patent Application Ser. No. PCT/GB03/00478 filed on 4 Feb. 2003, which claims priority from U.S. patent application Ser. No. 10/067,010, now allowed, filed on 4 Feb. 2002.

The present invention relates to a novel crystalline complex containing an anti-inflammatory and anti-allergic compound of the androstane series and to processes for its preparation. The present invention also relates to pharmaceutical formulations containing the complex and to therapeutic uses thereof, particularly for the treatment of inflammatory and allergic conditions.

Glucocorticoids which have anti-inflammatory properties are known and are widely used for the treatment of inflammatory disorders or diseases such as asthma and rhinitis. For example, U.S. Pat. No. 4,335,121 discloses 6α,9α-Difluoro-17α-(1-oxopropoxy)-11β-hydroxy-16α-methyl-3-oxo-androsta-1,4-diene-17β-carbothioic acid S-fluoromethyl ester (known by the generic name of fluticasone propionate) and derivatives thereof. The use of glucocorticoids generally, and especially in children, has been limited in some quarters by concerns over potential side effects. The side effects that are feared with glucocorticoids include suppression of the Hypothalamic-Pituitary-Adrenal (HPA) axis, effects on bone growth in children and on bone density in the elderly, ocular complications (cataract formation and glaucoma) and skin atrophy. Certain glucocorticoid compounds also have complex paths of metabolism wherein the production of active metabolites may make the pharmacodynamics and pharmacokinetics of such compounds difficult to understand. Whilst the modem steroids are very much safer than those originally introduced, it remains an object of research to produce new molecules which have excellent anti-inflammatory properties, with predictable pharmacokinetic and pharmacodynamic properties, with an attractive side effect profile, and with a convenient treatment regime.

In our application PCT.GB.01.03495 we have identified a novel glucocorticoid compound which substantially meets these objectives.

We have now identified a novel crystalline complex of the novel glucocorticoid compound.

Thus, according to a first aspect of the invention, there is provided a crystalline complex comprising a compound of formula (I)

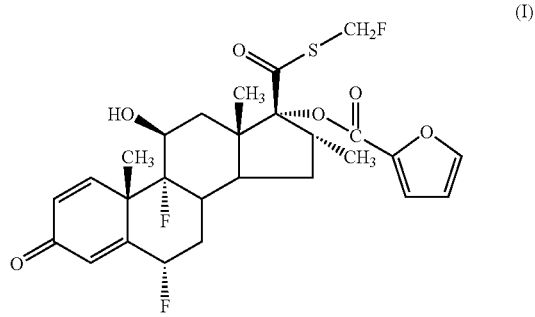

(I)

in which the crystal lattice is stabilised by the presence of a guest molecule, characterised in that the crystalline complex is of space group $P2_12_12_1$ having unit cell dimensions of about 12.5±1.0 Å, 15±1.0 Å, and 16.2±1.0 Å when determined at either 120K or 150K (hereinafter "a complex of the invention")

The nature of the crystal lattice can be seen by reference to FIG. 1 which shows the spacial arrangement of 4 molecules of steroid and 4 guests within a single unit cell for two example complexes and FIG. 2A and FIG. 2B which shows detail of the spacial arrangment between steroid and guest molecule for the same two example complexes.

We have determined the X-ray powder diffraction (XRPD) profiles for a large number of complexes according to the invention. These XRPD profiles are also apparently characteristic of the crystalline complexes according to the invention. In particular they exhibit one or more of the following 5 features when determined at ambient temperature (eg around 295K):

(a) A peak in the range of around 7.8-8.2; and
(b) A peak in the range of around 8.8-9.6; and
(c) A peak in the range of around 10.5-11.1
(d) A peak in the range of around 15.0-15.9
e) A peak, often (but not always) associated with a pair of peaks, in the range of around 21.2-21.8

Typically they exhibit 2 or more typically 3 or more of the above 5 features, especially 4 and particularly all 5 of the above 5 features.

The XRPD profiles of complexes of the invention when crystallographically pure also preferably exhibit one or more of the following 2 features when determined at ambient temperature (eg around 295K):

(a) Absence of a peak at around 7 (eg around 6.8-7.4) which is associated with the profile of unsolvated Form 1, 2 and 3 polymorphs and present at particularly high intensity in Forms 2 and 3;

(b) Absence of a peak at around 11.5 (eg around 11.3-11.7) which is associated with the profile of unsolvated Form 1 polymorph (all figures are in degrees 2 Theta).
Preferably both features are exhibited.

The chemical name of the compound of formula (I) is 6α,9α-Difluoro-17α-[(2-furanylcarbonyl)oxy]-11β-hydroxy-16α-methyl-3-oxo-androsta-1,4-diene-17β-carbothioic acid S-fluoromethyl ester.

The compound of formula (I) and compositions thereof have potentially beneficial anti-inflammatory or anti-allergic effects, particularly upon topical administration, demonstrated by, for example, its ability to bind to the glucocorticoid receptor and to illicit a response via that receptor, with long acting effect. Hence, the compound of formula (I) and compositions thereof is useful in the treatment of inflammatory and/or allergic disorders, especially in once-per-day therapy.

Space group $P2_12_12_1$ is characterised by angles of 90° being present in each of the 3 axes.

We have discovered that the compound of formula (I) can form a crystalline complex of characteristic space group, unit cell dimensions and crystalline structure as evidenced by X-ray diffraction with a very wide range of guest molecules.

The guest molecule preferably has a relative molecular weight in the range 16 to 150, more preferably 16 to 100, especially 40 to 100. Preferably the guest molecule is a liquid at ambient temperature and pressure (eg 295K, $1.013 \times 10^5$ Pa). However guest molecules which are a liquid under pressure may also be capable of acting as a guest molecule (especially under pressurised conditions). Substances which are solids at ambient temperature and pressure are also included.

The guest molecule preferably contains a moiety capable of acting as a hydrogen bond acceptor. Examples of moieties capable of acting as a hydrogen bond acceptor include carbonyl, sulphoxide, ether, —OH and amine groups (whether primary, secondary or tertiary amine groups) which moieties may form part of a carboxylic acid, ester or amide group. Moieties thioether and —SH may also be contemplated but are less preferred. Crystallographic studies have shown that a hydrogen bond acceptor on the guest is capable of interacting with the hydrogen atom of the C11 hydroxy on the compound of formula (I) thereby assisting the stabilisation of the crystal lattice (see in particular FIG. 2A and FIG. 2B). It is not ruled out that in some cases a hydrogen bond donor on the guest (eg the hydrogen atom of an —OH moiety) may be capable of interacting with the hydrogen bond acceptor on the compound of formula (I) thereby assisting the stabilisation of the crystal lattice.

Examples of suitable guest molecules include solvents e.g.:

amide moiety containing substances such as: dimethyl acetamide, dimethyl formamide, N-methyl-2-pyrrolidinone;

amine moiety containing substances such as: cyclohexylamine, t-butylamine;

carbonyl moiety containing substances such as: acetone, methylethylketone, cyclopentanone, cyclohexanone;

sulphoxides such as dimethylsulphoxide;

alcohols such as: ethanol, butan-1-ol, propan-1-ol, propan-2-ol;

ethers such as: 1,4-dioxane, tetrahydrofuran;

esters such as: ethylformate, methylacetate;

carboxylic acids such as: acetic acid;

heterocycles such as: pyridine;

water.

An example of a solid guest molecule is ε-caprolactam.

Preferred guest molecules are pharmaceutically acceptable substances and, as described below, complexes of the invention containing them may be used in therapy. However even if the guest molecule is not pharmaceutically acceptable then such complexes may be useful in the preparation of other complexes containing compound of formula (I), for example, other complexes of the invention containing guest molecules that are pharmaceutically acceptable or compound of formula (I) in unsolvated form.

In one sub-aspect of the invention, the complex is not an essentially stoichiometric complex containing as guest molecule one of the following: acetone, dimethylformamide, dimethylacetamide, tetrahydrofuran, N-methyl-2-pyrrolidinone, propan-2-ol (isopropanol) or methylethylketone, more particularly the complex is not a complex containing as guest molecule one of the aforementioned substances having stoichiometry of compound of formula (I) to solvent of 0.95:1 to 1.05:1.

In another sub-aspect of the invention, the complex is not a complex containing as guest molecule ethanol, water or methyl acetate, more particularly the complex is not an essentially stoichiometric complex containing as guest molecule one of the aforementioned substances, especially a complex having stoichiometry of compound of formula (I) to solvent of 0.95:1 to 1.05:1.

In some preferred embodiments, guest molecules include: cyclopentanone, cyclohexanone, cyclohexylamine, t-butylamine, dimethylsulfoxide, ethanol, propan-1-ol, butan-1-ol, 1,4-dioxane, ethyl formate, methyl acetate, pyridine, water and acetic acid, particularly cyclopentanone, dimethylsulfoxide, propan-1-ol, 1,4-dioxane, ethyl formate, butan-1-ol and acetic acid.

In other preferred embodiments of the invention, the guest molecule is propan-2-ol or acetone, more preferably propan-2-ol.

The stoichiometry of the complex will usually be such that the ratio of compound to formula (I) to guest molecule, in molar terms, is 1:2.0 to 1:0.3, more preferably 1:1.6 to 1:0.6, especially 1:1.2 to 1:0.8.

Unusually the complex of the invention has a crystal structure which is quite distinct from that of compound of formula (I) in the absence of a guest molecule, eg. the compound of formula (I) as unsolvated polymorph Form 1 which has a space group of P2$_1$ (i.e. two of the axis angles are 90°) and cell dimensions of 7.6, 14.1, 11.8 Å when determined at 150K. Thus if the guest molecule is removed below a threshold level (which will differ from guest to guest) for example by heating (optionally at reduced pressure eg under vacuum) then the crystal structure of the complex starts to break down and converts to that of the structure of an unsolvated compound of formula (I), typically unsolvated polymorph Form 1.

FIG. 3 shows the evolution of the XRPD profile of the complex with acetone when subjected to heating, and its in conversion to unsolvated polymorph Form 1.

The complexes with acetone, dimethylformamide, tetrahydrofuran, N-methyl-2-pyrrolidinone and acetic acid, at least, are particularly stable when subjected to heating, requiring a temperature in excess of 95° C. to cause substantial loss of guest from the crystal lattice. Of these, the complexes with acetone, dimethylformamide and acetic acid required a temperature in excess of 125° C. to cause substantial loss of guest.

Preferably the unit cell dimensions are about 12.5±1.0 Å, 15±1.0 Å, and 16.2±1.0 Å when determined at 120K. More preferably the unit cell dimensions are about 12.1±0.6 Å, 14.9±0.7 Å and 16.2±1.0 Å when determined at either 120K or 150K. Usually the unit cell dimensions are about 12.1±0.4 Å, 14.9±0.6 Å, and 16.2±0.7 Å when determined at either 120K or 150K, especially when determined at 120K.

Table 1 shows the unit cell dimensions and peak positions for a number of example complexes:

TABLE 1

| Guest molecule | Unit cell dimensions | | | Peak positions | | | | |
| --- | --- | --- | --- | --- | --- | --- | --- | --- |
| Ethanol[A] | 12.2 | 15.2 | 15.5 | 8.2 | 9.3 | 10.9 | 15.4 | 21.8 |
| Propan-1-ol[A] | 12.4 | 15.4 | 15.5 | 8.1 | 9.1 | 10.8 | 15.3 | 21.6 |
| Propan-2-ol[A] | 12.3 | 15.1 | 15.7 | 8.1 | 9.2 | 10.8 | 15.3 | 21.6 |
| 1,4-Dioxane[A] | 12.5 | 14.6 | 16.1 | 8.2 | 9.3 | 10.8 | 15.1 | 21.6 |
| Ethyl formate[A] | 12.0 | 14.7 | 16.2 | 8.0 | 9.4 | 10.9 | 15.6 | 21.8 |
| Acetic Acid[A] | 11.9 | 14.5 | 16.1 | 8.2 | 9.5 | 11.0 | 15.7 | 21.7 |
| Acetone[A] | 11.9 | 14.7 | 16.2 | 8.1* | 9.5 | 10.9 | 15.7 | 21.6 |
| Dimethyl-formamide[A] | 12.1 | 14.8 | 16.2 | 7.9 | 9.1 | 10.8 | 15.5 | 21.5 |
| Dimethyl-acetamide[A] | 12.2 | 14.9 | 16.6 | 8.0 | 9.4 | 10.8 | 15.4 | 21.6 |
| Methyl-ethylketone[A] | 12.0 | 14.9 | 16.3 | 8.0 | 9.3 | 10.8 | 15.5 | 21.5 |
| Tetrahydrofuran[A] | 12.0 | 14.6 | 16.4 | 8.1 | 9.5 | 10.9 | 15.5 | 21.5 |
| N-Methyl-2-pyrrolidinone[B] | 12.0 | 14.9 | 16.8 | 7.9 | 9.4 | 10.8 | 15.5 | 21.6 |
| N-Methyl-2-pyrrolidinone[D] | 12.1 | 14.9 | 16.9 | | | | | |
| Dimethyl-sulphoxide | N/a | N/a | N/a | 8.1* | 9.4 | 10.9 | 15.4 | 21.5 |
| Cyclopentanone | N/a | N/a | N/a | 8.1 | 9.4 | 10.9 | 15.5 | 21.5 |
| Cyclohexanone[A] | 12.6 | 14.7 | 16.4 | | | | | |
| Water | N/a | N/a | N/a | 8.1* | 9.6 | 11.0 | 15.5 | 21.8 |
| Butan-1-ol[A] | 12.5 | 15.7 | 15.4 | 8.0 | 8.9 | 10.6 | 15.1 | 21.6 |
| Methyl Acetate[C] | 12.1 | 14.6 | 16.3 | 8.1 | 9.4 | 10.8 | 15.5 | 21.8 |
| Pyridine[A] | 12.1 | 14.9 | 16.2 | | | | | |
| Cyclohexyl-amine[A] | 13.4 | 15.2 | 15.5 | | | | | |
| t-Butylamine[A] | 12.7 | 15.0 | 15.9 | 8.1 | 9.0 | 10.5 | 15.9 | 21.5 |
| ε-caprolactam | N/a | N/a | N/a | 8.1* | 9.0 | 10.5 | 15.1 | 21.4 |

Superscripts refer to X-ray diffraction pattern collection conditions set out in the Examples section TABLE 1-continued

| Guest molecule | Unit cell dimensions | Peak positions |
|---|---|---|

N/a indicates data not available
*peak may not always be observed due to orientation effects Compound (I) undergoes highly efficient hepatic metabolism to yield the 17-β carboxylic acid (X) as the sole major metabolite in rat and human in vitro systems. This metabolite has been synthesised and demonstrated to be >1000 fold less active than the parent compound in in vitro functional glucocorticoid assays.

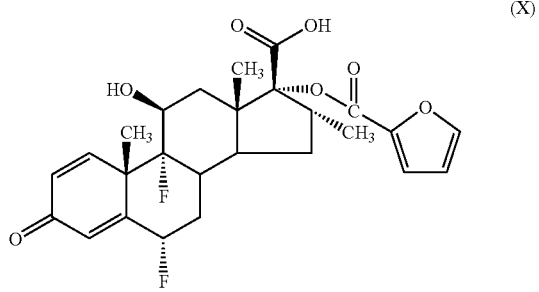

This efficient hepatic metabolism is reflected by in vivo data in the rat, which have demonstrated plasma clearance at a rate approaching hepatic blood flow and an oral bioavailability of <1%, consistent with extensive first-pass metabolism.

In vitro metabolism studies in human hepatocytes have demonstrated that compound (I) is metabolised in an identical manner to fluticasone propionate but that conversion of (I) to the inactive acid metabolite occurs approximately 5-fold more rapidly than with fluticasone propionate. This very efficient hepatic inactivation would be expected to minimise systemic exposure in man leading to an improved safety profile.

Inhaled steroids are also absorbed through the lung and this route of absorption makes a significant contribution to systemic exposure. Reduced lung absorption could therefore provide an improved safety profile. Studies with compound (I) have shown significantly lower exposure to compound (I) than with fluticasone propionate after dry powder delivery to the lungs of anaesthetised pigs.

An improved safety profile is believed to allow the compound of formula (I) to demonstrate the desired anti-inflammatory effects when administered once-per day. Once-per-day dosing is considered to be significantly more convenient to patients than the twice-per day dosing regime that is normally employed for fluticasone propionate.

We have also surprisingly found that the compound of Formula (I) shows a significantly longer mean absorption time (MAT) than fluticasone propionate, in man.

Measurements have shown that the compound of Formula (I) has a mean absorption time of an average of 12 hours while fluticasone propionate has a MAT of an average of 2.1 hours. Mathematical deconvolution of the plasma concentration time data shows that the time taken for 90% of lung dose to be absorbed is on average, 21 hours for compounds of Formula (I) compared with 11 hours for fluticasone propionate. It has been shown that oral bioavailability of the compound of Formula (I) is very low, and therefore systemic exposure is predominantly the result of absorption from the lung. This would suggest that the compound of Formula (I) has a significantly longer residence time in the lung than fluticasone propionate.

A longer residence time in the lung may lead to a longer duration of action and the lower daily systemic exposure may lead to an improved safety profile which, it is believed, allows the compound of formula (I) to demonstrate the desired anti-inflammatory effects when administered once-per day. Once-per-day dosing is considered to be significantly more convenient to patients than the twice-per day dosing regime that is normally employed for fluticasone propionate.

In vitro human lung tissue affinity experiments indicate significantly higher affinity of the compound of formula (I) for human lung tissue.

This is supported also by cell transport and accumulation studies using human bronchial epithelial cells. These studies show reduced flux across the cell layer for compound of formula (I) compared with fluticasone propionate. The studies also show greater accumulation of the compound of formula (I) within the cell layer compared with fluticasone propionate.

Examples of disease states in which the compound of formula (I) and compositions thereof have utility include skin diseases such as eczema, psoriasis, allergic dermatitis, neurodermatitis, pruritis and hypersensitivity reactions; inflammatory conditions of the nose, throat or lungs such as asthma (including allergen-induced asthmatic reactions), rhinitis (including hayfever), nasal polyps, chronic obstructive pulmonary disease, interstitial lung disease, and fibrosis; inflammatory bowel conditions such as ulcerative colitis and Crohn's disease; and auto-immune diseases such as rheumatoid arthritis.

The compound of formula (I) may also have use in the treatment of conjunctiva and conjunctivitis.

The complex of the invention is expected to be most useful in the treatment of inflammatory disorders of the respiratory tract e.g. asthma, COPD and rhinitis particularly asthma and rhinitis.

It will be appreciated by those skilled in the art that reference herein to treatment extends to prophylaxis as well as the treatment of established conditions.

As mentioned above, the complex of the invention is useful in human or veterinary medicine, in particular as an anti-inflammatory and anti-allergic agent.

There is thus provided as a further aspect of the invention the complex of the invention for use in human or veterinary medicine, particularly in the treatment of patients with inflammatory and/or allergic conditions, especially for treatment once-per-day.

According to another aspect of the invention, there is provided the use of the complex of the invention for the manufacture of a medicament for the treatment of patients with inflammatory and/or allergic conditions, especially for treatment once-per-day.

In a further or alternative aspect, there is provided a method for the treatment of a human or animal subject with an inflammatory and/or allergic condition, which method comprises administering to said human or animal subject an effective amount of the complex of the invention, especially for administration once-per-day.

The complex of the invention may be formulated for administration in any convenient way, and the invention therefore also includes within its scope pharmaceutical compositions comprising the complex of the invention together, if desirable, in admixture with one or more physiologically acceptable diluents or carriers. Pharmaceutical compositions suitable for once-per-day administration are of particular interest.

Further, there is provided a process for the preparation of such pharmaceutical compositions which comprises mixing the ingredients.

The complex of the invention may, for example, be formulated for oral, buccal, sublingual, parenteral, local or rectal administration, especially local administration.

Local administration as used herein, includes administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Advantageously compositions for topical administration to the lung include dry powder compositions and spray compositions.

Dry powder compositions for topical delivery to the lung by inhalation may, for example, be presented in capsules and cartridges for use in an inhaler or insufflator of, for example, gelatine. Formulations generally contain a powder mix for inhalation of the compound of the invention and a suitable powder base (carrier substance) such as lactose or starch. Use of lactose is preferred. Each capsule or cartridge may generally contain between 20 μg-10 mg of the compound of formula (I) in a pharmaceutical composition of the invention optionally in combination with another therapeutically active ingredient. Alternatively, the pharmaceutical composition of the invention may be presented without excipients. Packaging of the formulation may be suitable for unit dose or multi-dose delivery. In the case of multi-dose delivery, the formulation can be pre-metered (e.g. as in Diskus, see GB 2242134 or Diskhaler, see GB 2178965, 2129691 and 2169265) or metered in use (e.g. as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a pharmaceutical composition of the invention preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Pharmaceutical formulations which are non-pressurised and adapted to be administered as a dry powder topically to the lung via the buccal cavity (especially those which are free of excipient or are formulated with a diluent or carrier such as lactose or starch, most especially lactose) are of particular interest.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the complex of the invention optionally in combination with another therapeutically active ingredient and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid or lecithin and cosolvents e.g. ethanol. One example formulation is excipient free and consists essentially of (e.g. consists of) complex of the invention (optionally together with a further active ingredient) and a propellant selected from 1,1,1,2-tetrafluoroethane, 1,1,1,2,3, 3,3-heptafluoro-n-propane and mixture thereof. Another example formulation comprises particulate complex of the invention, a propellant selected from 1,1,1,2-tetrafluoroethane, 1,1,1,2,3,3,3-heptafluoro-n-propane and mixture thereof and a suspending agent which is soluble in the propellant e.g. an oligolactic acid or derivative thereof as described in WO94/21229. The preferred propellant is 1,1,1, 2-tetrafluoroethane. Pressurised formulations will generally be retained in a canister (e.g. an aluminium canister) closed with a valve (e.g. a metering valve) and fitted into an actuator provided with a mouthpiece.

Medicaments for administration by inhalation desirably have a controlled particle size. The optimum particle size for inhalation into the bronchial system is usually 1-10 μm, preferably 2-5 μm. Particles having a size above 20 μm are generally too large when inhaled to reach the small airways. To achieve these particle sizes the particles of the complex of the invention as produced may be size reduced by conventional means e.g. by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I) as medicament in a liquid solvent with a flowing liquid antisolvent for said medicament (e.g. as described in International Patent Application PCT/GB99/04368) or else by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (e.g. as described in International Patent Application PCT/GB00/04327).

When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 μm and not less than 15% will have a MMD of less than 15 μm.

Formulations for administration topically to the nose (e.g. for the treatment of rhinitis) include pressurised aerosol formulations and aqueous formulations administered to the nose by pressurised pump. Formulations which are non-pressurised and adapted to be administered topically to the nasal cavity are of particular interest. The formulation preferably contains water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

Other possible presentations include the following:

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

If appropriate, the formulations of the invention may be buffered by the addition of suitable buffering agents.

The proportion of the complex of the invention in the pharmaceutical compositions according to the invention depends on the precise type of formulation to be prepared but will generally be within the range of from 0.001 to 10% by weight. Generally, however for most types of preparations advantageously the proportion used will be within the range of from 0.005 to 1% and preferably 0.01 to 0.5%. However, in powders for inhalation or insufflation the proportion used will usually be within the range of from 0.1 to 5%.

Aerosol formulations are preferably arranged so that each metered dose or "puff" of aerosol contains 1 µg-2000 µg e.g. 20 µg-2000 µg, preferably about 20 µg-500 µg of the complex of the invention optionally in combination with another therapeutically active ingredient. Administration may be once daily or several times daily, for example 2, 3, 4 or 8 times, giving for example 1, 2 or 3 doses each time. Preferably the pharmaceutical composition of the invention is delivered once or twice daily. The overall daily dose with an aerosol will typically be within the range 10 µg-10 mg e.g. 100 µg-10 mg preferably, 200 µg-2000 µg.

Topical preparations may be administered by one or more applications per day to the affected area; over skin areas occlusive dressings may advantageously be used. Continuous or prolonged delivery may be achieved by an adhesive reservoir system.

For internal administration the complex according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms are, however, preferred as described below.

Preferred forms of preparation for internal administration are dosage unit forms i.e. tablets and capsules. Such dosage unit forms contain from 0.1 mg to 20 mg preferably from 2.5 to 10 mg of the complex of the invention.

The complex according to the invention may in general may be given by internal administration in cases where systemic adreno-cortical therapy is indicated.

In general terms preparations, for internal administration may contain from 0.05 to 10% of the active ingredient dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

Since the compound of formula (I) is long-acting, preferably the pharmaceutical composition of the invention will be delivered once-per-day and the dose will be selected so that the compound has a therapeutic effect in the treatment of respiratory disorders (e.g. asthma or COPD, particularly asthma) over 24 hours or more.

The pharmaceutical compositions according to the invention may also be used in combination with another therapeutically active agent, for example, a $\beta_2$ adrenoreceptor agonist, an anti-histamine or an anti-allergic. The invention thus provides, in a further aspect, a combination comprising a compound of formula (I) or a physiologically acceptable salt or solvate thereof together with another therapeutically active agent, for example a $\beta_2$-adrenoreceptor agonist, an anti-histamine or an anti-allergic.

Examples of $\beta_2$-adrenoreceptor agonists include salmeterol (e.g. as racemate or a single enantiomer such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting $\beta_2$-adrenoreceptor agonist are preferred, especially those having a therapeutic effect over a 24 hour period.

Preferred long acting $P_2$-adrenoreceptor agonists include those described in WO 02066422, WO02070490 and WO02076933.

Especially preferred long-acting $\beta_2$-adrenoreceptor agonists include compounds of formula (X):

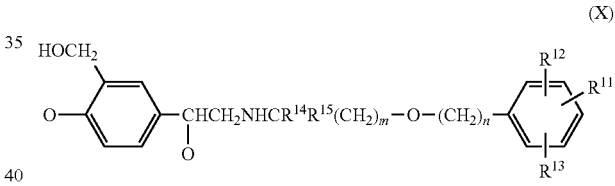

or a salt or solvate thereof, wherein:
  m is an integer of from 2 to 8;
  n is an integer of from 3 to 11,
  with the proviso that m+n is 5 to 19,
  $R^{11}$ is —$XSO_2NR^{16}R^{17}$ wherein X is —$(CH_2)_p$— or $C_{2-6}$ alkenylene;
  $R^{16}$ and $R^{17}$ are independently selected from hydrogen, $C_{1-6}$alkyl, $C_{3-7}$cycloalkyl,
    $C(O)NR^{18}R^{19}$, phenyl, and phenyl ($C_{1-4}$alkyl)-,
    or $R^{16}$ and $R^{17}$, together with the nitrogen to which they are bonded, form a 5-, 6-, or 7- membered nitrogen containing ring, and $R^{18}$ and $R^{17}$ are each optionally substituted by one or two groups selected from halo, $C_{1-6}$alkyl, $C_{1-6}$haloalkyl, $C_1$alkoxy, hydroxy-substituted $C_{1-6}$alkoxy, —$CO_2R^{18}$, —$SO_2NR^{18}R^{19}$, —$CONR^{18}R^{19}$, —$NR^{18}C(O)R^{19}$, or a 5-, 6- or 7-membered heterocyclic ring;
  $R^{18}$ and $R^{19}$ are independently selected from hydrogen, $C_{1-6}$alkyl,
    $C_{3-6}$cycloalkyl, phenyl, and phenyl ($C_{1-4}$alkyl)-; and
  p is an integer of from 0 to 6, preferably from 0 to 4;
  $R^{12}$ and $R^{13}$ are independently selected from hydrogen, $C_{1-6}$alkyl, $C_{1-6}$alkoxy, halo, phenyl, and $C_{1-6}$haloalkyl; and
  $R^{14}$ and $R^{15}$ are independently selected from hydrogen and $C_{1-4}$alkyl with the proviso that the total number of carbon atoms in $R^{14}$ and $R^{15}$ is not more than 4.

Since the compound of formula (I) is long-acting, preferably the pharmaceutical composition comprising the complex of the invention and the long-acting $\beta_2$-adrenoreceptor agonists will be delivered once-per-day and the dose of each will be selected so that the pharmaceutical composition has a therapeutic effect in the treatment of respiratory disorders effect (e.g. in the treatment of asthma or COPD, particularly asthma) over 24 hours or more.

Examples of anti-histamines include methapyrilene or loratadine.

Other suitable combinations include, for example, other anti-inflammatory agents e.g. NSAIDs (e.g. sodium cromoglycate, nedocromil sodium, PDE4 inhibitors, leukotriene antagonists, iNOS inhibitors, tryptase and elastase inhibitors, beta-2 integrin antagonists and adenosine 2a agonists)) or antiinfective agents (e.g. antibiotics, antivirals).

Also of particular interest is use of the complex n of the invention in combination with a phosphodiesterase 4 (PDE4) inhibitor e.g. cilomilast or a salt thereof.

The combination referred to above may conveniently be presented for use in the form of a pharmaceutical formulation and thus pharmaceutical formulations comprising a combination as defined above together with a physiologically acceptable diluent or carrier represent a further aspect of the invention.

The complex according to the invention in combination with another therapeutically active ingredient as described above may be formulated for administration in any convenient way, and the invention therefore also includes within its scope pharmaceutical formulations comprising the complex of the invention in combination with another therapeutically active ingredient together, if desirable, in admixture with one or more physiologically acceptable diluents or carriers. The preferred route of administration for inflammatory disorders of the respiratory tract will generally be administration by inhalation.

Further, there is provided a process for the preparation of such pharmaceutical compositions which comprises mixing the ingredients.

Therapeutic agent combinations may be in any form, for example combinations may comprise a single dose containing separate particles of individual therapeutics, and optionally excipient material(s), alternatively, multiple therapeutics may be formed into individual multicomponent particles, formed for example by coprecipitation, and optionally containing excipient material(s).

The individual compounds of such combinations may be administered either sequentially in separate pharmaceutical compositions as well as simultaneously in combined pharmaceutical formulations. Appropriate doses of known therapeutic agents will be readily appreciated by those skilled in the art.

The complex of the invention may be prepared by the methodology described hereinafter, constituting a further aspect of this invention.

A first process for preparing a complex of the invention comprises crystallising the complex from a solution containing a compound of formula (I) and the guest molecule. The solution containing the guest molecule could be the guest itself when this a liquid, or could be the guest dissolved in another liquid substance which substance does not act as a guest molecule in the process.

Optionally, for better control and reproduceability, the crystallisation process may be assisted by seeding with crystals of the complex of the invention. The seed crystals of the complex of the invention need not contain the same guest molecule.

A second process for preparing a complex of the invention comprises contacting the compound of formula (I) or a complex thereof in solid form with a liquid containing the guest molecule (for example by slurrying) and obtaining the complex therefrom. The liquid containing the guest molecule could be the guest itself when this is a liquid, or could be the guest dissolved in another liquid substance which substance does not act as a guest molecule in the process.

A third process for preparing a complex of the invention comprises contacting a compound of formula (I) or a complex thereof in solid form with a vapour containing the guest molecule. This process is suitable when the guest has acceptable volatility e.g. when the guest is a solvent.

In the second and third processes, the compound of formula (I) may be employed in the form of a complex with a guest molecule or in a form without a guest molecule (eg as unsolvated polymorph Form 1, 2 or 3). In the first process the compound of formula (I) or a complex according to the invention may be dissolved in the solution or prepared in situ.

In one particular embodiment of this aspect of the invention the input compound of formula (I) in the first, second and third processes is in the form of a substantially amorphous solid. Preferably the compound of formula (I) in the form of a substantially amorphous solid is preferably in the form of substantially amorphous particles. For example the compound of formula (I) in the form of substantially amorphous particles may be obtained by spray drying a solution containing the compound of formula (I).

Any solvent that will dissolve the compound of formula (I) that can be evaporated safely in a spray drying process may be used. Suitable solvents for forming the solution include, but are not limited to, methyl acetate, ethyl acetate, isopropyl acetate, acetone, 2-butanone, 3-pentanone, 4-methyl-2-pentanone, ethanol, methanol, 1-propanol, propan-2-ol, acetonitrile, chloroform, dichloromethane especially methylethylketone (2-butanone). Solution concentration will typically be 0.5-50% specifically 10-40% eg 20-30%. Lower concentrations may be more suitable for preparing smaller particle sizes especially 2-4% e.g. 3.5-4%. The concentration that may be employed will be limited by the dissolution power of the solvent. Methylethylketone is preferred since it dissolves compound of formula (I) at a relatively high concentration which results in production advantages. The compound of formula (I) may be employed in non-solvated form or in the form of a complex of the invention (e.g. with acetone). Preferably it is employed as the non-solvated Form 1 polymorph. Spray drying maybe performed, for example, using apparatus supplied by Buchi or Niro. A pneumatic spray nozzle orifice of e.g. 0.04 inches is suitable, although alternate atomization methods such as rotary and pressure nozzles can be used. Solution flow rate may typically be in the range 1-100 ml/min, especially 15-30 ml/min. The inlet temperature and flow rate combination should be suitable to evaporate the solvent completely to minimize the risk of solvent trapped in the particle expediting an amorphous to crystalline transition. Inlet temperatures can range from 50-250° C., typically 100-200° C.

Compound of formula (I) in unsolvated form which is itself a useful substance has been found to exist in 3 crystalline polymorphic forms, Forms 1, 2 and 3. The Forms are characterised by their XRPD patterns shown in FIG. 5. Broadly speaking the Forms are characterised in their XRPD profiles as follows:

Form 1: Peak at around 18.9 degrees 2Theta
Form 2: Peaks at around 18.4 and 21.5 degrees 2Theta
Form 3: Peaks at around 18.6 and 19.2 degrees 2Theta.

A process for preparing a compound of formula (I) as crystalline unsolvated Form 1 polymorph comprises dissolving compound of formula (I) in methylisobutylketone or ethyl acetate and producing compound of formula (I) as unsolvated Form 1 by addition of an anti-solvent such as iso-octane or toluene.

According to a first preferred embodiment of this process the compound of formula (I) may be dissolved in ethyl acetate and compound of formula (I) as unsolvated Form 1 polymorph may be obtained by addition of toluene as anti-solvent. In order to improve the yield, preferably the ethyl acetate solution is hot and once the toluene has been added the mixture is distilled to reduce the content of ethyl acetate.

According to a second preferred embodiment of this process the compound of formula (I) may be dissolved in methylisobutylketone and compound of formula (I) as crystalline unsolvated Form 1 polymorph may be obtained by addition of isooctane as anti-solvent.

A process for preparing a compound of formula (I) as unsolvated Form 2 polymorph comprises dissolving compound of formula (1) in unsolvated form in methanol or dry dichloromethane and recrystallising the compound of formula (I) as unsolvated Form 2 polymorph. Typically the compound of formula (I) will be dissolved in hot in methanol or dry dichloromethane and allowed to cool.

A process for preparing a preparing a compound of formula (I) as unsolvated Form 3 polymorph comprises dissolving compound of formula (I) in particular as the complex with acetone in dichloromethane in the presence of water (typically 1-3% water by volume) and recrystallising the compound of formula (I) as unsolvated Form 3 polymorph.

As mentioned above, complexes of the invention may also find use as manufacturing intermediates in the preparation of compound of formula (I) in unsolvated form, or in the preparation of other complexes of the invention, or in pharmaceutical compositions thereof.

For example, a process for preparation of compound of formula (I) in unsolvated form (typically unsolvated polymorph Form 1) comprises removing the guest molecule from a complex of the invention.

The methodology described herein for preparing complexes of the invention may also be useful in preparing complexes of the invention of defined crystal habit and also for preparing compounds of formula (I) in unsolvated form (typically unsolvated polymorph Form 1) of defined crystal habit. In particular the complexes of the invention with acetone are particularly advantageous since when prepared according to the method substantially as described in Example 1, second alternative method they are produced in the form of equant or substantially equant particles (typically elongated tetragonal bipyramidal crystals) which are readily micronised with high efficiency. The complexes of the invention with propan-2-ol are also particularly advantageous since when prepared according to the method substantially as described in Example 3, second and third alternative method they are produced in the form of equant or substantially equant particles (typically tetragonal bipyramidal crystals) which are also readily micronised with high efficiency. If these complexes of the invention are converted to unsolvated form (typically unsolvated Form 1) by removal of the guest molecule (eg on heating, typically to around 100-110 eg 105° C.) then the unsolvated form is prepared in the corresponding advantageous crystal habit. Unsolvated polymorph Form 1 when prepared by this method either from complexes of the invention with a acetone or complexes of the invention with propan-2-ol are much more readily micronised than the needle shaped crystals prepared by the method described above involving recrystallisation from ethylacetate and toluene. The different shaped particles are shown in FIGS. 6 to 8.

Equant and substantially equant particles may be single crystals or agglomerations of crystals. Equant particles have dimensions in each of the three axes of measurement which are approximately the same, for example they have dimensions in the three axes such that the difference between the largest and the smallest measurement is not more than approximately 50% of the smallest. Particles which are single crystals are typically equant. Particles which are agglomerations of crystals are typically substantially equant such that the particles have dimensions in the three axes such that the difference between the largest and the smallest measurement is not more than approximately 100% of the smallest, particularly not more than 50% of the smallest.

We prefer the crystalline complex of the invention to comprise equant or substantially equant particles.

We especially prefer the guest molecule to be acetone or propan-2-ol.

According to another aspect of the invention we provide a process for preparing compound of formula (I) in unsolvated form (typically unsolvated Form 1) in the form of equant or substantially equant particles by a process comprising:
(a) preparing a complex of the invention in the form of equant or substantially equant particles; and
(b) removing the guest molecule eg by heating.

In step (a), preferably the complex is a complex with propan-2-ol or acetone as guest molecule.

We also claim compound of formula (I) in unsolvated form (typically unsolvated Form 1) in the form of equant or substantially equant particles eg obtainable by such a process.

We also claim a complex according to the invention in the form of equant or substantially equant particles, especially a complex with acetone or propan-2-ol.

A process for preparing a compound of formula (I) comprises alkylation of a thioacid of formula (II)

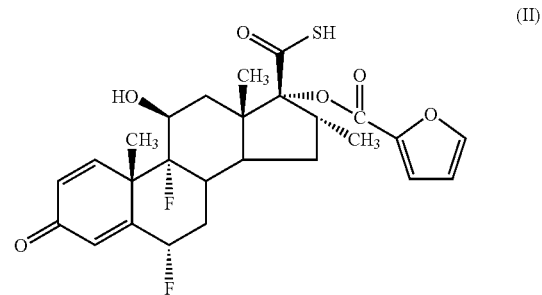

or a salt thereof.

In this process the compound of formula (II) may be reacted with a compound of formula FCH$_2$L wherein L represents a leaving group (e.g. a halogen atom, a mesyl or tosyl group or the like) for example, an appropriate fluoromethyl halide under standard conditions. Preferably, the fluoromethyl halide reagent is bromofluoromethane. Preferably the compound of formula (II) is employed as a salt, particularly the salt with diisopropylethylamine.

In a preferred process for preparing the compound of formula (I), the compound of formula (II) or a salt thereof is treated with bromofluoromethane optionally in the presence of a phase transfer catalyst. A preferred solvent is methylacetate, or more preferably ethylacetate, optionally in the presence of water. The presence of water improves solubility of both starting material and product and the use of a phase transfer catalyst results in an increased rate of reaction. Examples of phase transfer catalysts that may be employed include (but are not restricted to) tetrabutylammonium bromide, tetrabutylammonium chloride, benzyltributylammonium bromide, benzyltributylammonium chloride, benzyltriethylammonium bromide, methyltributylammonium chloride and methyltrioctylammonium chloride. THF has also successfully been employed as solvent for the reaction wherein the presence of a phase transfer catalyst again provides a significantly faster reaction rate. Preferably the product present in an organic phase is washed firstly with aqueous acid e.g. dilute HCl in order to remove amine compounds such as triethylamine and diisopropylethylamine and then with aqueous base e.g. sodium bicarbonate in order to remove any unreacted precursor compound of formula (II).

Compounds of formula (II) may be prepared from the corresponding 17α-hydroxyl derivative of formula (III):

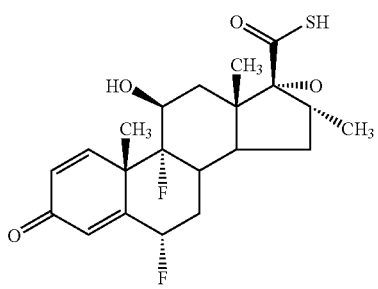

(III)

using for example, the methodology described by G. H. Phillipps et al., (1994) Journal of Medicinal Chemistry, 37, 3717-3729. For example the step typically comprises the addition of a reagent suitable for performing the esterification e.g. an activated derivative of 2-furoic acid such as an activated ester or preferably a 2-furoyl halide e.g. 2-furoyl chloride (employed in at least 2 times molar quantity relative to the compound of formula (III)) in the presence of an organic base e.g. triethylamine. The second mole of 2-furoyl chloride reacts with the thioacid moiety in the compound of formula (III) and needs to be removed e.g. by reaction with an amine such as diethylamine.

This method suffers disadvantages, however, in that the resultant compound of formula (II) is not readily purified of contamination with the by-product 2-furoyldiethylamide. We have therefore invented several improved processes for performing this conversion.

In a first such improved process we have discovered that by using a more polar amine such as diethanolamine, a more water soluble by-product is obtained (in this case 2-furoyldiethanolamine) which permits compound of formula (II) or a salt thereof to be produced in high purity since the by-product can efficiently be removed by water washing.

Thus we provide a process for preparing a compound of formula (II) which comprises:
(a) reacting a compound of formula (III) with an activated derivative of 2-furoic acid as in an amount of at least 2 moles of the activated derivative per mole of compound of formula (III) to yield a compound of formula (IIA);

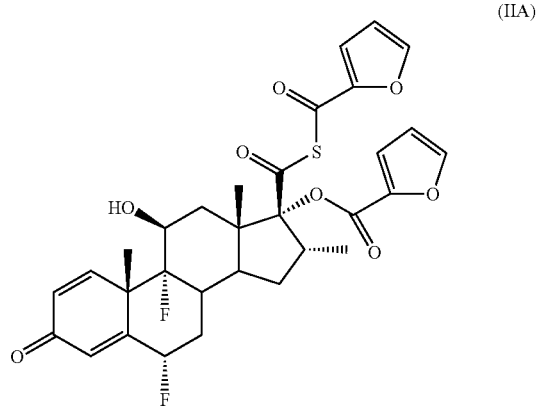

(IIA)

and
(b) removal of the sulphur-linked 2-furoyl moiety from compound of formula (IIA) by reaction of the product of step (a) with an organic primary or secondary amine base capable of forming a water soluble 2-furoyl amide.

In two particularly convenient embodiments of this process we also provide methods for the efficient purification of the end product which comprise either
(c1) when the product of step (b) is dissolved in a substantially water immiscible organic solvent, purifying the compound of formula (II) by washing out the amide by-product from step (b) with an aqueous wash, or
(c2) when the product of step (b) is dissolved in a water miscible solvent, purifying the compound of formula (II) by treating the product of step (b) with an aqueous medium so as to precipitate out pure compound of formula (II) or a salt thereof.

In step (a) preferably the activated derivative of 2-furoic acid may be an activated ester of 2-furoic acid, but is more preferably a 2-furoyl halide, especially 2-furoyl chloride. A suitable solvent for this reaction is ethylacetate or methylacetate (preferably methylacetate) (when step (c1) may be followed) or acetone (when step (c2) may be followed). Normally an organic base e.g. triethylamine will be present. In step (b) preferably the organic base is diethanolamine. The base may suitably be dissolved in a solvent e.g. methanol. Generally steps (a) and (b) will be performed at reduced temperature e.g. between 0 and 5° C. In step (c1) the aqueous wash may be water, however the use of brine results in higher yields and is therefore preferred. In step (c2) the aqueous medium is for example a dilute aqueous acid such as dilute HCl.

We also provide an alternative process for preparing a compound of formula (II) which comprises:
(a) reacting a compound of formula (III) with an activated derivative of 2-furoic acid in an amount of at least 2 moles of activated derivative per mole of compound of formula (III) to yield a compound of formula (IIA); and
(b) removal of the sulphur-linked 2-furoyl moiety from compound of formula (IIA) by reaction of the product of step (a) with a further mole of compound of formula (III) to give two moles of compound of formula (II).

In step (a) preferably the activated derivative of 2-furoic acid may be an activated ester of 2-furoic acid, but is more preferably a 2-furoyl halide, especially 2-furoyl chloride. A suitable solvent for his step is acetone. Normally an organic base e.g. triethylamine will be present. In step (b) a suitable solvent is DMF or dimethylacetamide. Normally an organic base e.g. triethylamine will be present.

Generally steps (a) and (b) will be performed at reduced temperature e.g. between 0 and 5° C. The product may be isolated by treatment with acid and washing with water.

This aforementioned process is very efficient in that it does not produce any furoylamide by-product (thus affording inter alia environmental advantages) since the excess mole of furoyl moiety is taken up by reaction with a further mole of compound of formula (II) to form an additional mole of compound of formula (II).

Further general conditions for the conversion of compound of formula (III) to compound of formula (II) in the two processes just described will be well known to persons skilled in the art.

According to a preferred set of conditions, however, we have found that the compound of formula (II) may advantageously be isolated in the form of a solid crystalline salt. The preferred salt is a salt formed with a base such as triethylamine, 2,4,6-trimethylpyridine, diisopropylethylamine or N-ethylpiperidine. Such salt forms of compound of formula (II) are more stable, more readily filtered and dried and can be isolated in higher purity than the free thioacid. The most preferred salt is the salt formed with diisopropylethylamine. The triethylamine salt is also of interest.

Compounds of formula (III) may be prepared in accordance with procedures described in GB 2088877B.

Compounds of formula (III) may also be prepared by a process comprising the following steps:

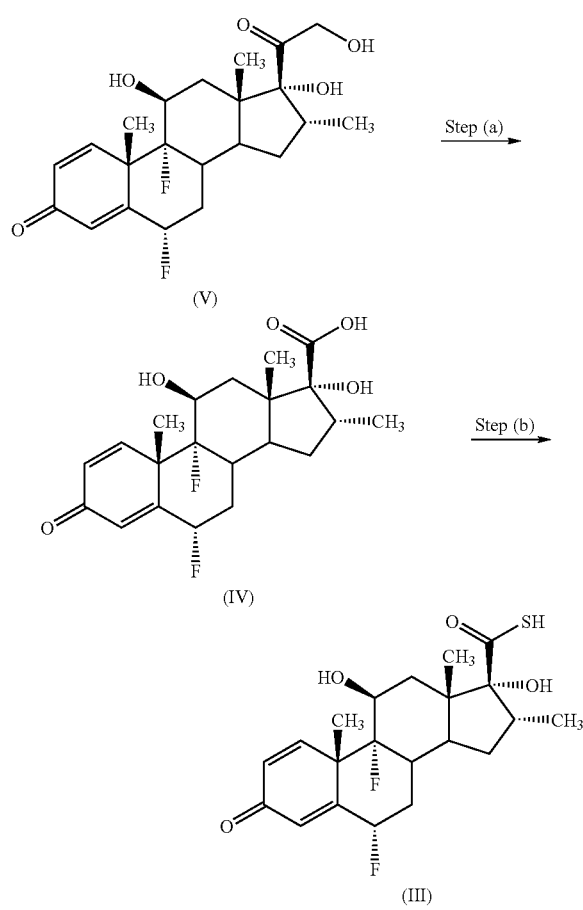

Step (a) comprises oxidation of a solution containing the compound of formula (V).

Preferably, step (a) will be performed in the presence of a solvent comprising methanol, water, tetrahydrofuran, dioxan or diethylene glygol dimethylether. So as to enhance yield and throughput, preferred solvents are methanol, water or tetrahydrofuran, and more preferably are water or tetrahydrofuran, especially water and tetrahydrofuran as solvent. Dioxan and diethylene glygol dimethylether are also preferred solvents which may optionally (and preferably) be employed together with water. Preferably, the solvent will be present in an amount of between 3 and 10 vol relative to the amount of the starting material (1 wt.), more preferably between 4 and 6 vol., especially 5 vol. Preferably the oxidising agent is present in an amount of 1-9 molar equivalents relative to the amount of the starting material. For example, when a 50% w/w aqueous solution of periodic acid is employed, the oxidising agent may be present in an amount of between 1.1 and 10 wt. relative to the amount of the starting material (1 wt.), more preferably between 1.1 and 3 wt., especially 1.3wt. Preferably, the oxidation step will comprise the use of a chemical oxidising agent. More preferably, the oxidising agent will be periodic acid or iodic acid or a salt thereof. Most preferably, the oxidising agent will be periodic acid or sodium periodate, especially periodic acid. Alternatively (or in addition), it will also be appreciated that the oxidation step may comprise any suitable oxidation reaction, e.g. one which utilises air and/or oxygen. When the oxidation reaction utilises air and/or oxygen, the solvent used in said reaction will preferably be methanol. Preferably, step (a) will involve incubating the reagents at room temperature or a little warmer, say around 25° C. e.g. for 2 hours. The compound of formula (IV) may be isolated by recrystallisation from the reaction mixture by addition of an anti-solvent. A suitable anti-solvent for compound of formula (IV) is water. Surprisingly we have discovered that it is highly desirable to control the conditions under which the compound of formula (IV) is precipitated by addition of anti-solvent e.g. water. When the recrystallisation is performed using chilled water (e.g. water/ice mixture at a temperature of 0-5° C.) although better anti-solvent properties may be expected we have found that the crystalline product produced is very voluminous, resembles a soft gel and is very difficult to filter. Without being limited by theory we believe that this low density product contains a large amount of solvated solvent within the crystal lattice. By contrast when conditions of around 10° C. or higher are used (e.g. around ambient temperature) a granular product of a sand like consistency which is very easily filtered is produced. Under these conditions, crystallisation typically commences after around 1 hour and is typically completed within a few hours (e.g. 2 hours). Without being limited by theory we believe that this granular product contains little or no solvated solvent within the crystal lattice.

Step (b) will typically comprise the addition of a reagent suitable for converting a carboxylic acid to a carbothioic acid e.g. using hydrogen sulphide gas together with a suitable coupling agent e.g. carbonyldiimidazole (CDl) in the presence of a suitable solvent e.g. dimethylformamide.

The advantages of the complex comprising a compound of formula (I) together with a guest compound according to the invention may include the fact that the substance appears to demonstrate excellent anti-inflammatory properties, with predictable pharmacokinetic and pharmacodynamic behaviour, with an attractive side-effect profile, long duration of action, and is compatible with a convenient regime of treatment in human patients, in particular being amenable to once-per day dosing. Further advantages may include the fact that the substance has desirable physical and chemical properties which allow for ready manufacture and storage. Alternatively it may serve as a useful intermediate in the preparation of other forms of the compound of formula (I) or complexes thereof.

Figure 1:
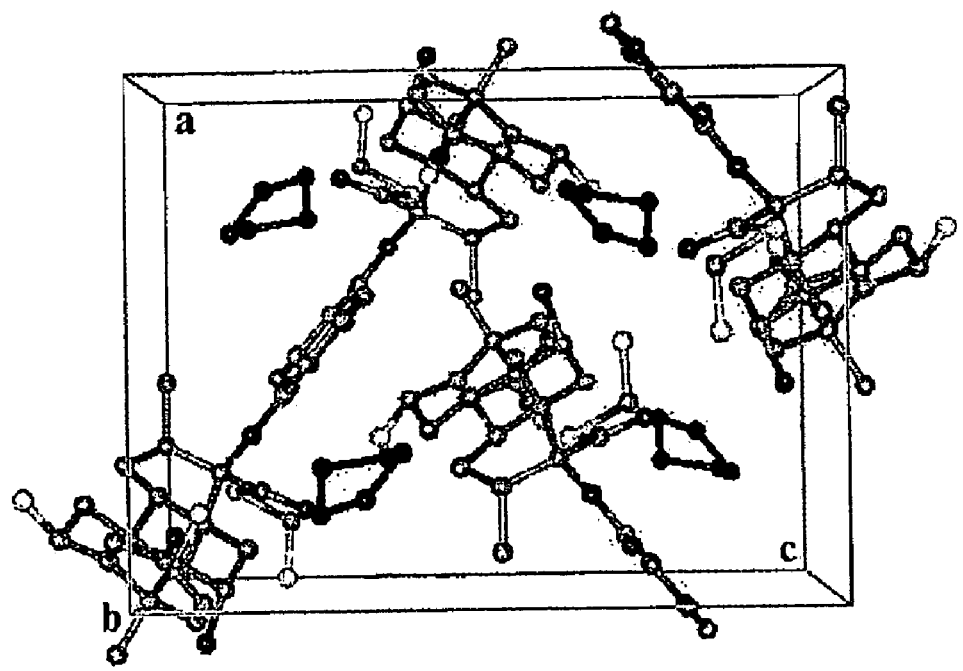
FIG. 1: Figure showing the spacial arrangement of 4 steroid and 4 guest molecules in the unit cell of complexes of the invention with THF (upper figure) and DMF (lower figure) (guest molecule darkened).
Figure 1:
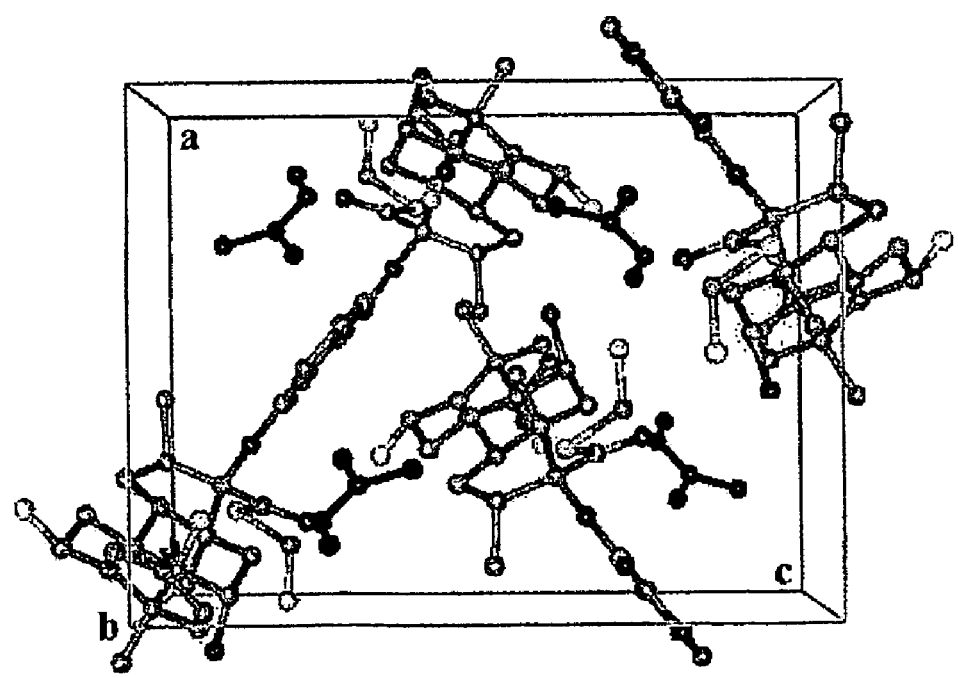
Figure 2A:
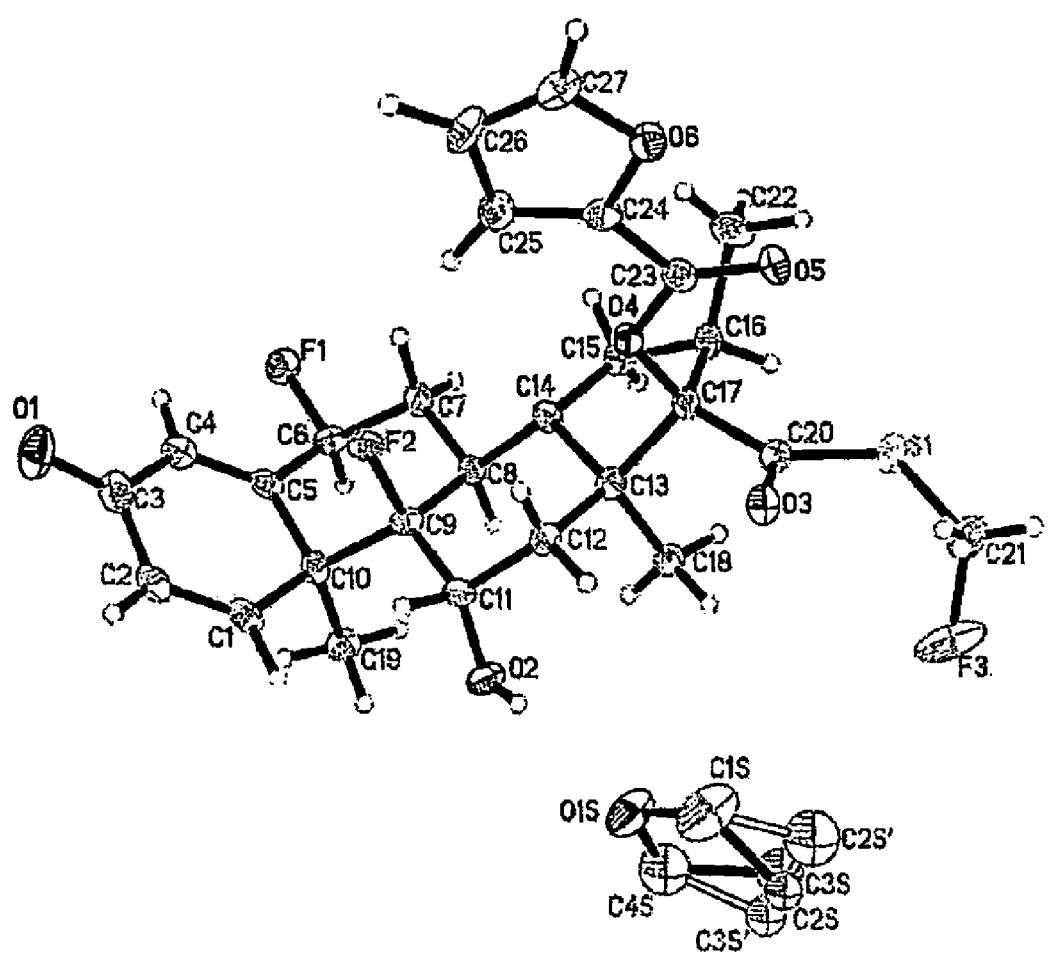
FIG. 2A: Figure showing detail of the spacial arrangement of steroid and guest molecules in complexes of the invention with THF.
Figure 2B:
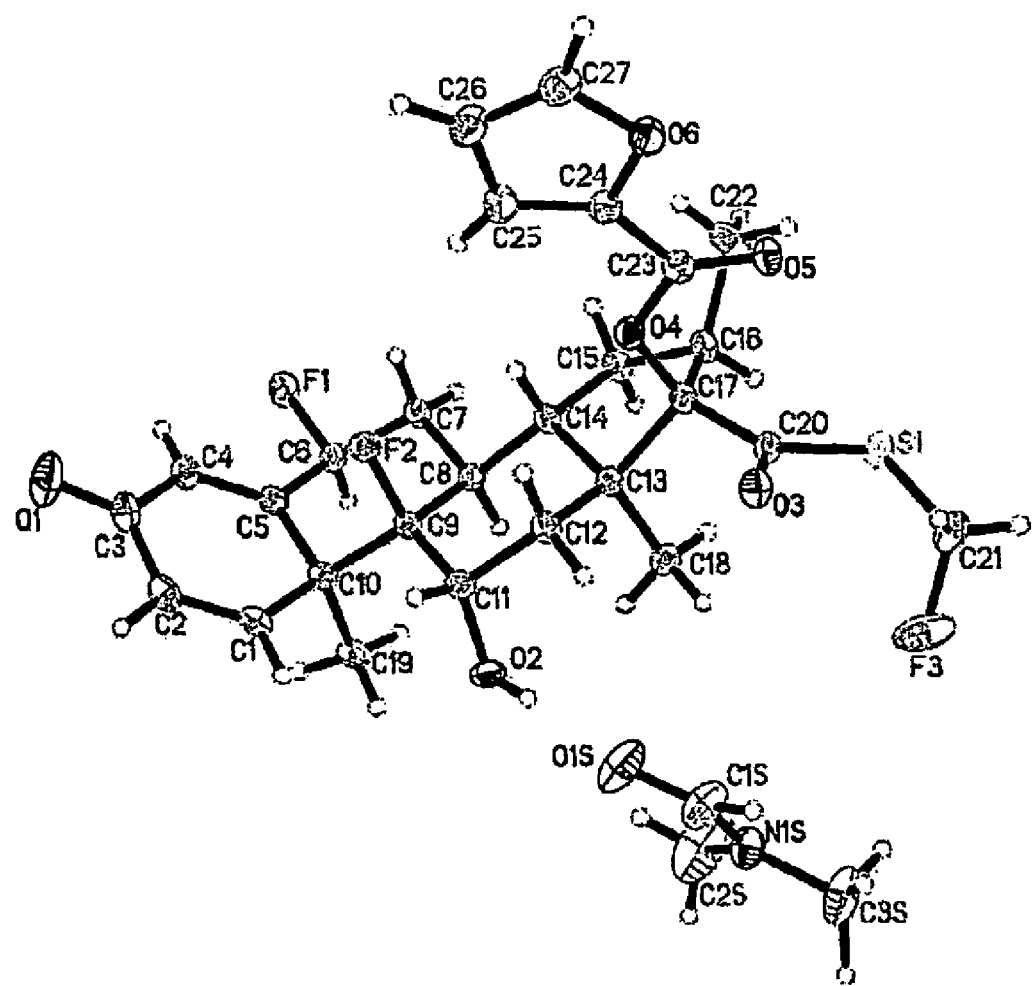
FIG. 2B: Figure showing detail of the spacial arrangement of steroid and guest molecules in complexes of the invention with DMF.
Figure 3:
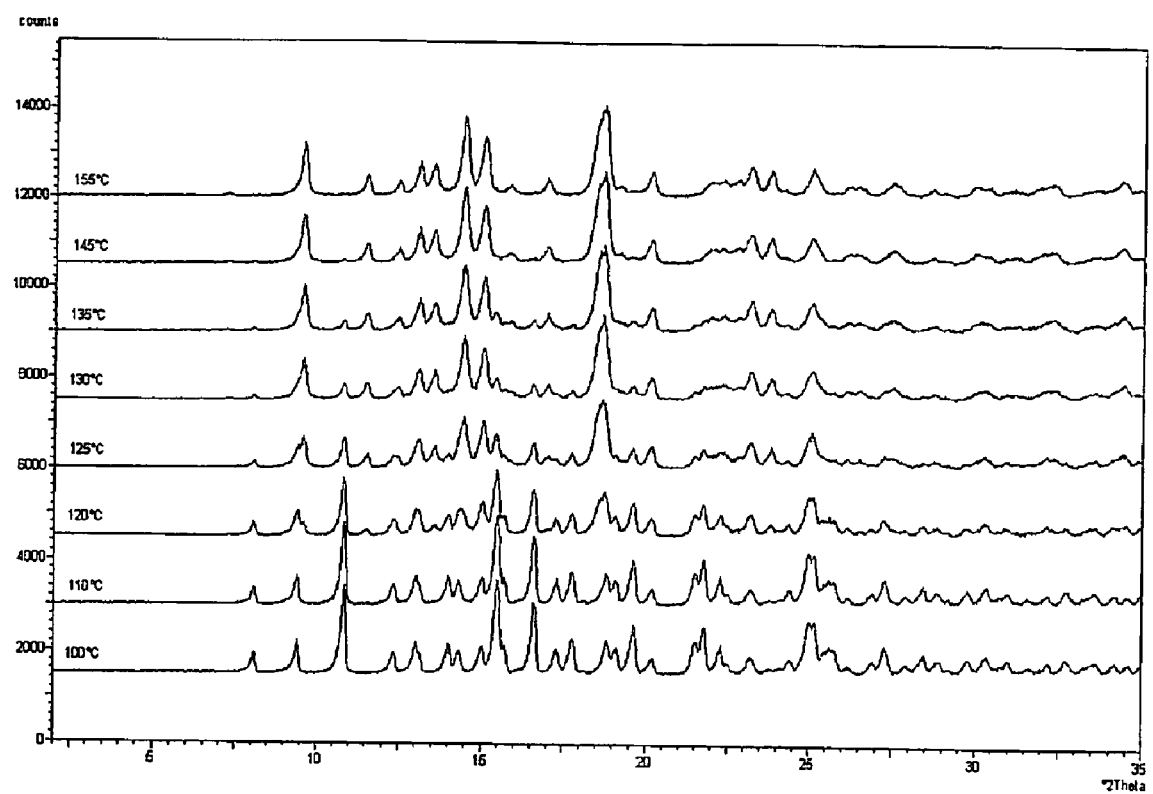
FIG. 3: Figure showing the evolution of the XRPD profile of the complex of the invention with acetone on heating, in particular showing its conversion to compound of formula (I) as unsolvated Form 1

The following non-limiting Examples illustrate the invention:

EXAMPLES

General $^1$H-nmr spectra were recorded at 400 MHz and the chemical shifts are expressed in ppm relative to tetramethylsilane. The following abbreviations are used to describe the multiplicities of the signals: s (singlet), d (doublet), t (triplet), q (quartet), m (multiplet), dd (doublet of doublets), ddd (doublet of doublet of doublets), dt (doublet of triplets) and b (broad). Biotage refers to prepacked silica gel cartridges containing KP-Sil run on flash 12i chromatography module. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0%B, 0.7-4.2 min 100%B, 4.2-5.3 min 0%B, 5.3-5.5 min 0%B at a flow rate of 3 ml/min. The mass spectra were recorded on a Fisons VG Platform spectrometer using electrospray positive and negative mode (ES+ve and ES−ve).

The XRPD analyses shown in the figures were performed on either a) a Phillips X'pert MPD powder diffractometer, serial number DY667. The pattern was recorded using the following acquisition conditions: Tube anode: Cu, Start angle: 2.0°2θ, End angle: 45.0°2θ, Step size: 0.02°2θ, Time per step: 1 second. XRPD profiles were collected at ambient temperature (295K) unless otherwise indicated, or b) a Philips PW1710 powder diffractometer. The pattern was recorded using the following acquisition conditions: Tube anode: Cu, Start angle: 3.5°2θ, End angle: 35.0°2θ, Step size: 0.02°2θ, Time per step: 2.3 seconds. XRPD profiles were collected at ambient temperature (295K).

The diffractometer used in each case can be determined by the end angle in the figure.

Raman spectra were recorded with the sample in an NMR tube using a Nicolet 960 E.S.P. FT-Raman spectrometer, at 4 cm-1 resolution with excitation from a Nd:V04 laser (1064 nm) with a power output of 400 mW.

X-ray diffraction pattern collections referred to in Table 1 were performed in the following manners:

A=The crystal and molecular structures and corresponding unit cell dimensions were determined from three-dimensional X-ray diffraction data collected at 120+/−2 K. All measurements were made using a Bruker SMART CCD diffractometer with graphite monochromated Mo-Kα radiation (λ=0.71073 Å) from a fine focus sealed tube source. The structure was solved by direct methods and refined using full-matrix least-squares procedures which minimized the function Sw(Fo$^2$- Fc$^2$)$^2$. The Bruker SHELX software was used throughout.

B=The crystal and molecular structures and corresponding unit cell dimensions were determined from three-dimensional X-ray diffraction data collected at150+/−2 K. All measurements were made using a KappaCCD diffractometer with graphite monochromated Mo-Kα radiation (λ=0.71073 Å) from a fine focus sealed tube source. The structure was solved by direct methods and refined using full-matrix least-squares procedures which minimized the function Sw(Fo$^2$-Fc$^2$)$^2$. The Bruker AXS SHELXTL software package (Ver. 5.10, UNIX) was used throughout.

C=The crystal and molecular structures and corresponding unit cell dimensions were determined from three-dimensional X-ray diffraction data collected at 150+/−2 K. All measurements were made using a Bruker AXS SMART 6000 diffractometer with graphite monochromated Cu-Kα radiation (λ=1.54178 Å) from a normal focus sealed tube source. The structure was solved by direct methods and refined using full-matrix least-squares procedures which minimized the function Sw(Fo$^2$-Fc$^2$)$^2$. The Bruker AXS SHELXTL software package (Ver. 5.10, UNIX) was used throughout.

D=as B but with collection at temperature of 295K.

The Scanning Electron Microscopy (SEM) was carried out on a Philips XL30 Scanning Electron Microscope serial number D814. An acceleration voltage in the range 20 to 25 KV was used to give magnifications in the range of 30 to 600×. Images were captured digitally using a CCD detector.

INTERMEDIATES

Intermediate 1

6α,9α-Difluoro-17α-[(2-furanylcarbonyl)oxy]-11β-hydroxy-16α-methyl-3-oxo-androsta-1,4-diene-17β-carbothioic acid diisopropylethylamine salt A stirred suspension of 6α,9α-difluoro-11β, 17α-dihydroxy-16α-methyl-3-oxo-androsta-1,4-diene-17β-carbothioic acid (prepared in accordance with the procedure described in GB 2088877B) (49.5 g) in methylacetate (500 ml) is treated with triethylamine (35 ml) maintaining a reaction temperature in the range 0-5° C. 2-Furoyl chloride (25 ml) is added and the mixture stirred at 0-5° C. for 1 hour. A solution of diethanolamine (52.8 g) in methanol (50 ml) is added and the mixture stirred at 0-5° C. for at least 2 hours. Dilute hydrochloric acid (approx 1 M, 550 ml) is added maintaining a reaction temperature below 15° C. and the mixture stirred at 15° C. The organic phase is separated and the aqueous phase is back extracted with methyl acetate (2×250 ml). All of the organic phases are combined, washed sequentially with brine (5×250 ml) and treated with di-isopropylethylamine (30 ml). The reaction mixture is concentrated by distillation at atmospheric pressure to an approximate volume of 250 ml and cooled to 25-30° C. (crystallisation of the desired product normally occurs during distillation/subsequent cooling). Tertiary butyl methyl ether (TBME) (500 ml) is added, the slurry further cooled and aged at 0-5° C. for at least 10 minutes. The product is filtered off, washed with chilled TBME (2×200 ml) and dried under vacuum at approximately 40-50° C. (75.3 g, 98.7%). NMR (CDCl$_3$) δ: 7.54-7.46 (1H, m), 7.20-7.12 (1H, dd), 7.07-6.99 (1H, dd), 6.48-6.41 (2H, m), 6.41-6.32 (1H, dd), 5.51-5.28 (1H, dddd $^2$J$_{H-F}$ 50 Hz), 4.45-4.33 (1H, bd), 3.92-3.73 (3H, bm), 3.27-3.14 (2H, q), 2.64-2.12 (5H, m), 1.88-1.71 (2H, m), 1.58-1.15 (3H, s), 1.50-1.38 (15H, m), 1.32-1.23 (1H, m), 1.23-1.15 (3H s), 1.09-0.99 (3H, d)

Intermediate 2

6α,9α-Difluoro-17α-[(2-furanylcarbonyl)oxy]-11β-hydroxy-16α-methyl-3-oxo-androsta-1,4-diene-17β-carbothioic acid S-fluoromethyl ester Unsolvated Form 1

A mobile suspension of Intermediate 1 (12.61 g, 19.8 mmol) in ethyl acetate (230 ml) and water (50 ml) is treated with a phase transfer catalyst (benzyltributylammonium chloride, 10 mol %), cooled to 3° C. and treated with bromofluoromethane (1.10 ml, 19.5 mmol, 0.98 equivalents), washing in with prechilled (0° C.) ethyl acetate (EtOAc) (20 ml). The suspension is stirred overnight, allowing to warm to 17° C. The aqueous layer is separated and the organic phase is sequentially washed with 1M HCl (50 ml), 1% w/v NaHCO$_3$ solution (3×50 ml) and water (2×50 ml). The ethylacetate solution is distilled at atmospheric pressure until the distillate reaches a temperature of approximately 73° C. at which point toluene (150 ml) is added. Distillation is continued at atmospheric pressure until all remaining EtOAc has been removed (approximate distillate temperature 103° C.). The resultant suspension is cooled and aged at <10° C. and filtered off. The bed is washed with toluene (2×30 ml) and the product oven dried under vacuum at 60° C. to constant weight to yield the title compound (8.77 g, 82%) LCMS retention time 3.66 min, m/z 539 MH$^+$, NMR δ (CDCl$_3$) includes 7.60 (1H, m), 7.18-7.11 (2H, m), 6.52 (1H, dd, J 4.2 Hz), 6.46 (1H, s), 6.41 (1H, dd, J 10, 2 Hz), 5.95 and 5.82 (2H dd, J 51, 9 Hz), 5.48 and 5.35 (1H, 2m), 4.48 (1H, m), 3.48 (1H, m), 1.55 (3H, s), 1.16 (3H, s), 1.06 (3H, d, J 7 Hz).

Intermediate 3

6α,9α-Difluoro-17α-[(2-furanylcarbonyl)oxy]-11β-hydroxy-16α-methyl-3-oxo-androsta-1,4-diene-17β-carbothioic acid A stirred suspension of 6α,9α-difluoro-11β, 17α-dihydroxy-16α-methyl-3-oxo-androsta-1,4-diene-17β-carbothioic acid (prepared in accordance with the procedure described in GB 2088877B) (1 wt, 49.5 g) in acetone (10 vol) is cooled to 0-5° C. and treated with triethylamine (0.51 wt, 2.1 eq), keeping the temperature below 5° C., and stirred for 5 min at 0-5°. 2-Furoyl chloride (0.65 wt, 2.05 eq) is then added over a minimum of 20 min, maintaining a reaction temperature at 0-5° C. The reaction mixture is stirred for at least 30 minutes and diluted with water (10 vol) maintaining a reaction temperature in the range 0-5° C. The resultant precipitate is collected by filtration and washed sequentially with acetone/water (50/50 2 vol) and water (2×2 vol). The product is dried under vacuum at approximately 55° C. overnight to leave 6α,9α-difluoro-17α-[(2-furanylcarbonyl)oxy]-11β-hydroxy-16α-methyl-3-oxo-androsta-1,4-diene-17β-yl S-(2-furanylcarbonyl) thioanhydride as a white solid (70.8 g, 98.2%) (NMR δ (CD$_3$CN) 0.99 (3H, d) (J=7.3 Hz), 1.24 (3H, s), 1.38 (1H, m) (J=3.9 Hz), 1.54 (3H, s), 1.67 (1H, m), 1.89 (1H, broad d) (J=15.2 Hz), 1.9-2.0 (1H, m), 2.29-2.45 (3H, m), 3.39 (1H, m), 4.33 (1H, m), 4.93 (1H, broad s), 5.53 (1H, ddd) (J=6.9, 1.9 Hz; J$_{HF}$=50.9 Hz), 6.24 (1H, m), 6.29 (1H, dd) (J=10.3, 2.0 Hz), 6.63 (2H, m), 7.24-7.31 (3H, m), 7.79 (1H, dd) (J=<1 Hz), 7.86 (1H, dd) (J=<1 Hz)). A portion of the product (0.56 g) is mixed with 6α,9α-difluoro-11β, 17α-dihydroxy-16α-methyl-3-oxo-androsta-1,4-diene-17β-carbothioic acid (0.41 g) in a 1:1 molar ratio in DMF (10 volumes wrt total steroid input). The reaction mixture is treated with triethylamine (approximately 2.1 equivalents) and the mixture is stirred at approximately 20° C. for approximately 6 hours. Water (50 vol) containing excess conc HCl (0.5 vol) is added to the reaction mixture and the resultant precipitate collected by filtration. The bed is washed with water (2×5 vol) and dried in vacuo at approximately 55° C. overnight to leave the title compound as a white solid (0.99 g,102%).

Intermediate 4A

6α,9α-Difluoro-17α-[(2-furanylcarbonyl)oxy]-11β-hydroxy-16α-methyl-3-oxo-androsta-1,4-diene-17β-carbothioic acid S-fluoromethyl ester, amorphous particles Intermediate 2 (30.04 g) was dissolved in methylethylketone (850 ml) to give a 3.5% solution. The solution was spray dried using a Niro Mobile Minor spray drier (Niro Inc, Columbia, Md., USA). The spray orifice was a two fluid pneumatic nozzle with 0.04 inch orifice diameter (Spray Systems Co, Wheaton, Ill., USA). The other spray drying parameters were as follows:

Temperature: 150° C., outlet temperature 98° C.
Solution flow rate: 30 ml/min using Isco 260D syringe pump (Isco Inc, Lincoln, Nebr., USA)
Atomisation Pressure: 2 Bar Particle collection was achieved in the conventional manner using a Fisher Klosterman XQ120-1.375 high efficiency cyclone (Fisher-Klosterman Inc, Louisville, Ky., USA). A white powder was recovered. The spray drying process was successful at producing smooth, spherical particles of amorphous 6α,9α-Difluoro-17α-[(2-furanylcarbonyl)oxy]-11β-hydroxy-16α-methyl-3-oxo-androsta-1,4-diene-17β-carbothioic acid S-fluoromethyl ester. System yield was 61%

Intermediate 4B

6α,9α-Difluoro-17α-[(2-furanylcarbonyl)oxy]-11β-hydroxy-16α-methyl-3-oxo-androsta-1,4-diene-17β-carbothioic acid S-fluoromethyl ester, amorphous particles Example 1 (1.26 g) was dissolved in methylethylketone (30 ml) to give a 3.8% solution. The solution was spray dried using a Buchi B-191 with spray nozzle orifice diameter of 1.0 mm. The other spray drying parameters were as follows:

Temperature: 150° C., outlet temperature 106° C.
Solution flow rate: 15 ml/min
Atomisation Pressure: 2 Bar
Process gas flow rate 14 Cubic feet per minute (CFM)

A white powder was recovered from the cyclone and collection vessel, yield 37%. The spray drying process was successful at producing smooth, spherical particles of amorphous 6α,9α-Difluoro-17α-[(2-furanylcarbonyl)oxy]-11β-hydroxy-16α-methyl-3-oxo-androsta-1,4-diene-17β-carbothioic acid S-fluoromethyl ester. The majority of the particles were between 0.5 and 4 µm.

Intermediate 5

6α,9α-Difluoro-17α-[(2-furanylcarbonyl)oxy]-11β-hydroxy-16α-methyl-3-oxo-androsta-1,4-diene-17β-carbothioic acid triethylamine salt A stirred suspension of Intermediate 3 (30 g) in ethylacetate (900 ml) is treated with triethylamine (1.05 molar equivalents, 8.6 ml) and the mixture is stirred at approximately 20° C. for 1.5 hours. The precipitate is filtered off, washed with ethylacetate (2×2 vol) and dried in vacuo at 45° C. for 18 hours to give title compound as a white solid (28.8 g, 80%). NMR (CDCl$_3$) δ: 7.59-7.47 (1H, m), 7.23-7.13 (1H, dd), 7.08-6.99 (1H, d), 6.54-6.42 (2H, m), 6.42-6.32 (1H, dd), 5.55-5.26 (1H, dddd$^2$J$_{H-F}$ 50 Hz), 4.47-4.33 (1H, bd), 3.88-3.70 (1H, bm), 3.31-3.09 (6H, q), 2.66-2.14 (5H, m), 1.93-1.69 (2H, m), 1.61-1.48 (3H, s), 1.43-1.33 (9H, t), 1.33-1.26 (1H, m), 1.26-1.15 (3H s), 1.11-0.97 (3H, d).

Pharmacological Activity

In Vitro Pharmacological Activity

Pharmacological activity was assessed in a functional in vitro assay of glucocorticoid agonist activity which is generally predictive of anti-inflammatory or anti-allergic activity in vivo.

For the experiments in this section, compound of formula (I) was used as unsolvated Form 1 (Intermediate 2)

The functional assay was based on that described by K. P. Ray et al., Biochem J. (1997), 328, 707-715. A549 cells stably transfected with a reporter gene containing the NF-κB responsive elements from the ELAM gene promoter coupled to sPAP (secreted alkaline phosphatase) were treated with test compounds at appropriate doses for 1 hour at 37° C. The cells were then stimulated with tumour necrosis factor (TNF, 10 ng/ml) for 16 hours, at which time the amount of alkaline phosphatase produced is measured by a standard colourimetric assay. Dose response curves were constructed from which $EC_{50}$ values were estimated.

In this test the compound of formula (1) showed an $EC_{50}$ value of <1 nM.

The glucocorticoid receptor (GR) can function in at least two distinct mechanisms, by upregulating gene expression through the direct binding of GR to specific sequences in gene promotors, and by downregulating gene expression that is being driven by other transcription factors (such as NFκB or AP-1) through their direct interaction with GR.

In a variant of the above method, to monitor these functions, two reporter plasmids have been generated and introduced separately into A549 human lung epithelial cells by transfection. The first cell line contains the firefly luciferase reporter gene under the control of a synthetic promoter that specifically responds to activation of the transcription factor NFκB when stimulated with TNFα. The second cell line contains the renilla luciferase reporter gene under the control of a synthetic promotor that comprises 3 copies of the consensus glucocorticoid response element, and which responds to direct stimulation by glucocorticoids. Simultaneous measurement of transactivation and transrepression was conducted by mixing the two cell lines in a 1:1 ratio in 96 well plate (40,000 cells per well) and growing overnight at 37° C. Test compounds were dissolved in DMSO, and added to the cells at a final DMSO concentration of 0.7%. After incubation for 1 h 0.5 ng/ml TNFα (R&D Systems) was added and after a further 15 hours at 37° C., the levels of firefly and renilla luciferase were measured using the Packard Firelite kit following the manufacturers' directions. Dose response curves were constructed from which $EC_{50}$ values were determined.

|  | Transactivation (GR) ED$_{50}$ (nM) | Transrepression (NFκB) ED$_{50}$ (nM) |
|---|---|---|
| Compound of Formula (I) | 0.06 | 0.20 |
| Metabolite (X) | >250 | >1000 |
| Fluticasone propionate | 0.07 | 0.16 |

In Vivo Pharmacological Activity

Pharmacological activity in vivo was assessed in an ovalbumin sensitised Brown Norway rat eosinophilia model. This model is designed to mimic allergen induced lung eosinophilia, a major component of lung inflammation in asthma.

For the experiments in this section, compound of formula (I) was used as unsolvated Form 1.

Compound of formula (I) produced dose dependant inhibition of lung eosinophilia in this model after dosing as an intra-tracheal (IT) suspension in saline 30 min prior to ovalbumin challenge. Significant inhibition is achieved after a single dose of 30 μg of compound of formula (I) and the response was significantly (p=0.016) greater than that seen with an equivalent dose of fluticasone propionate in the same study (69% inhibition with compound of formula (I) vs 41% inhibition with fluticasone propionate).

In a rat model of thymus involution 3 daily IT doses of 100 μg of compound (I) induced significantly smaller reductions in thymus weight (p=0.004) than an equivalent dose of fluticasone propionate in the same study (67% reduction of thymus weight with compound (I) vs 78% reduction with fluticasone propionate).

Taken together these results indicate a superior therapeutic index for compound (I) compared to fluticasone propionate.

In Vitro Metabolism in Rat and Human Hepatocytes

Incubation of compound (I) with rat or human hepatocytes shows the compound to be metabolised in an identical manner to fluticasone propionate with the 17-β carboxylic acid (X) being the only significant metabolite produced. Investigation of the rate of appearance of this metabolite on incubation of compound (I) with human hepatocytes (37° C., 10 μM drug concentration, hepatocytes from 3 subjects, 0.2 and 0.7 million cells/mL) shows compound (I) to be metabolised ca. 5-fold more rapidly than fluticasone propionate:

| Subject number | Cell density (million cells/mL) | 17-β acid metabolite production (pmol/h) | |
|---|---|---|---|
| | | Compound (I) | Fluticasone propionate |
| 1 | 0.2 | 48.9 | 18.8 |
| 1 | 0.7 | 73.3 | 35.4 |
| 2 | 0.2 | 118 | 9.7 |
| 2 | 0.7 | 903 | 23.7 |
| 3 | 0.2 | 102 | 6.6 |
| 3 | 0.7 | 580 | 23.9 |

Median metabolite production 102-118 pmol/h for compound (I) and 18.8-23.0 pmol/h for fluticasone propionate.

Pharmacokinetics After Intravenous (IV) and Oral Dosing in Rats

Compound (I) was dosed orally (0.1 mg/kg) and IV (0.1 mg/kg) to male Wistar Han rats and pharmacokinetic parameters determined. Compound (I) showed negligible oral bioavailability (0.9%) and plasma clearance of 47.3 mL/min/kg, approaching liver blood flow (plasma clearance of flubcasone propionate=45.2 mL/min/kg).

Pharmacokinetics After Intra-tracheal Dry Powder Dosing in the Pig

Anaesthetised pigs (2) were dosed intra-tracheally with a homogenous mixture of compound (I) (1 mg) and fluticasone propionate (1 mg) as a dry powder blend in lactose (10% w/w). Serial blood samples were taken for up to 8 h following dosing. Plasma levels of compound (I) and fluticasone propionate were determined following extraction and analysis using LC-MS/MS methodology, the lower limits of quantitation of the methods were 10 and 20 pg/mL for compound (I) and fluticasone propionate respectively. Using these methods compound (I) was quantifiable up to 2 hours after dosing and fluticasone propionate was quantifiable up to 8 hours after dosing. Maximum plasma concentrations were observed for both compounds within 15 min after dosing. Plasma half-life data obtained from IV dosing (0.1 mg/kg) was used to calculate AUC (0-inf) values for compound (I). This compensates for the plasma profile of Compound (I) only being defined up to 2 hours after an IT dose and removes any bias due to limited data between compound (I) and fluticasone propionate.

$C_{max}$ and AUC (0-inf) values show markedly reduced systemic exposure to compound (I) compared to fluticasone propionate:

| | Cmax (pg/mL) | | AUC (0-inf) (hr · pg/mL) | |
|---|---|---|---|---|
| | Pig 1 | Pig 2 | Pig 1 | Pig 2 |
| Compound of Formula (I) | 117 | 81 | 254 | 221 |
| Fluticasone propionate | 277 | 218 | 455 | 495 |

The pharmacokinetic parameters for both compound (I) and fluticasone propionate were the same in the anaesthetised pig following intravenous administration of a mixture of the two compounds at 0.1 mg/kg. The clearance of these two glucocorticoids is similar is this experimental pig model.

EXAMPLES

Example 1

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with acetone A solution of Intermediate 3 (530.1 g, 1 wt) in dimethylformamide (DMF) (8 vol) is treated with potassium hydrogen carbonate (0.202 wt, 1.02 eq) and the mixture cooled to −17±3° C. with stirring. Bromofluoromethane (BFM) (0.22 wt, 0.99 eq) is then added and the reaction stirred at −17±3° C. for at least 2 h. The reaction mixture is then added to water (17 vol) at 5±3° C. over ca 10 min followed by a water (1 vol) line wash. The suspension is stirred at 5-10° C. for at least 30 min and then filtered. The filter cake (the 6α,9α-Difluoro-17α-[(2-furanylcarbonyl)oxy]-11β-hydroxy-16α-methyl-3-oxo-androsta-1,4-diene-17β-carbothioic acid S-fluoromethyl ester complex with DMF) is washed with water (4×4 vol) and the product is pulled dry on the filter. The damp cake is returned to the vessel, acetone (5.75 vol) added and heated at reflux for 2 h. The mixture is cooled to 59±3° C. and water (5.75 vol) added, keeping temperature at 52±3° C. The mixture is then cooled to 20±3° C., filtered and dried in vacuo at 60±5° C. overnight to give the title complex as a white solid (556.5 g, 89%). NMR δ (CDCl$_3$) includes the peaks described in Intermediate 2 for the unsolvated compound and the following additional solvent peaks: 2.17 (6H, s).

Example 1

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with acetone (Alternative Method)

Intermediate 2 (1.0 g) was dissolved in approximately 60 volumes of acetone (60 mL) at reflux. The solvent level was reduced at reflux until the solution became cloudy before the flask was cooled to 21° C. over approximately 30 minutes. The flask was cooled in an ice bath for 30 minutes before the white precipitate was recovered by filtration and dried on the filter under vacuum for 30 minutes to afford the title complex (0.80 g) as a white solid.

Stoichiometry of compound of formula (I): guest=1:0.94 from $^1$H nmr (CDCl$_3$)

Example 1

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with acetone (Second Alternative Method)

Intermediate 2 (75.0 g) was dissolved in approximately 34 volumes of acetone (2550 mL) and approximately 3.7 volumes of water by heating at reflux for 15 minutes. The solution was cooled to 50° C. over approximately 30 minutes and a mixture of acetone (2 volumes, 150 mL) and water (0.3 volumes, 22 mL) was added to simulate a line wash. The reaction mixture was cooled to approximately 40° C. over 30 minutes and seed crystals of Intermediate 2 (0.75 g, 0.01 weights) were added. The reaction mixture was further cooled to approximately 22° C. over 30 minutes and then stirred at approximately 22° C. for 15 minutes. Water (30 volumes, 2250 ml) was then added to the mixture over 30 minutes and the suspension stirred at approximately 22° C. for a further 30 minutes. The suspension was filtered and the bed washed with a mixture of acetone (2 vol, 150 mL) and water (1 volume, 75 mL). The product was dried at 60° C. for 18 hours to afford the title complex (80.7 g) as a white solid.

Example 2

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with methylethylketone A suspension of Intermediate 2 (400 mg) in methylethylketone (3.2 ml) is heated to reflux giving a clear solution. A portion of the solvent is distilled off at atmospheric pressure (approx 1 ml) and the mixture cooled to approximately 20° C. The crystallised product is filtered off, dried at approximately 20° C. under vacuum to leave the title complex as a white solid (310 mg, 68%). NMR δ (CDCl$_3$) includes the peaks described for Intermediate 2 and the following additional solvent peaks: 2.45 (2H, q), 2.14 (3H, s), 1.06 (3H, t).

Example 3

6α,9α-Difluoro-17α-[(2-furanylcarbonyl)oxy]-11β-hydroxy-16α-methyl-3-oxo-androsta-1,4-diene-17β-carbothioic acid S-fluoromethyl este crystalline complex with propanol-2-ol A solution of Intermediate 2 (150 mg) in propan-2-ol (15 ml) is left to slowly crystallise over a period of approximately 8 weeks. The resultant chunky crystals are isolated by filtration to leave the title complex as a white solid. NMR δ (CDCl$_3$) includes the peaks described for Intermediate 2 and the following additional solvent peaks: 4.03 (1H, m), 1.20 (6H, d).

Example 3

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with propan-2-ol (Alternative Method)

A sample of Intermediate 2 (1.0 g) was dissolved in approximately 80 volumes of propan-2-ol (80 mL) at reflux. The solvent level was reduced at reflux until crystallisation began before the flask was cooled to 21° C. over approximately 30 minutes. The white precipitate was recovered by filtration and dried on the filter under vacuum for 30 minutes to afford the title complex as a white solid.

Stoichiometry of compound of formula (I): guest=1:0.90 from $^1$H nmr (CDCl$_3$)

Example 3

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex n with propan-2-ol (Second Alternative Method)

A sample of Intermediate 2 (82 g) was dissolved in a mixture of propan-2-ol (900 ml mL) and ethyl acetate (900 ml) at reflux. The solvent level was reduced by distillation at atmospheric distillation to approximately 12 volumes (985 ml) and the mixture seeded with authentic crystals of the desired product (ie complex with propan-2-ol, approximately 100 mg). The hot solution was cooled to 21° C. over approximately 3 hours during which time crystallisation occurred. The suspension was stirred at approximately 21° C. for 72 hours. The white precipitate was recovered by filtration and dried in vacuo to afford the title complexas a white solid (85.8 g).

Stoichiometry of compound of formula (I): guest=1:1 from $^1$H nmr (CDCl$_3$)

If desired, the propan-2-ol can be removed by the following process:

Example 3

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex n with propan-2-ol (third alternative method)

Unsolvated Form 1 in tetragonal bipyramidal habit. A sample of Intermediate 2 (1 wt) is suspended in a mixture of propan-2-ol (2 vols), water (1 vol), ethyl acetate (13 vols). The suspension is heated to reflux to give a solution. The solution is clarified by passing a 5-micron line filter, following with a line wash of ethyl acetate (2 vols). The solution is concentrated to ca 10 vols via distillation at atmospheric pressure. Propan-2-ol (10 vols) is added. The solution is seeded with the propan-2-ol solvate of (0.01 wt) suspended in propan-2-ol (ca 0.03 vols). The suspension is adjusted to 50±5 and aged for ca 5 mins (until crystallisation is established). The suspension is concentrated once again to ca 10 vols. Further propan-2-ol (10 vols) is added and the suspension concentrated to ca 10 vols for a third time (note: pot temp at this point ca80°). The suspension is cooled to 0-5° C. over ca 120 mins and aged for at least 60 mins. The white precipitate is isolated by vacuum filtration washing the filter cake with chilled propan-2-ol and dried in vacuo to afford the propan-2-ol solvate of 6α,9α-Difluoro-17α-[(2-furanylcarbonyl)oxy]-11β-hydroxy-16α-methyl-3-oxo-androsta-1,4-diene-17β-carbothioic acid S-fluoromethyl ester as tetrogonal bipyramidal particles an off-white to grey solid.

Stoichiometry of compound of formula (I): guest=1:1 from $^1$H nmr (CDCl$_3$)

The product of Example 3 (third alternative method) (85.9 g) is heated under vacuum at 105 to 115° C. for at least 12 hours to give tetragonal bipyramidal particles of unsolvated Form 1 of the active compound (77.2 g).

Example 4

6α,9α-Difluoro-17α-[(2-furanylcarbonyl)oxy]-1β-hydroxy-16α-methyl-3-oxo-androsta-1,4-diene-17β-carbothioic acid S-fluromethyl ester crystalline complex with tetrahydrofuran A suspension of Intermediate 2 (150 mg) in THF (20 vol) is warmed to give a clear solution. The solvent is allowed to slowly evaporate over a period of 6 days to leave title compound as a white solid. Alternatively, the THF solution is added dropwise to solution of potassium bicarbonate (2% w/w) in water (60 vol) and the precipitated product collected by filtration to furnish the title complex as a white solid. NMR δ (CDCl$_3$) includes the peaks described for Intermediate 2 and the following additional solvent peaks: 3.74 (4H, m), 1.85 (4H, m).

Example 4

6α,9α-Difluoro-17α-[(2-furanylcarbonyloxy]-11β-hydroxy-16α-methyl-3-oxo-androsta-1,4-diene-17β-carbothioic acid S-fluromethyl ester crystalline complex with tetrahydrofuran (First Alternative Method)

A mobile suspension of Intermediate 5 (1.2 g) in THF (10 ml) is treated with a phase transfer catalyst (tetrabutylammonium bromide, typically between 8 and 14 mol %), cooled to approximately 3° C. and treated with bromofluoromethane (0.98 equivalents). The suspension is stirred for between 2 and 5 hours, allowing to warm to 17° C. The reaction mixture is poured into water (30 vol), stirred at approximately 10° C. for 30 minutes and filtered off. The collected solid is washed with water (4×3 vol) and the product oven dried under vacuum at 60° C. overnight to give the title complex as a white solid (0.85 g, 87%).

Example 4

6α,9α-Difluoro-17α-[(2-furanylcarbonyl)oxy]-11β-hydroxy-16α-methyl-3-oxo-androsta-1,4-diene-17β-carbothioic acid S-fluromethyl ester crystalline complex with tetrahydrofuran (Second Alternative Method)

Intermediate 2 (5.0 g) was dissolved in approximately 60 volumes of tetrahydrofuran (300 mL) at reflux. The solvent level was reduced at reflux until the solution became cloudy before the flask was cooled to 21° C. over approximately 30 minutes. The white precipitate was recovered by filtration and dried on the filter under vacuum for 60 minutes to afford the title complex (4.86 g) as a white solid.

Stoichiometry of compound of formula (I): guest=1:0.95 from $^1$H nmr (CDCl$_3$)

Example 5

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with dimethylformamide A mixture of Intermediate 3 (4.5 g, 8.88 mmol) in dimethylformamide (DMF) (31 ml) is treated with potassium bicarbonate (0.89 g, 8.88 mmol) and the mixture is cooled to −20° C. A solution of bromofluoromethane (0.95 g, 8.50 mmol, 0.98 eqv.) in dimethylformamide (DMF) (4.8 ml) at 0° C. is added and the mixture is stirred at −20° C. for 4 hours. The mixture is then stirred at −20° C. for a further 30 minutes, added to 2M hydrochloric acid (100 ml) and stirred for a further 30 minutes at 0-5° C. The precipitate collected by vacuum filtration, washed with water and dried at 50° C. to give the title complex (4.47 g, 82%). NMRδ (CD$_3$OD) includes the peaks described for Intermediate 2 and the following additional solvent peaks: 7.98 (1H, bs), 2.99 (3H, s), 2.86 (3H, s).

Example 6

6α,9α-Difluoro-17α-[(2-furanylcarbonyl)oxy]-11β-hydroxy-16α-methyl-3-oxo-androsta-1,4-diene-17β-carbothioic acid S-fluoromethyl ester cyrstalline complex with butan-1-ol A mixture of Intermediate 4A (400 mg) and butan-1-ol (4 mL) was slurried at 21° C. for 61 hours. The solid was collected by filtration, dried on the filter for 2 hours and then dried under vacuum at 21° C. for 19 hours to afford the title complex as a white solid (401 mg).

Stoichiometry of compound of formula (I): guest=1:1.2 from $^1$H nmr (CDCl$_3$)

Example 7

6α,9α-Difluoro-17α-[(2-furanylcarbonyl)oxy]-11β-hydroxy-16α-methyl-3-oxo-androsta-1,4-diene-17β-carbothioic acid S-fluromethyl ester crystalline complex with methyl acetate A sample of Intermediate 2 (100 mg) was dissolved in methyl acetate (6 mL) at reflux. The solvent level was reduced to approximately 1-2 mL and the flask was removed from the heat, cooled and sealed. After sitting for 72 hours crystals of the title complex were observed in the flask.

Stoichiometry of compound of formula (I): guest=1:0.9 from $^1$H nmr (CDCl$_3$)

Example 7

6α,9α-Difluoro-17α-[(2-furanylcarbonyl)oxy]-11β-hydroxy-16α-methyl-3-oxo-androsta-1,4-diene-17β-carbothioic acid S-fluromethyl ester crystalline complex with methyl acetate (Alternative Method)

Intermediate 4A (400 mg) was slurried in methyl acetate (2 mL) at 21° C. for 5 hours. The slurry was cooled in an ice/salt bath for 20 minutes before the white solid was recovered by filtration, dried on the filter for 30 minutes and then for 2 hours at 21° C. under vacuum. An nmr showed the solvent level was less than one equivalent. The sample was placed in a methyl acetate atmosphere for 48 hours to afford the title complex (350 mg).

Stoichiometry of compound of formula (I): guest=1:1.0 from $^1$H nmr (CDCl$_3$)

Example 8

6α,9α-Difluoro-17α-[(2-furanylcarbonyl)oxy]-11β-hydroxy-16α-methyl-3-oxo-androsta-1,4-diene-17β-carbothioic acid S-fluromethyl ester crystalline complex with acetic acid A mixture of acetic acid (2 mL) and Intermediate 4A (400 mg) was slurried at 21° C. for 16 hours. The solid was recovered by filtration, dried on the filter for 1 hour at 21° C. and then dried under vacuum for 16 hours at 40° C. and 16 hours at 60° C., to afford the title complex (420 mg).

Stoichiometry of compound of formula (I): guest=1:1.3 from $^1$H nmr (CDCl$_3$)

Example 9

6α,9α-Difluoro-17α-[(2-furanylcarbonyl)oxy]-11β-hydroxy-16α-methyl-3-oxo-androsta-1,4-diene-17β-carbothioic acid S-fluromethyl ester crystalline complex with propan-1-ol A mixture of Intermediate 4A (400 mg) and propan-1-ol (2 mL) was slurried at 21° C. for 61 hours. The solid was collected by filtration, dried on the filter for 30 minutes and then dried under vacuum at 21° C. for 19 hours to afford the title complex as a white solid (390 mg).

Stoichiometry of compound of formula (I): guest=1:1.1 from $^1$H nmr (CDCl$_3$)

Example 10

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with ethanol The product of Example 3 (500 mg) was slurried in ethanol (5 mL) under vacuum at 21° C. for a total of 16 hours, replacing the ethanol as necessary. The solid was collected by filtration and dried on the filter for 2 hours to give the title complex as a white solid (438 mg).

Stoichiometry of compound of formula (I): guest=1:1.0 from $^1$H nmr (CDCl$_3$)

Example 11

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with ethyl formate Intermediate 4A (400 mg) was slurried in ethyl formate (2 mL) for 16 hours at 21° C. The solid was recovered by filtration and dried on the filter for 20 minutes to afford the title complex (396 mg).

Stoichiometry of compound of formula (I): guest=1:1.0 from $^1$H nmr (CDCl$_3$)

Example 12

6,9-Difluoro-17-[(2-furanylcarbonyl)oxy]-11-hydroxy-16-methyl-3oxo-androsta-1,4-diene-17-carbothioic acid S-fluromethyl ester crystalline complex with 1,4-dioxane A mixture of 1,4-dioxane (2.7 mL) and Intermediate 4A (270 mg) was slurried at 21° C. for 2 hours. The solid was recovered by filtration, dried on the filter for 1.5 hour at 21° C. and then dried under vacuum for 18 hours at 21° C. and 24 hours at 40° C., to afford the title complex (240 mg).

Stoichiometry of compound of formula (I): guest=1:1.25 from $^1$H nmr (CDCl$_3$)

Example 12

6,9-Difluoro-17-[(2-furanylcarbonyl)oxy]-11-hydroxy-16-methyl-3-oxo-androsta-1,4-diene-17-carbothioic acid S-fluromethyl ester crystalline complex with 1,4-dioxane (Alternative Method)

Intermediate 2 (1 g) was disolved in a mixture of 1,4-dioxane (40 mL) water (0.6 mL) at reflux and allowed to cool to approximately 27° C. The solution was added to stirred water (50 ml) over approximately 45 minutes. The suspension was stirred at approximately 20° C. for 1 hour. The solid was recovered by filtration and then dried under vacuum for 18 hours at 60° C. and 4 hours at 80° C., to afford the title complex (1.07 g).

Stoichiometry of compound of formula (I): guest=1:0.99 from $^1$H nmr (CDCl$_3$)

Example 13

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with dimethylsulfoxide A mixture of Intermediate 4A (400 mg) and dimethylsulfoxide (2 mL) was slurried at 21° C. for 30 minutes. The white solid was collected by filtration and dried in a dessicator over phosphorus pentoxide under high vacuum at 21° C. for 3 hours to afford the title complex.

Stoichiometry of compound of formula (I): guest=1:1.2 from $^1$H nmr (CDCl$_3$)

Example 14

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with n-methyl-2-pyrrolidinone Intermediate 2 (100 mg) was disolved in N-methyl-2-pyrrolidinone (1 mL) at approximately 20° C. The solution was added to a solution of potassium hydrogen carbonate (100 mg) in water (5 ml) over approximately 10 seconds. The solid was recovered by filtration and then dried under vacuum at approximately 60° C. for 16 hours to afford the title complex.
Stoichiometry of compound of formula (I): guest=1:0.9 from $^1$H nmr (CDCl$_3$)

Example 15

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with dimethylacetamide Intermediate 2 (100 mg) was disolved in dimethylacetamide (0.5 mL) at approximately 20° C. and left to slowly crystalise over a period of 6 days. The solid was recovered by filtration and then dried under vacuum at approximately 60° C. for 16 hours to afford the title complex.
Stoichiometry of compound of formula (I): guest=1:1 from $^1$H nmr (CDCl$_3$)

Example 16

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with water Intermediate 4A (500 mg) was slurried in water (10 mL) for 16 hours. The solid was collected by filtration, dried for 16 hours under vacuum at 21° C., and then placed in a humid atmosphere for 48 hours to afford the title complex (444 mg) as a white solid.
Stoichiometry of compound of formula (I): guest=1:1 from water analysis.

Example 17

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with t-butylamine Intermediate 4A (200 mg) was slurried in t-butylamine (5 mL) at 21° C. for 30 minutes. The solid was collected by filtration and dried for approximately 3 hours under vacuum over phosphorus pentoxide to provide the title complex as a white solid.
Stoichiometry of complex of formula (I): guest=1:1.3 from $^1$H nmr (CDCl$_3$).

Example 18

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with □-caprolactam ε-Caprolactam (50mg) (Aldrich) was heated in a glass vial to 80° C. where the solid had melted. Intermediate 4A (200 mg) was added and the mixture was agitated using a small magnetic stirrer bar. The mixture was stirred at 80° C. for 1 hour before the resulting mixture was allowed to cool to 21° C. and the solid was recovered to afford the title complex.

Example 19

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with pyridine Intermediate 2 was dissolved in pyridine at 80° C. The solution was cooled before the solid was collected to afford the title complex.

Example 20

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with cyclohexylamine Intermediate 2 was dissolved in cyclohexylamine at 95° C. The solution was cooled to room temperature and maintained at that temperature for 1 hour before the solid was collected to afford the title complex.

Example 21

6α,9α-Difluoro-17α-[(2-furanylcarbonyl)oxy]-11β-hydroxy-16α-methyl-3-oxo-androsta-1,4-diene-17β-carbothioic acid S-fluoromethyl ester crystalline complex with cyclohexanone Intermediate 2 was dissolved in cyclohexanone at 95° C. The solution was slowly cooled to room temperature and maintained at that temperature for 16 hour before the solid was collected to afford the title complex.

Further characterising data on complexes of the invention is provided in Tables 2 to 19.

Positions of bands in the Raman spectrum of various complexes of the invention are provided in Table 20.

Figure 4:
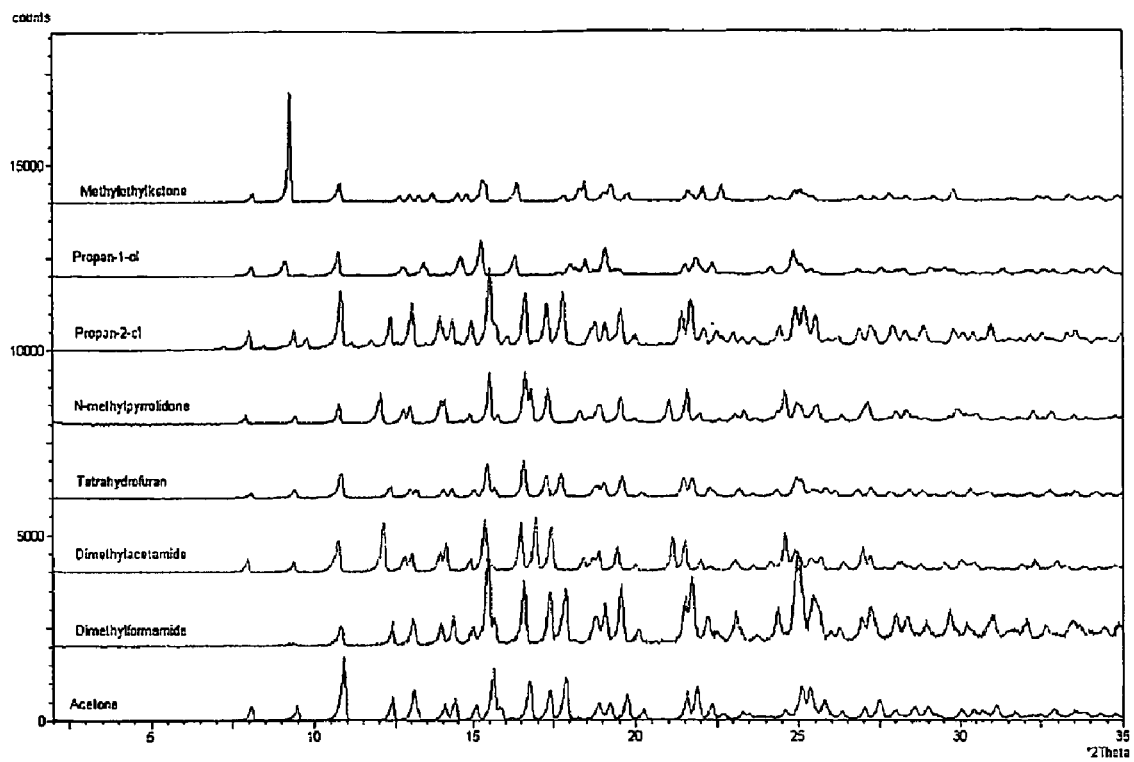
FIG. 4: XRPD profiles for a range of complexes according to the invention (refer to Table 1)
Figure 4:
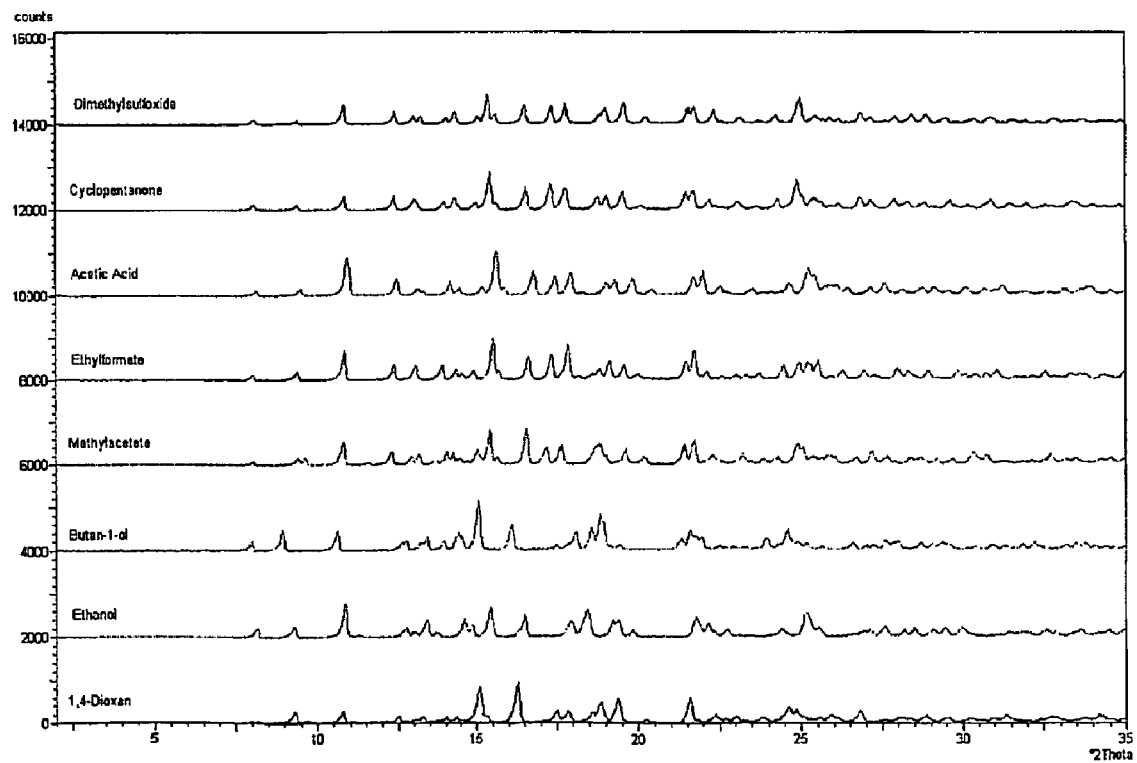
Figure 5:
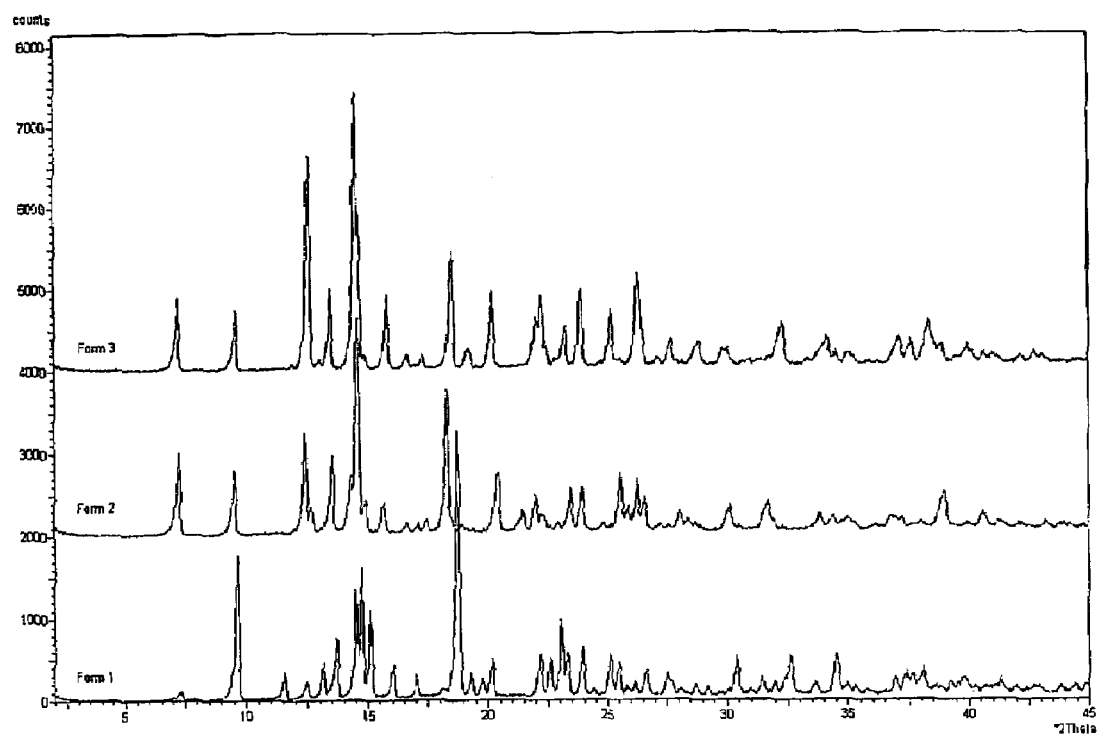
FIG. 5: Comparison of XRPD profiles of Form 1, Form 2 and Form 3 polymorphs of unsolvated compound of formula (I).
Figure 6:
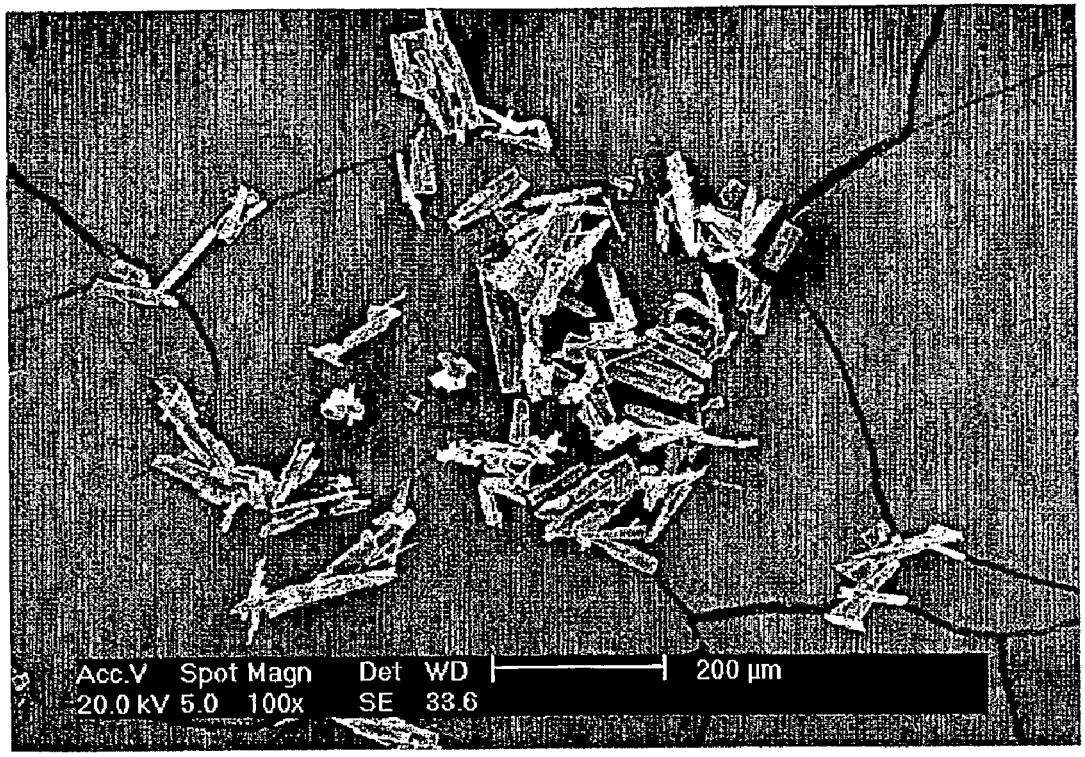
FIG. 6: Scanning Electron Microscopy (SEM) study of crystals of unsolvated polymorph Form 1.
Figure 6:
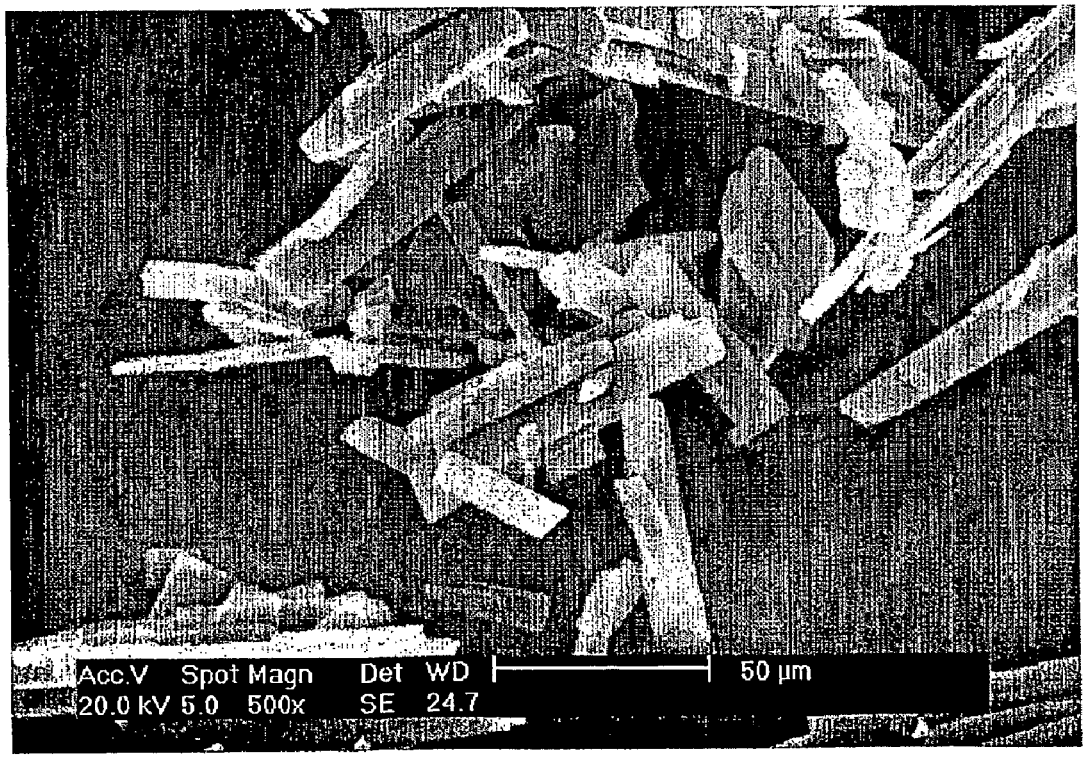
Figure 7:
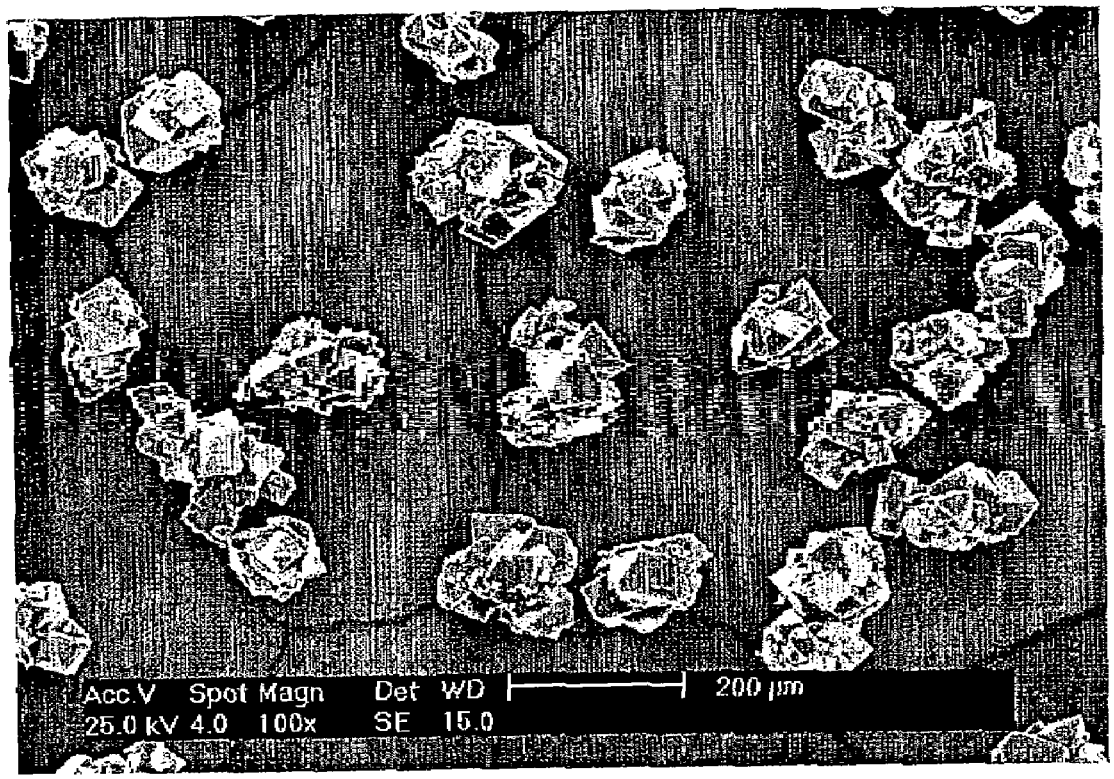
FIG. 7: Scanning Electron Microscopy (SEM) study of crystals of complexes of the invention with acetone
Figure 7:
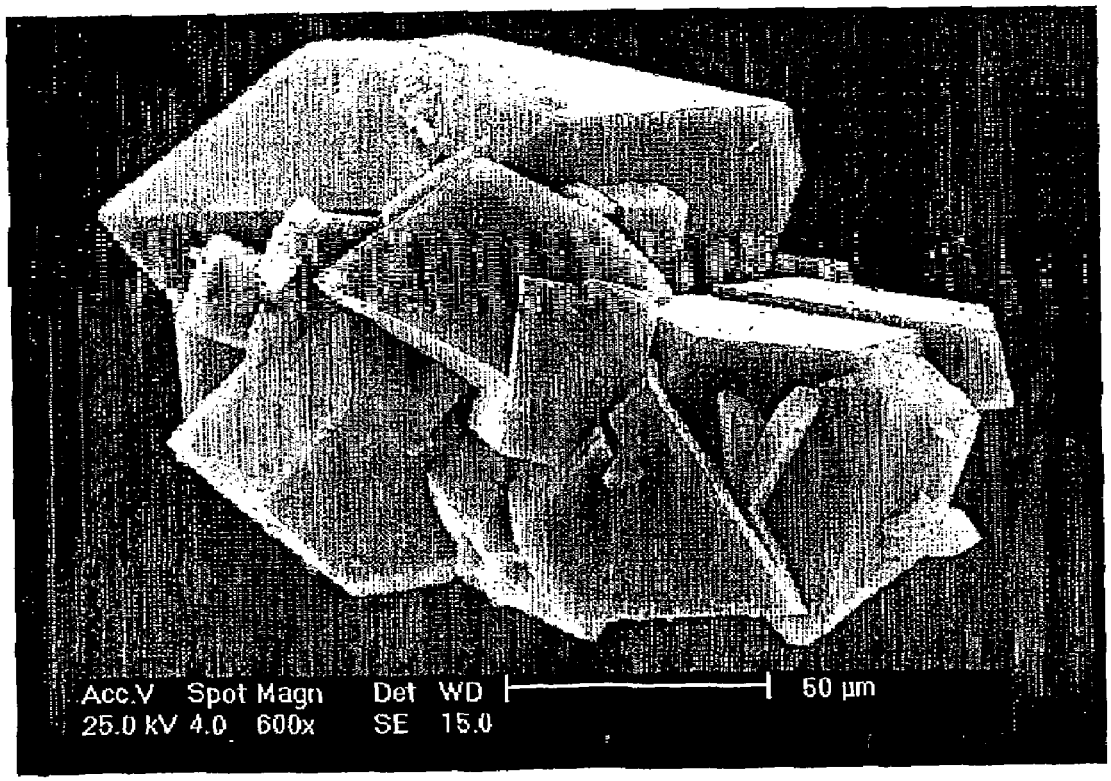
Figure 8:
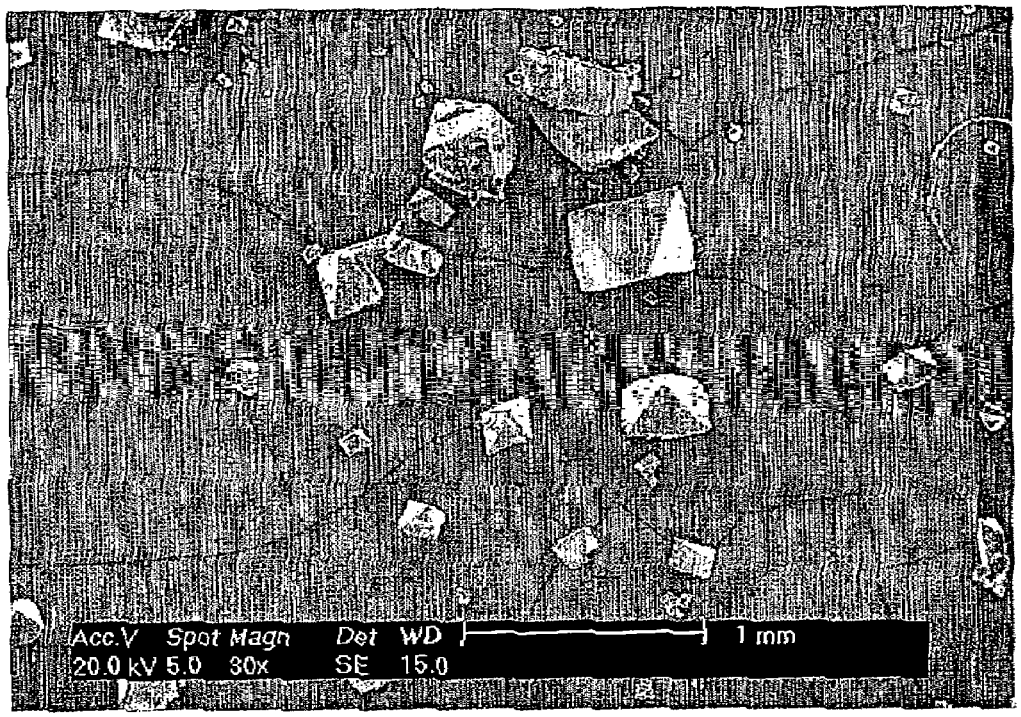
FIG. 8: Scanning Electron Microscopy (SEM) study of crystals of complexes of the invention with propan-2-ol.
Figure 8:
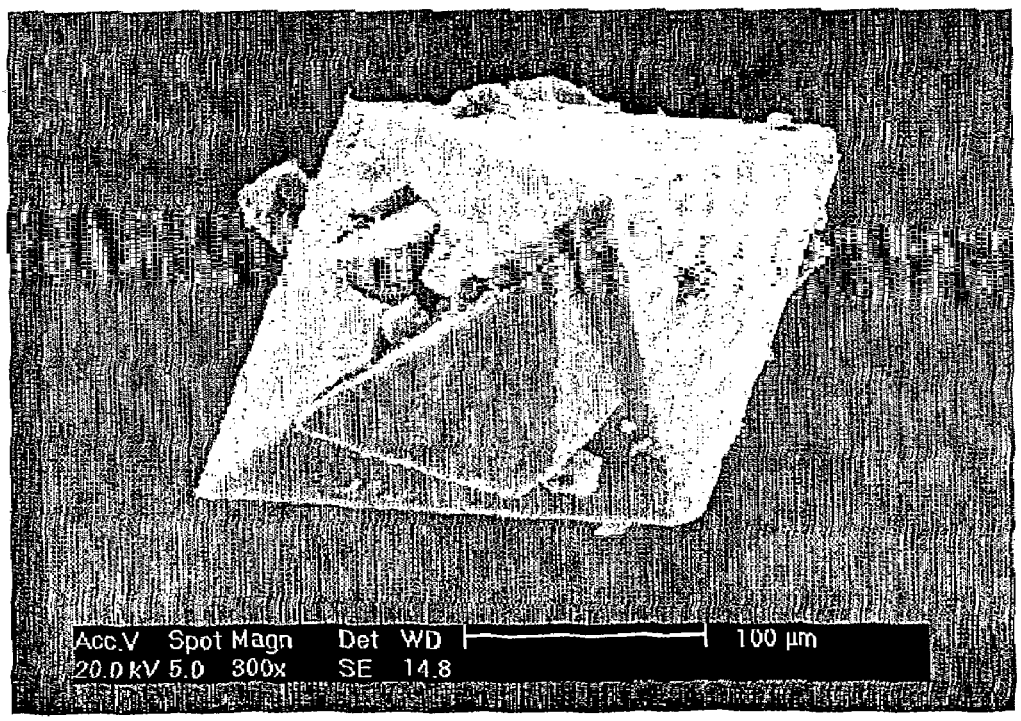
Figure 9:
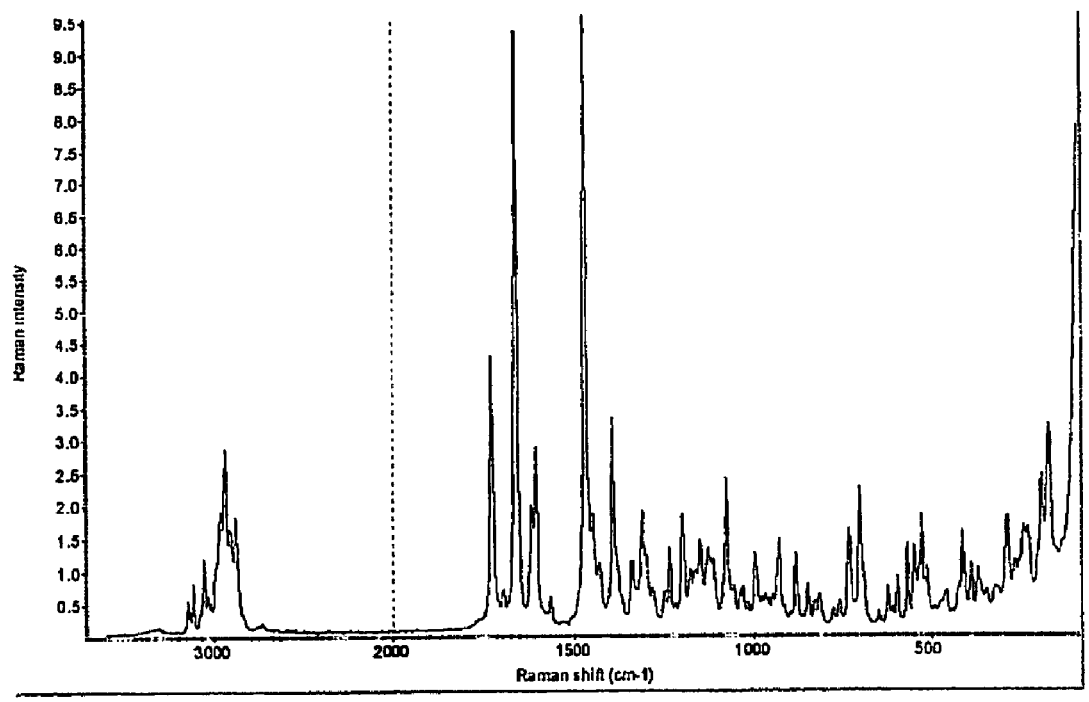
FIG. 9: Raman spectrum of complexes of the invention with butan-1-ol
Figure 10:
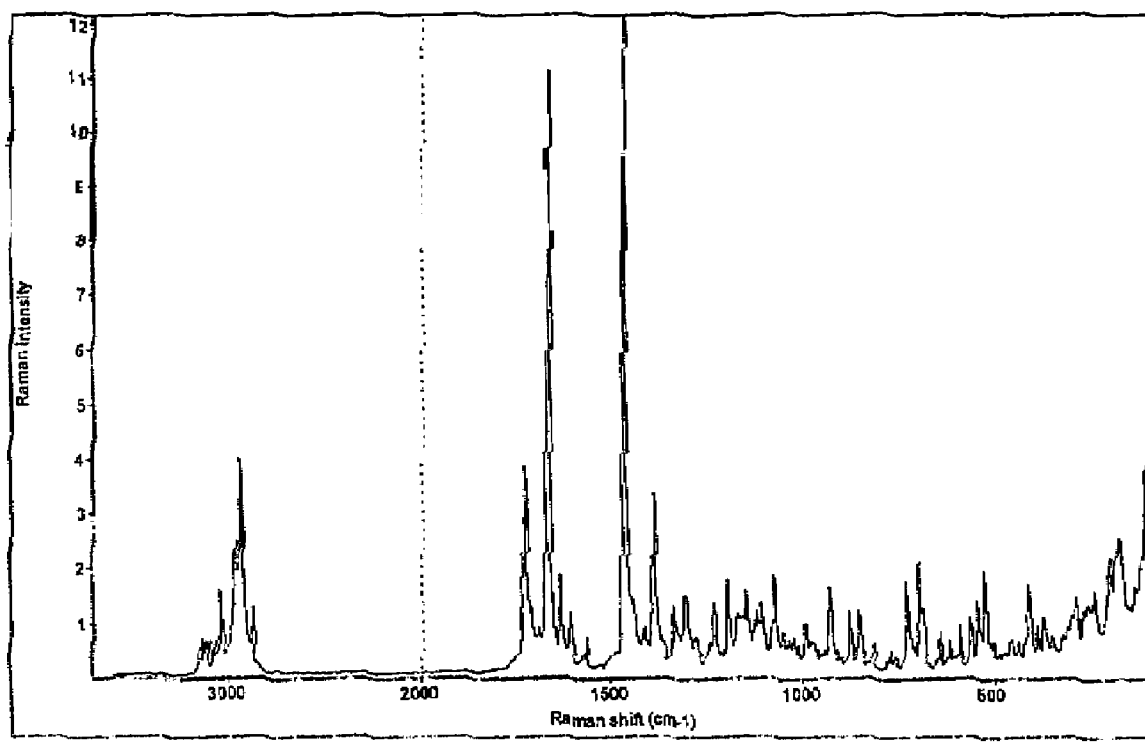
FIG. 10: Raman spectrum of complexes of the invention with methyl acetate
Figure 11:
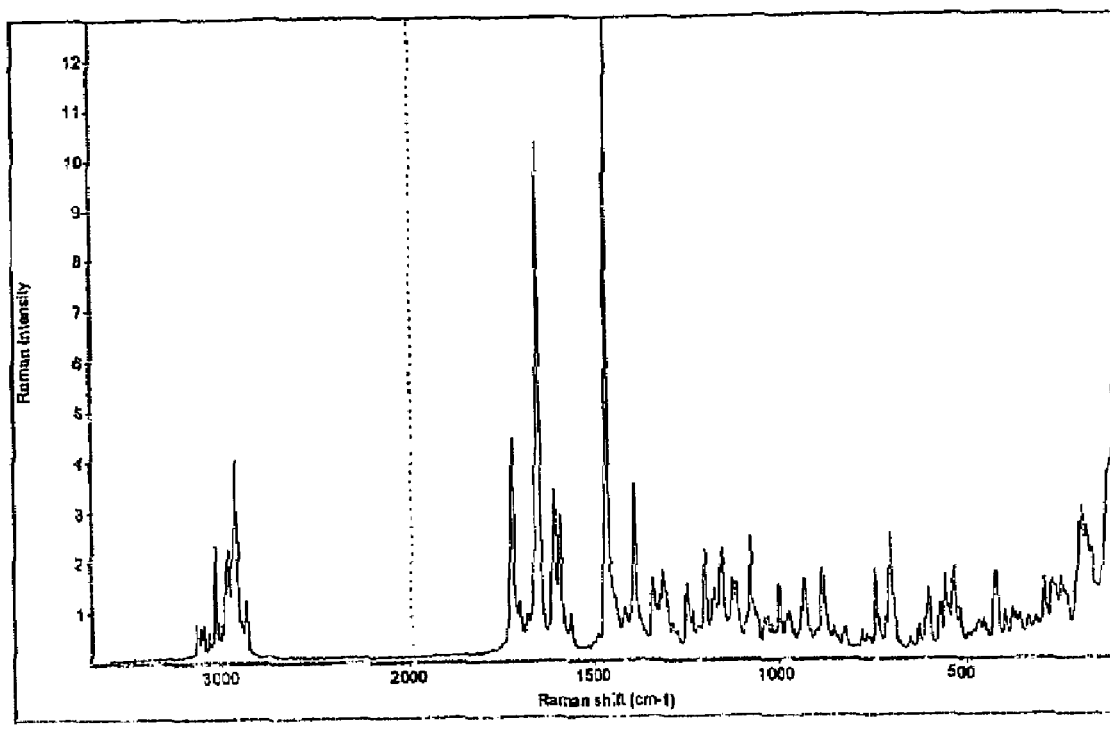
FIG. 11: Raman spectrum of complexes of the invention with acetic acid
Figure 12:
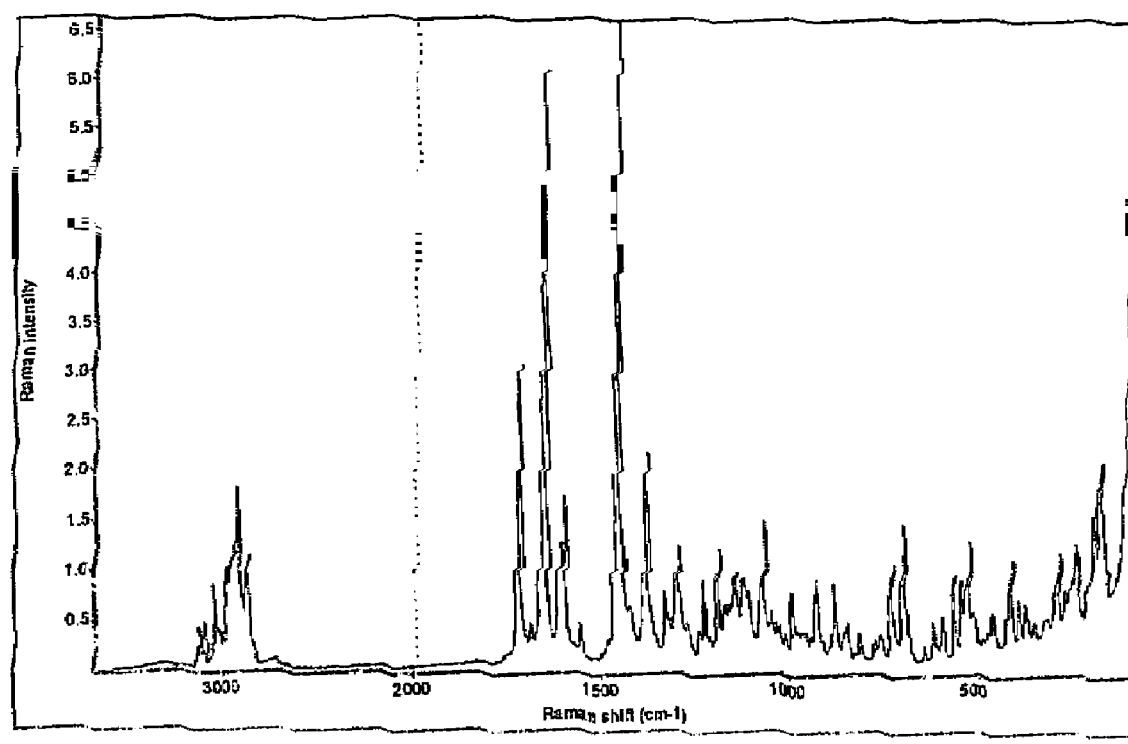
FIG. 12: Raman spectrum of complexes of the invention with propan-1-ol
Figure 13:
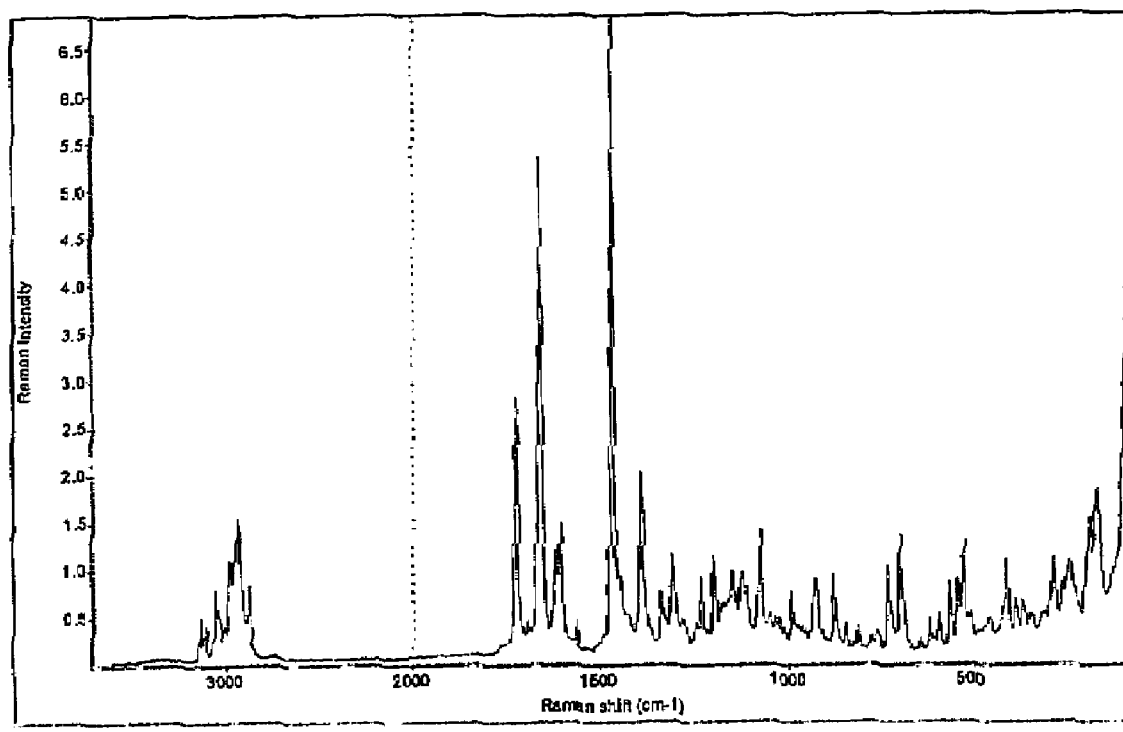
FIG. 13: Raman spectrum of complexes of the invention with ethanol
Figure 14:
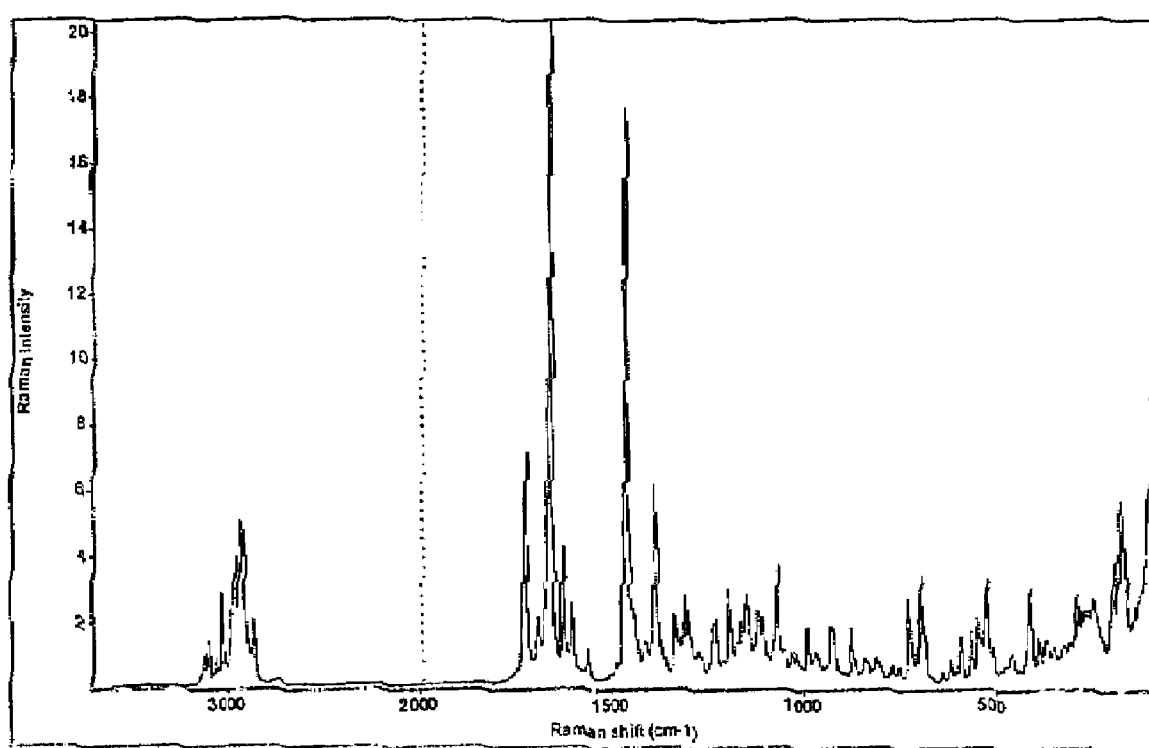
FIG. 14: Raman spectrum of complexes of the invention with ethyl formate
Figure 15:
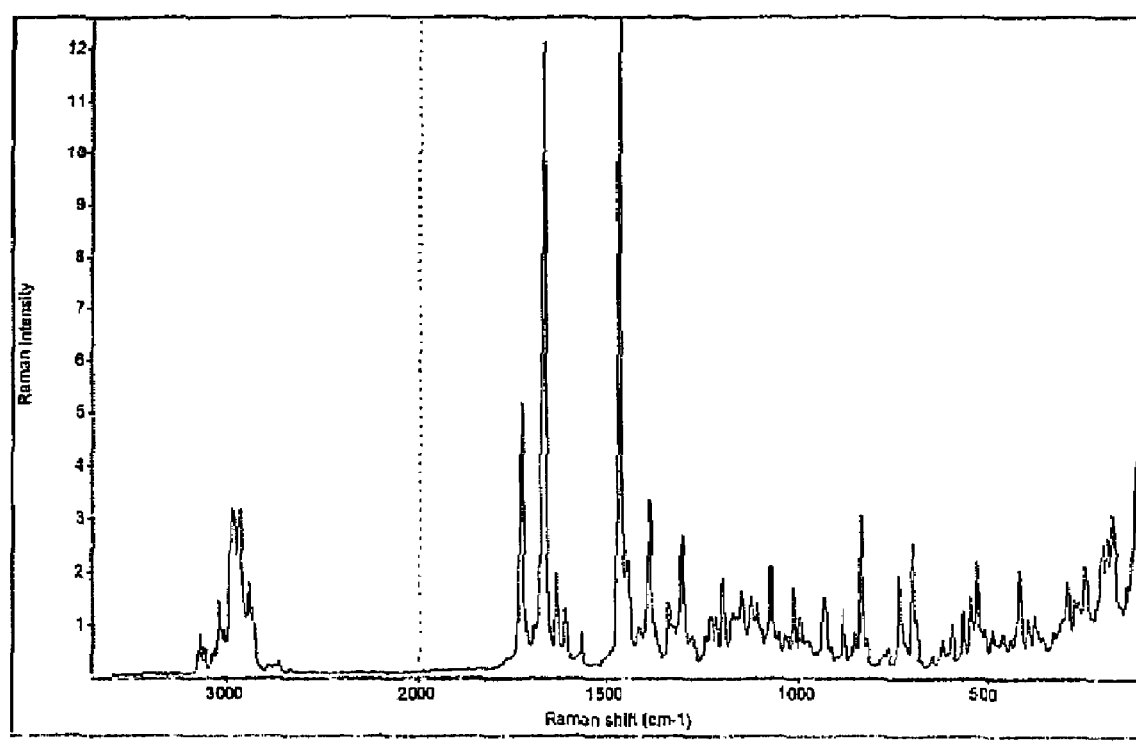
FIG. 15: Raman spectrum of complexes of the invention with 1,4-dioxane
Figure 16:
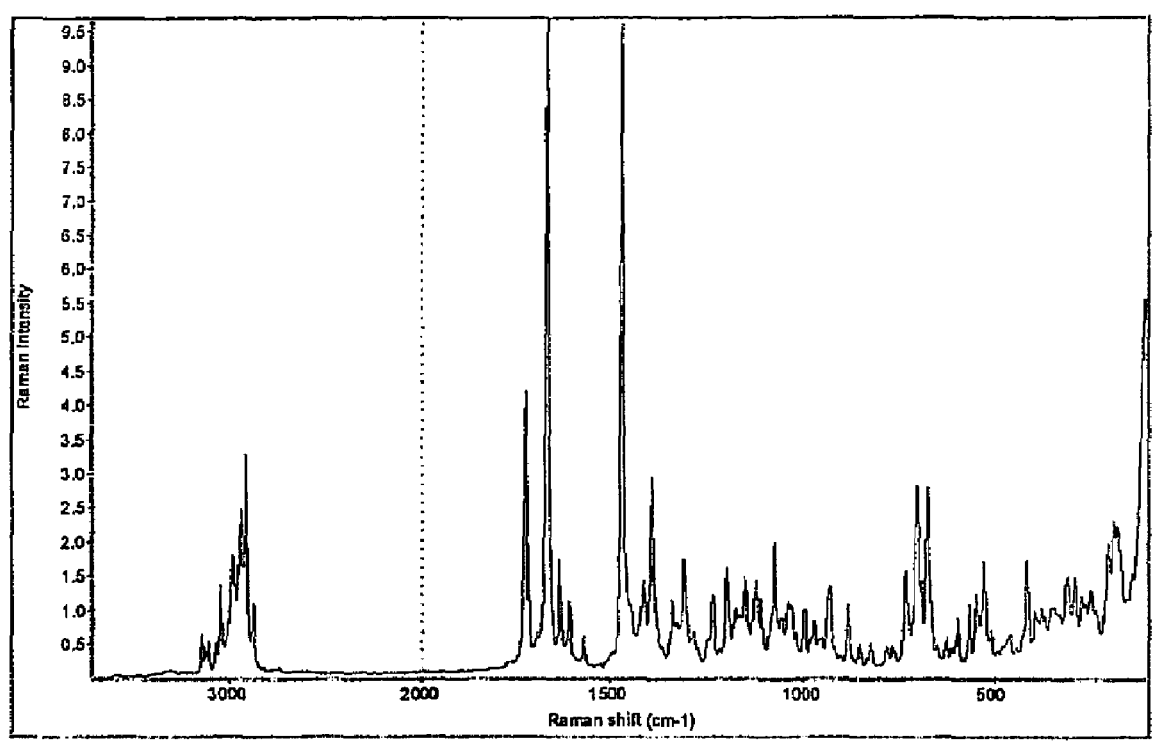
FIG. 16: Raman spectrum of complexes of the invention with dimethylsulphoxide
Figure 17:
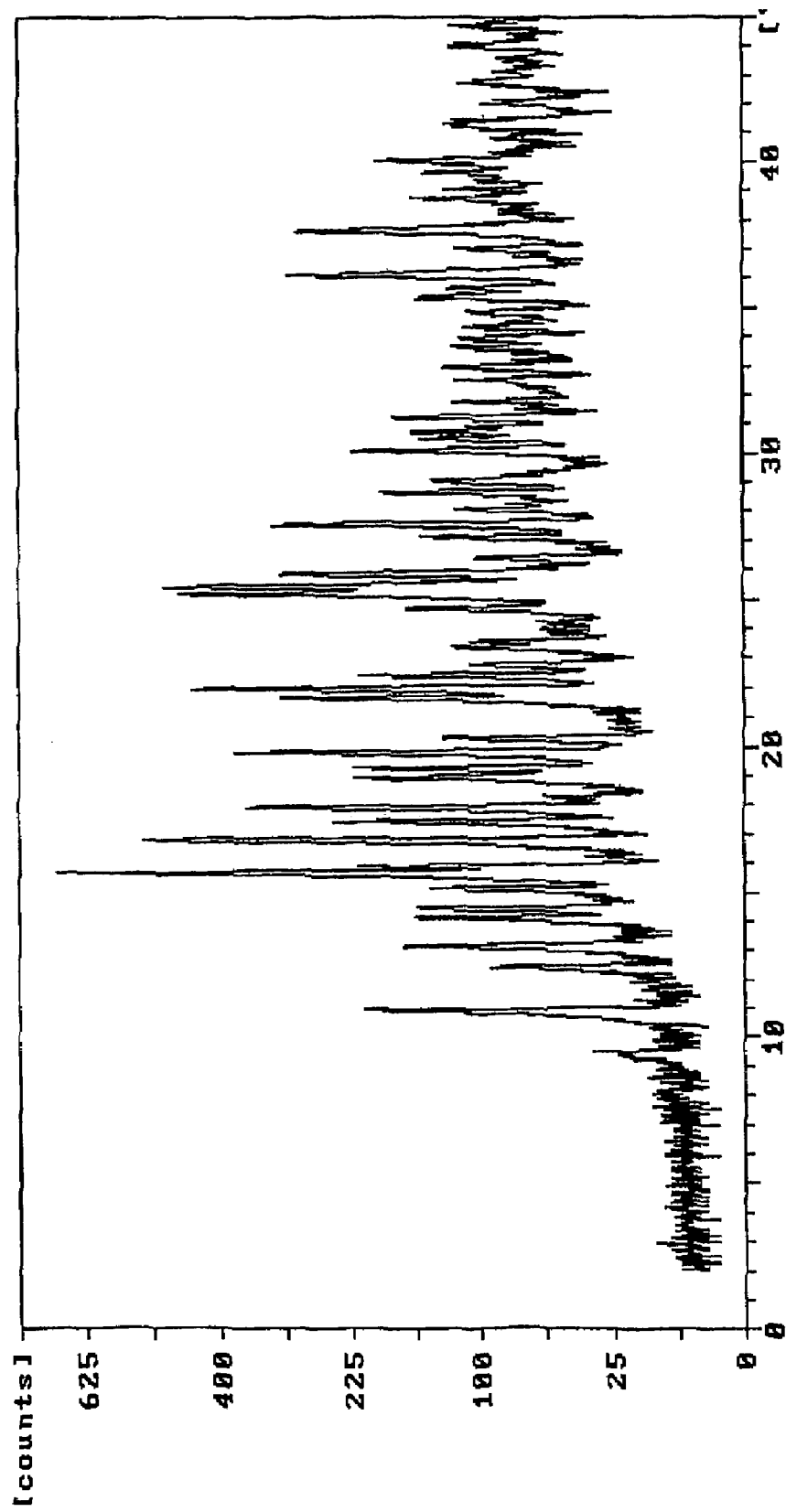
FIG. 17: Enlarged XRPD profile of complexes of the invention with acetone
Figure 18:
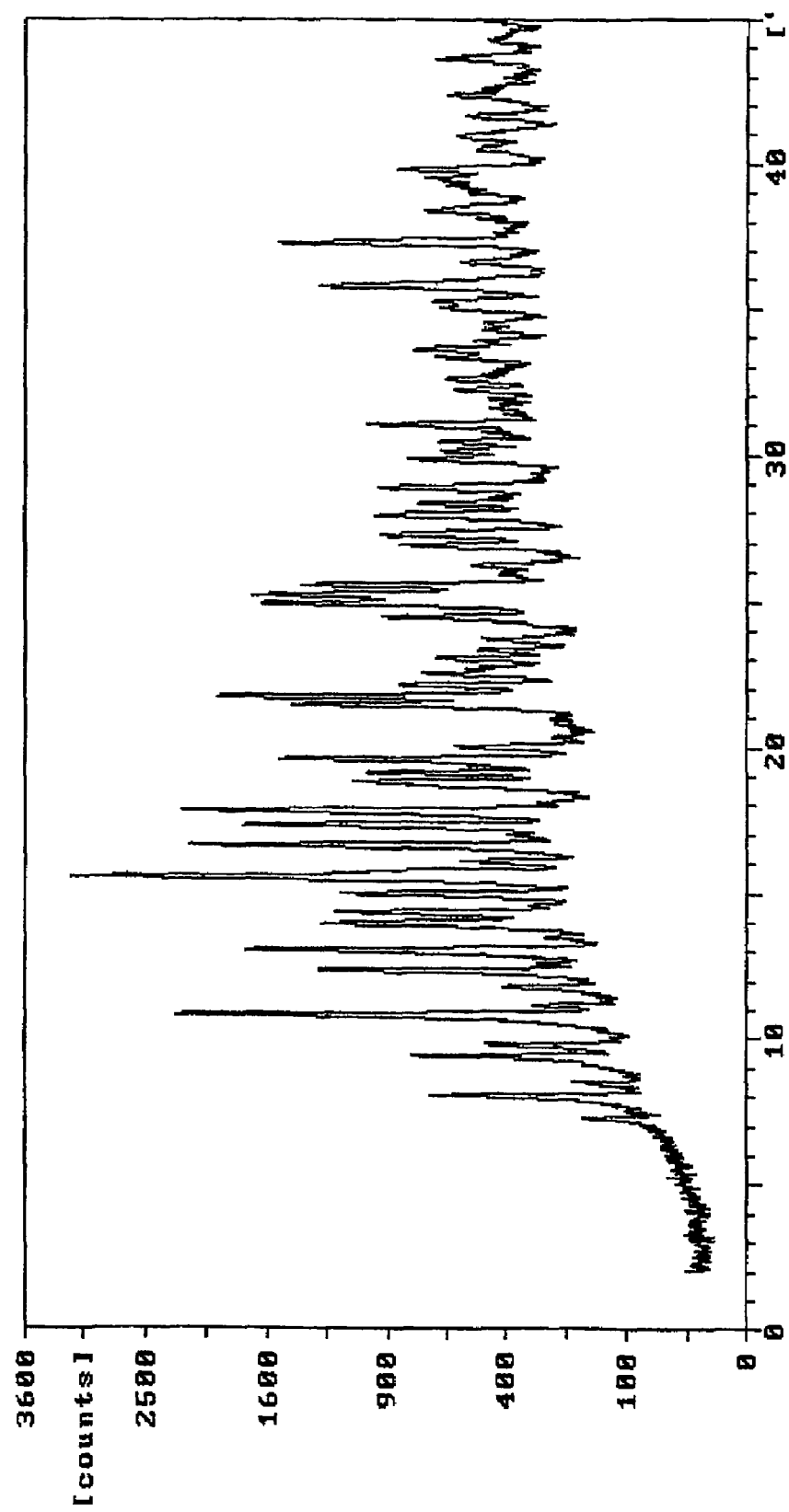
FIG. 18: Enlarged XRPD profile of complexes of the invention with methylethylketone
Figure 19:
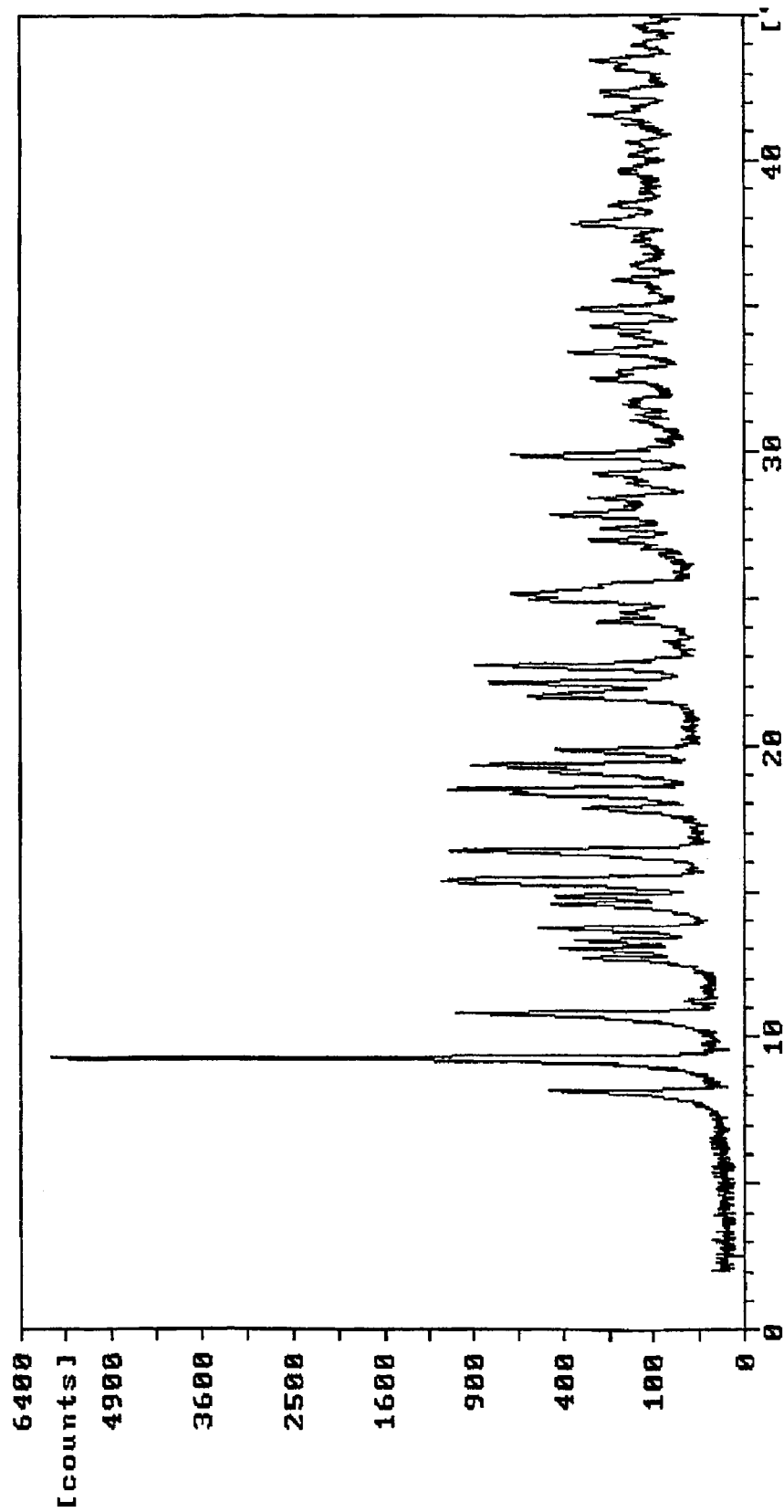
FIG. 19: Enlarged XRPD profile of complexes of the invention with propan-2-ol
Figure 20:
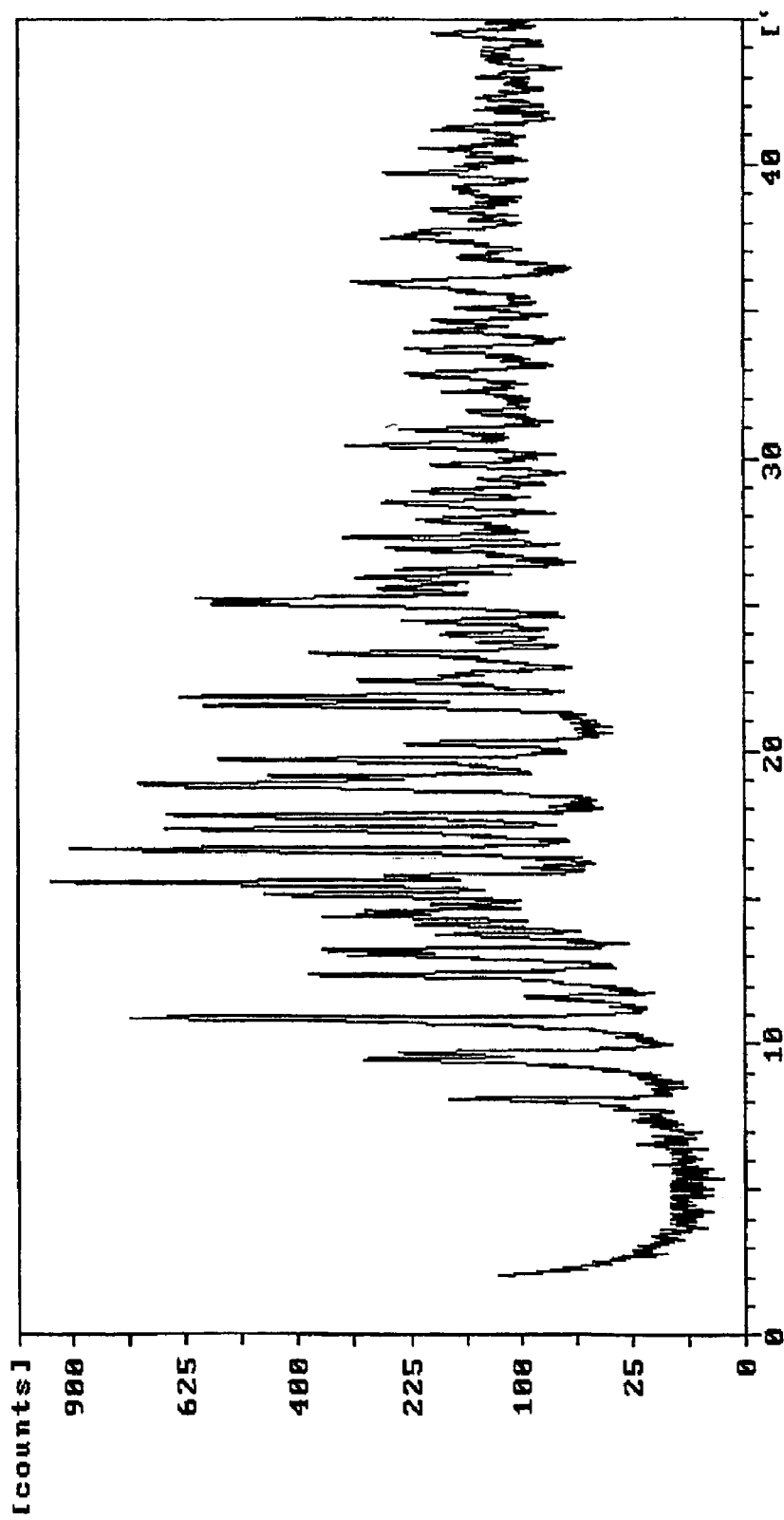
FIG. 20: Enlarged XRPD profile of complexes of the invention with tetrahydrofuran
Figure 21:
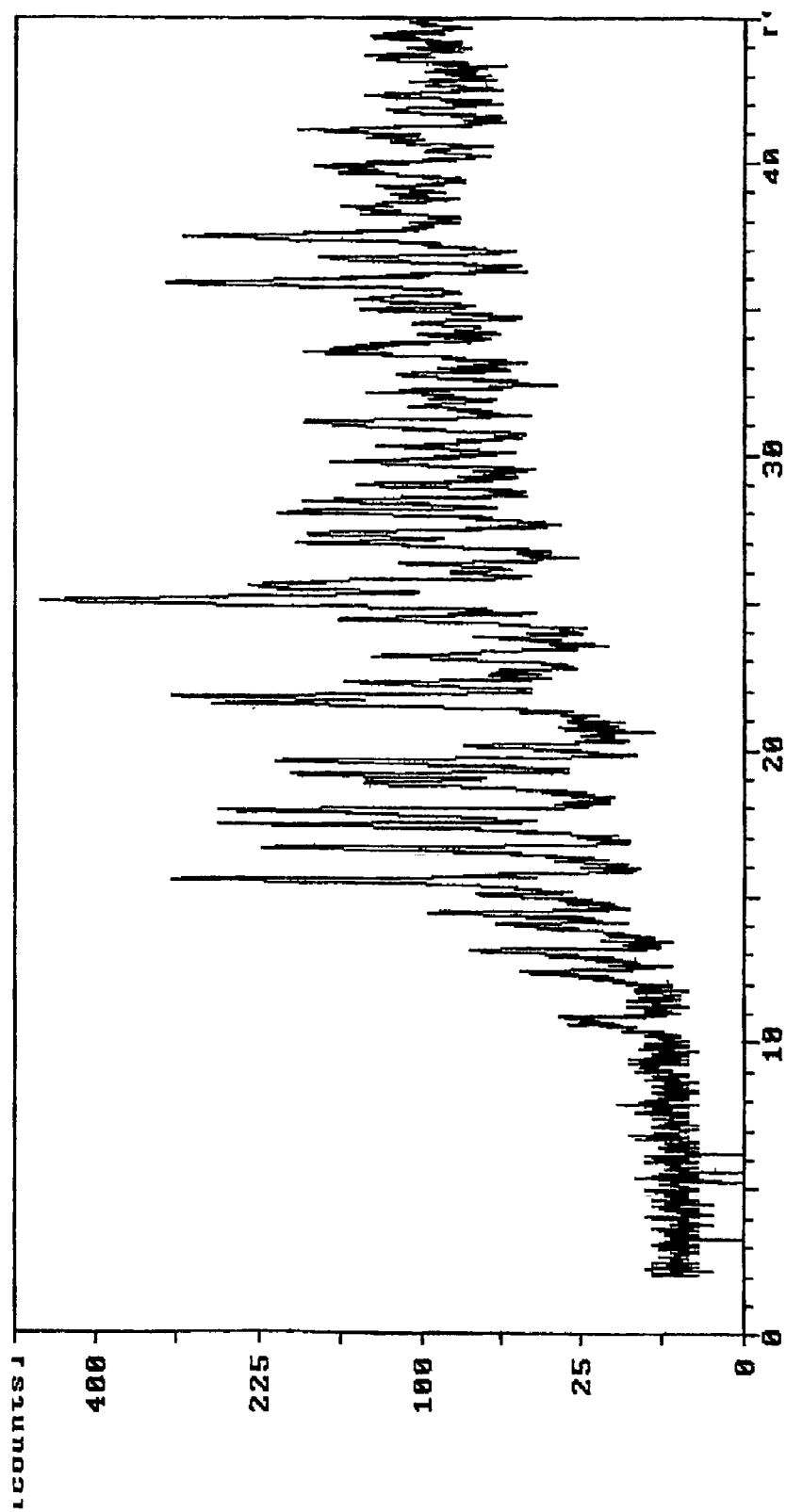
FIG. 21: Enlarged XRPD profile of complexes of the invention with dimethylformamide
Figure 22:
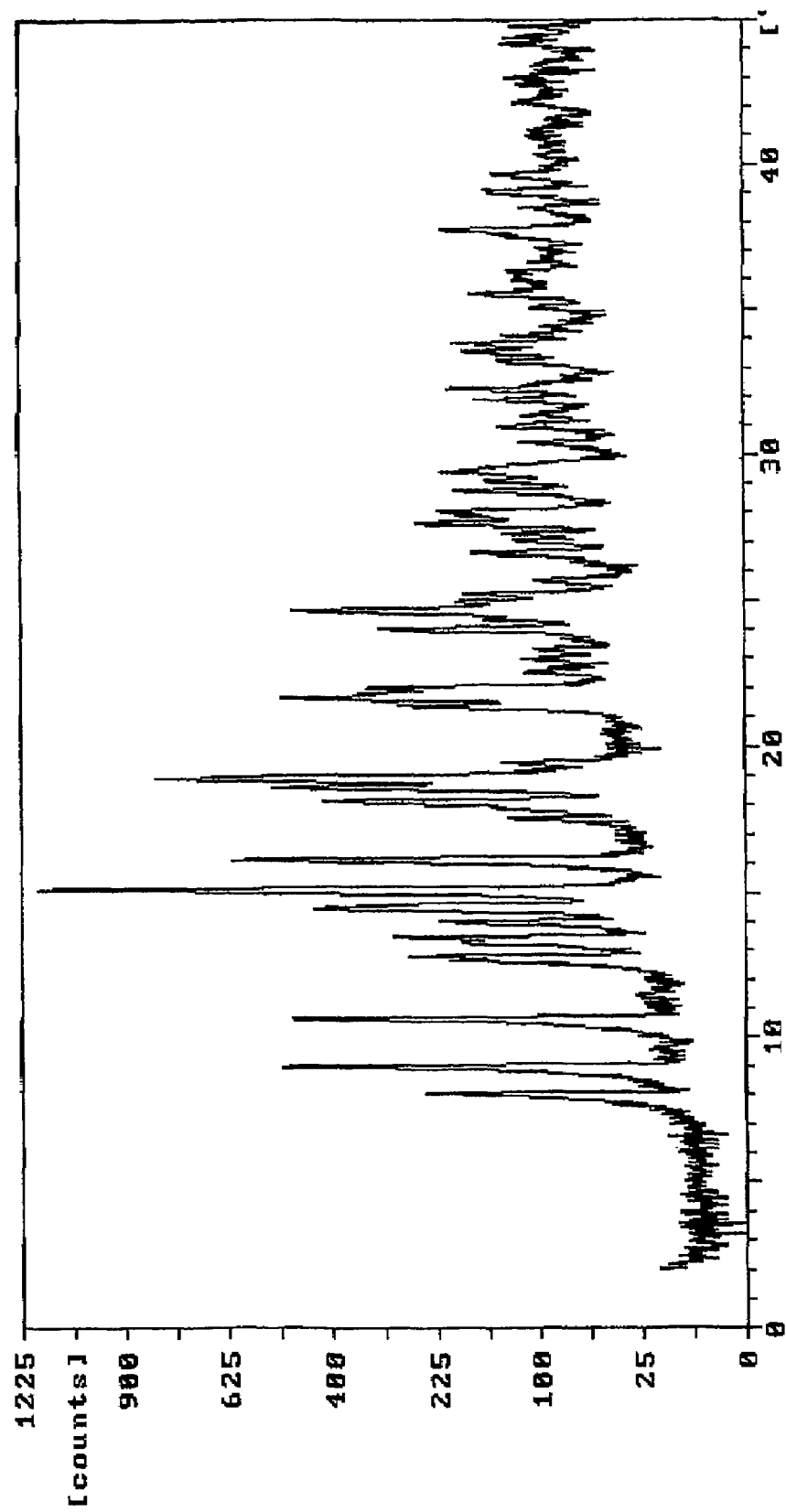
FIG. 22: Enlarged XRPD profile of complexes of the invention with butan-1-ol
Figure 23:
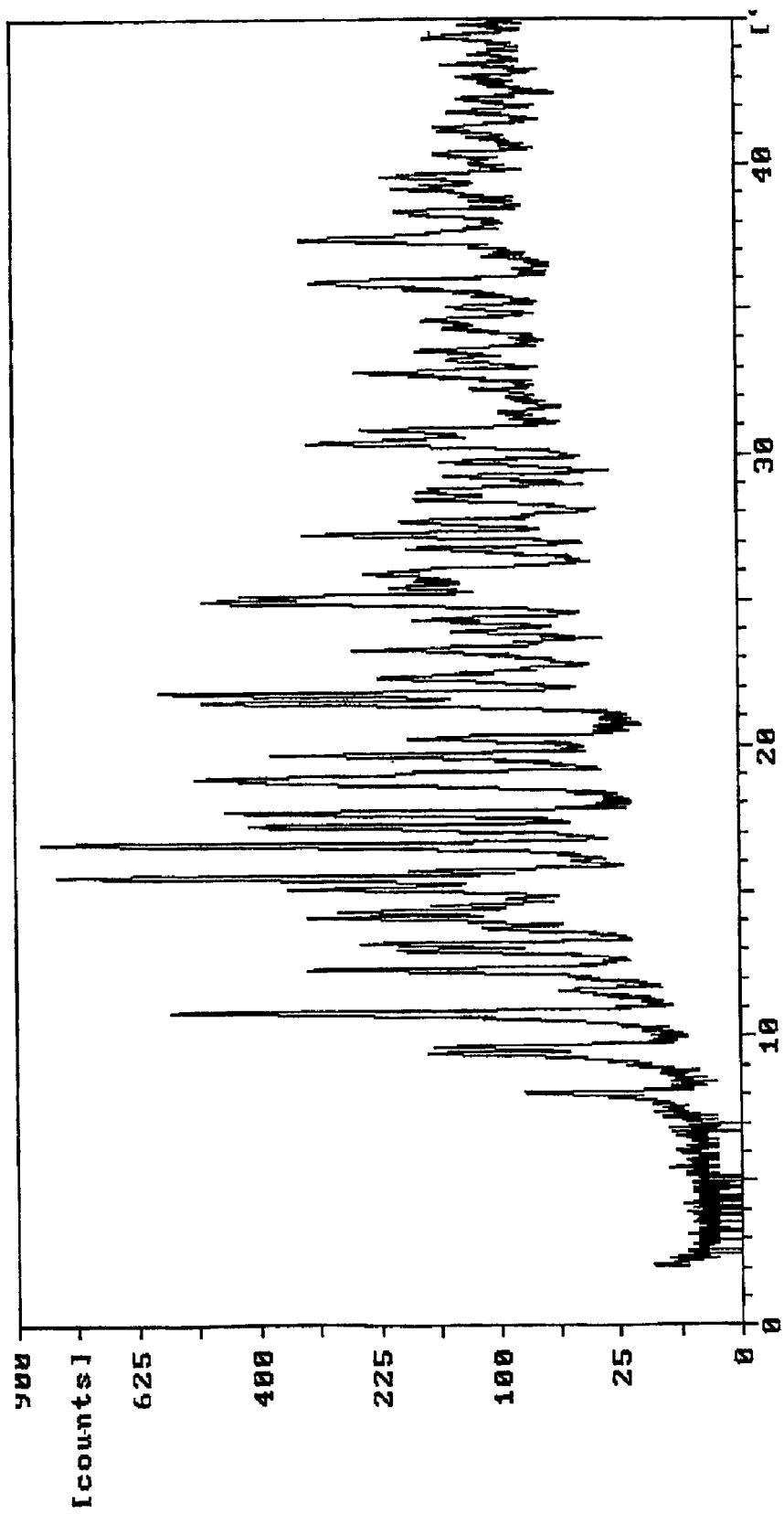
FIG. 23: Enlarged XRPD profile of complexes of the invention with methyl acetate
Figure 24:
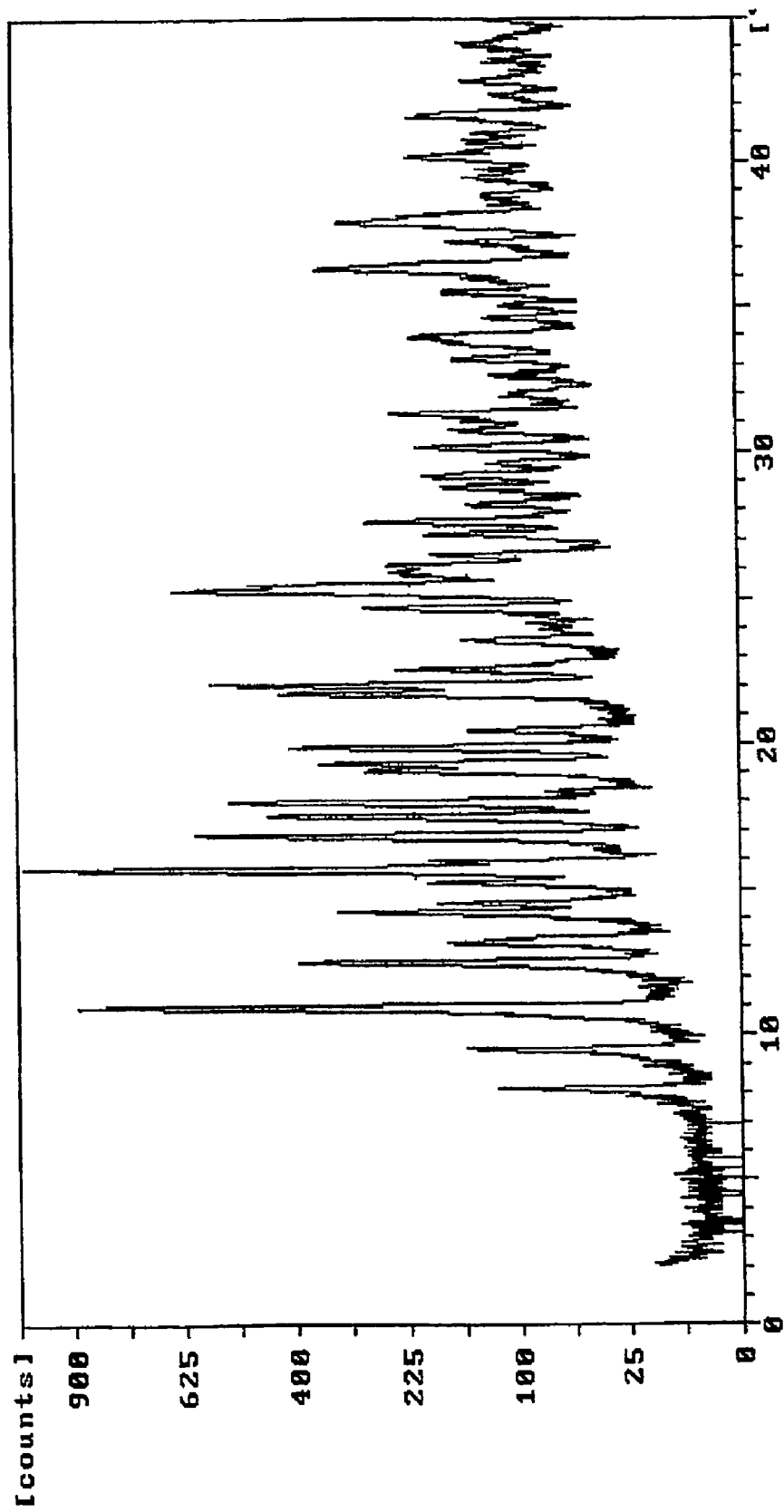
FIG. 24: Enlarged XRPD profile of complexes of the invention with acetic acid
Figure 25:
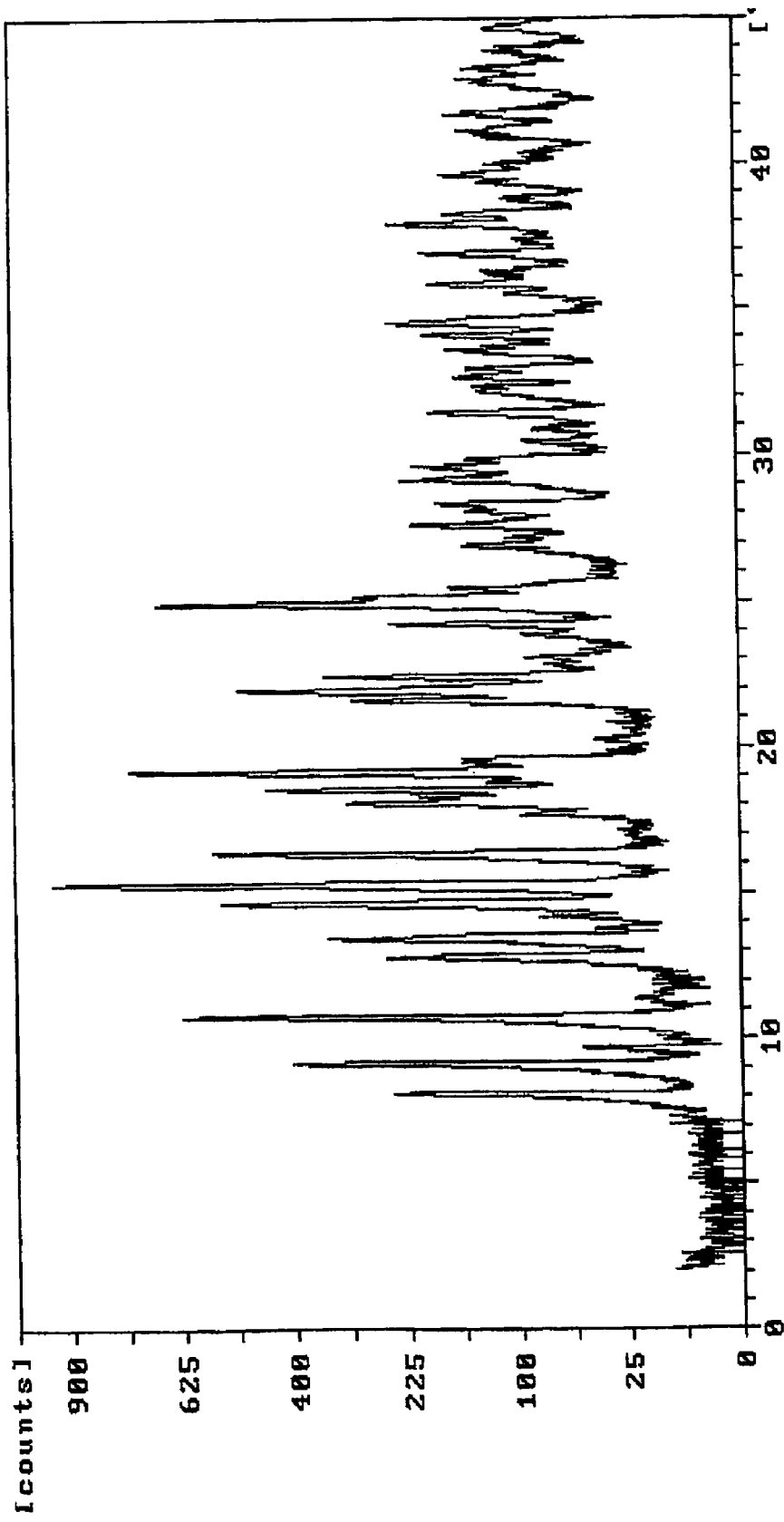
FIG. 25: Enlarged XRPD profile of complexes of the invention with propan-1-ol
Figure 26:
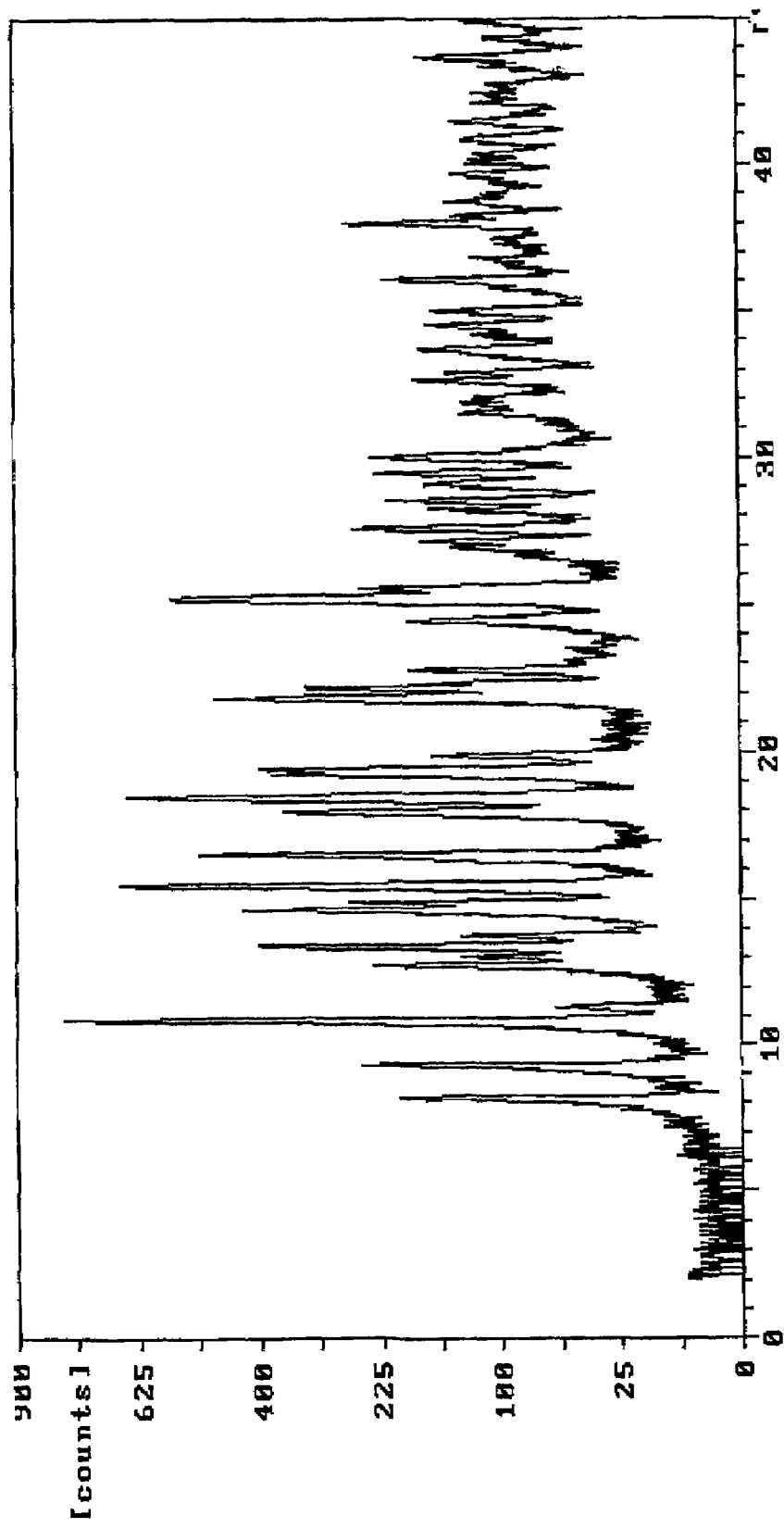
FIG. 26: Enlarged XRPD profile of complexes of the invention with ethanol
Figure 27:
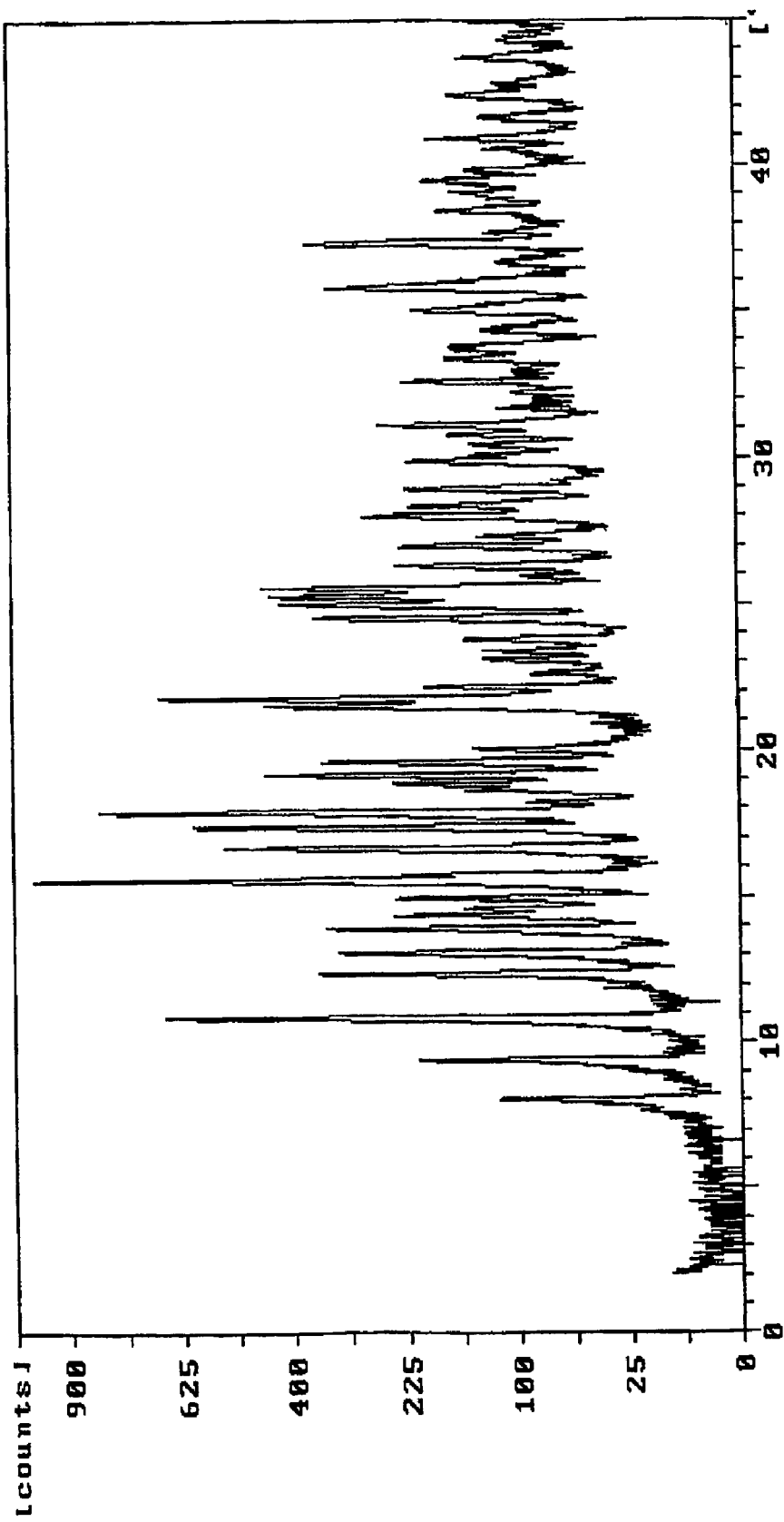
FIG. 27: Enlarged XRPD profile of complexes of the invention with ethyl formate
Figure 28:
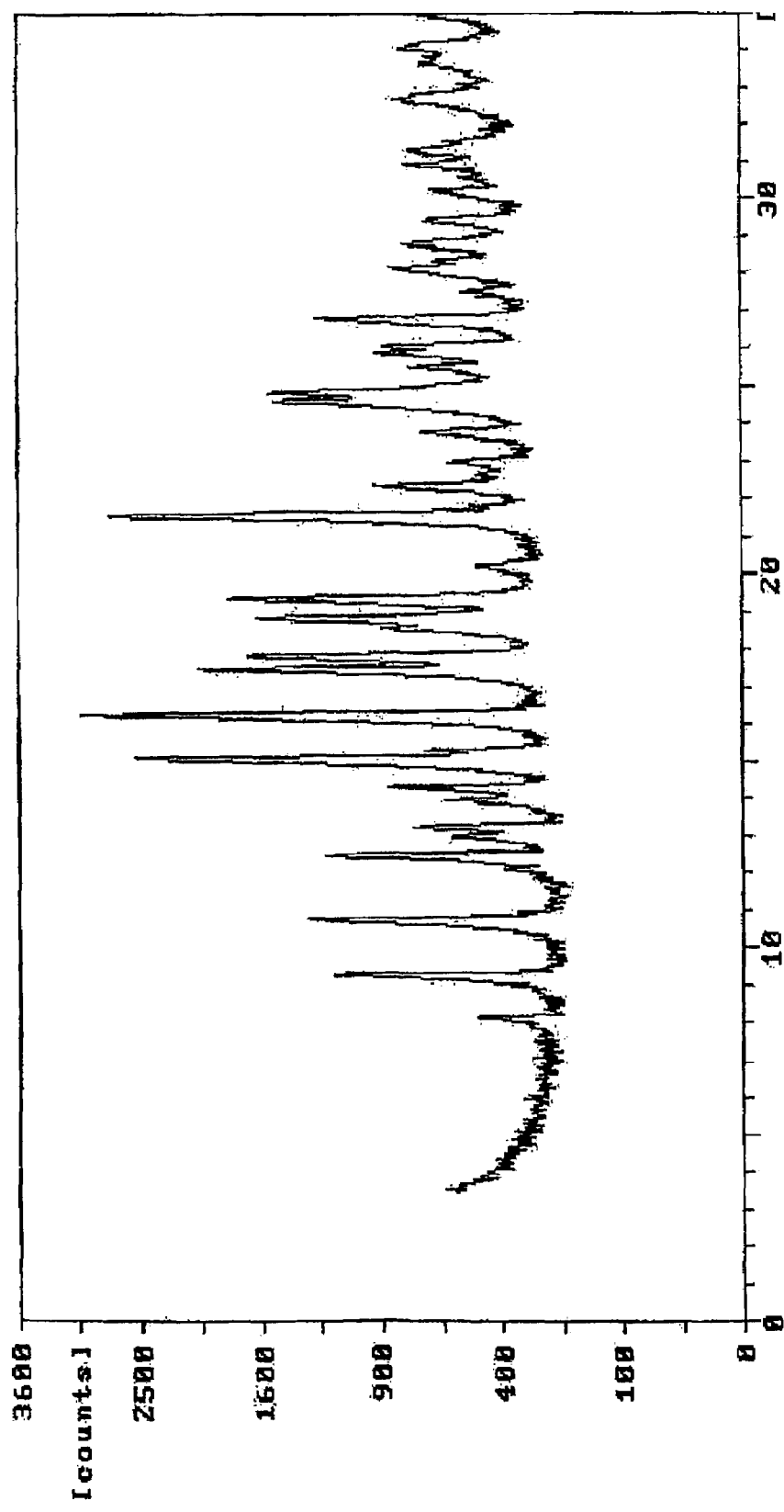
FIG. 28: Enlarged XRPD profile of complexes of the invention with 1,4-dioxane
Figure 29:
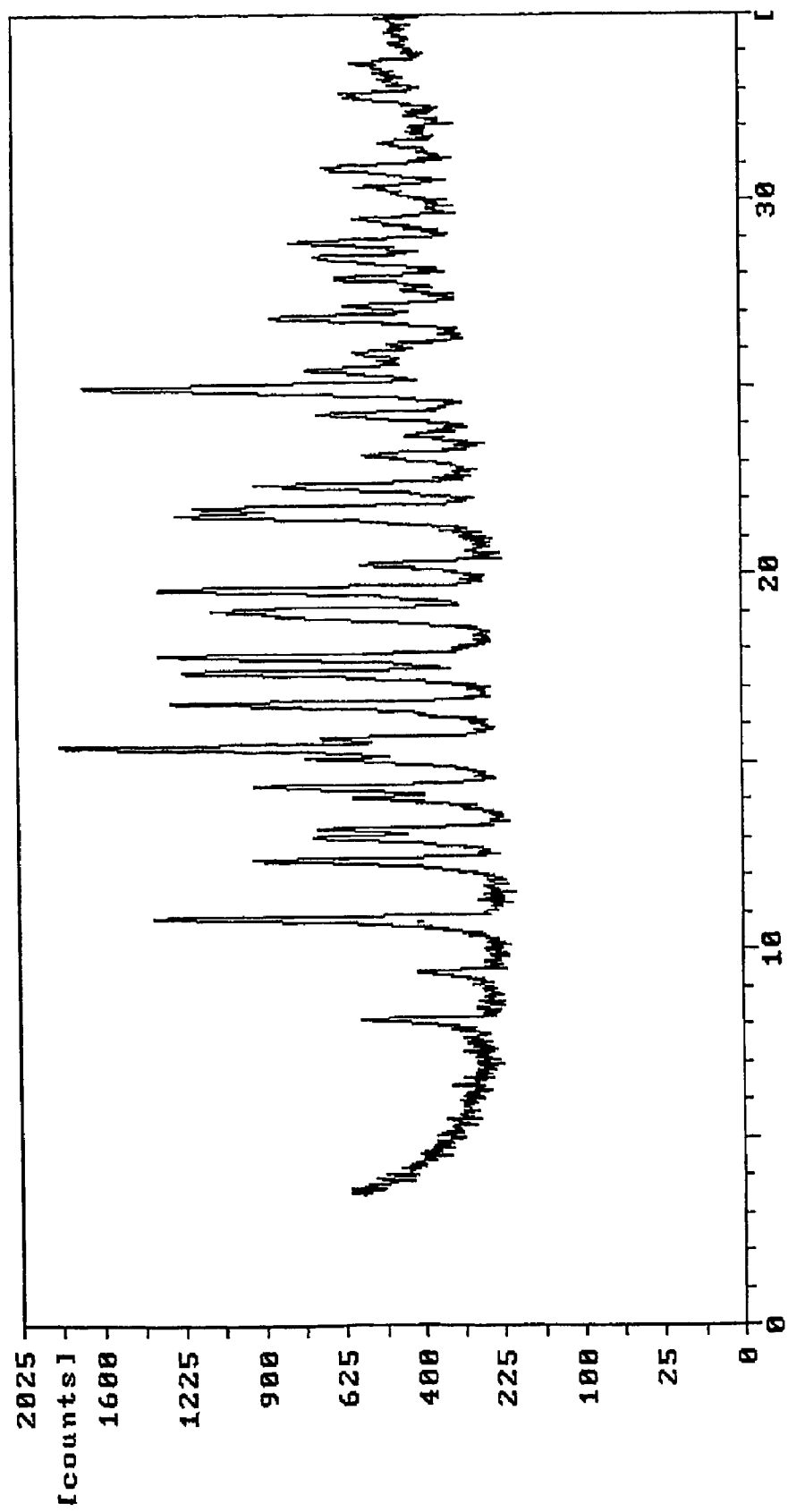
FIG. 29: Enlarged XRPD profile of complexes of the invention with dimethylsulphoxide
Figure 30:
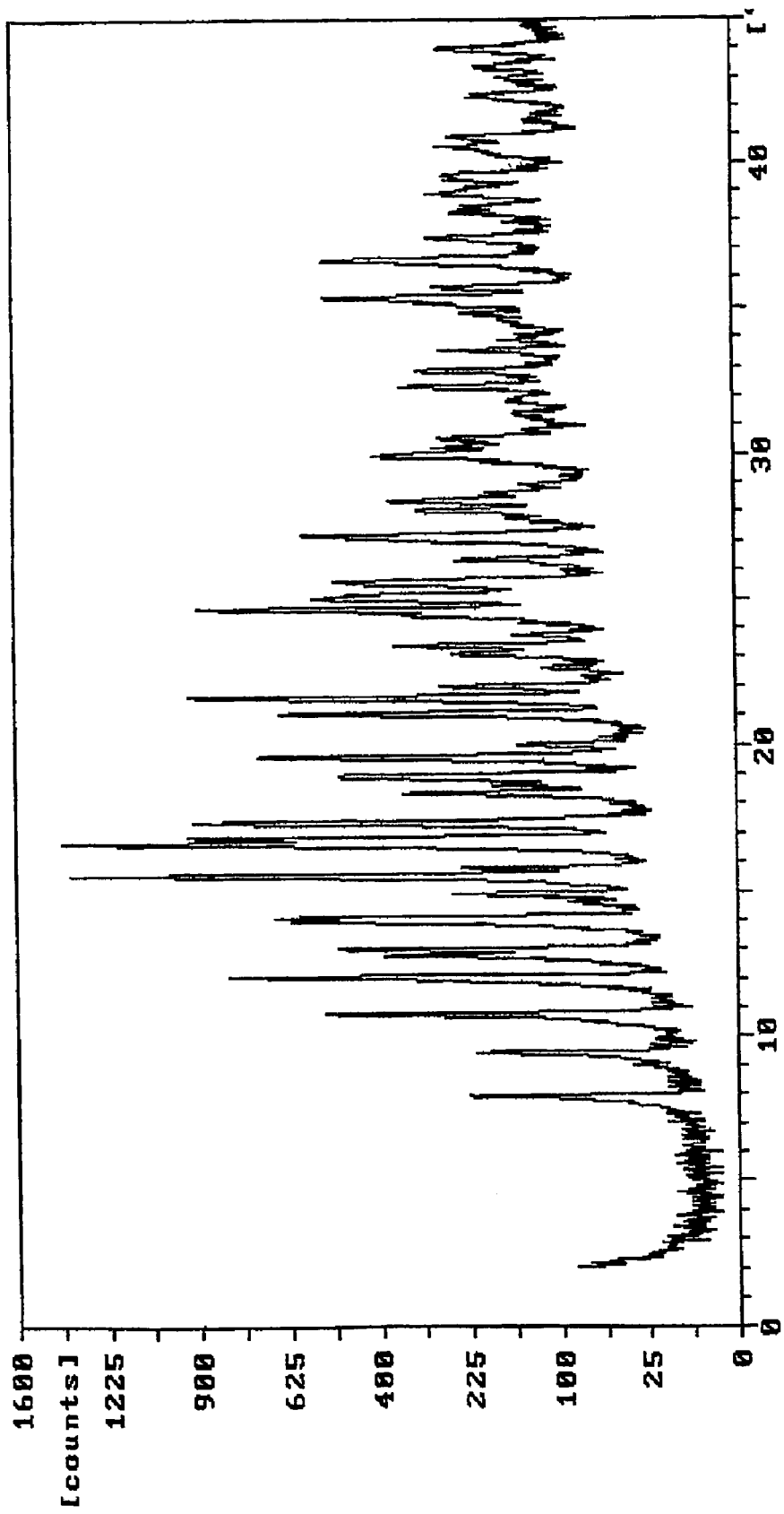
FIG. 30: Enlarged XRPD profile of complexes of the invention with N-methyl-2-pyrrolidinone
Figure 31:
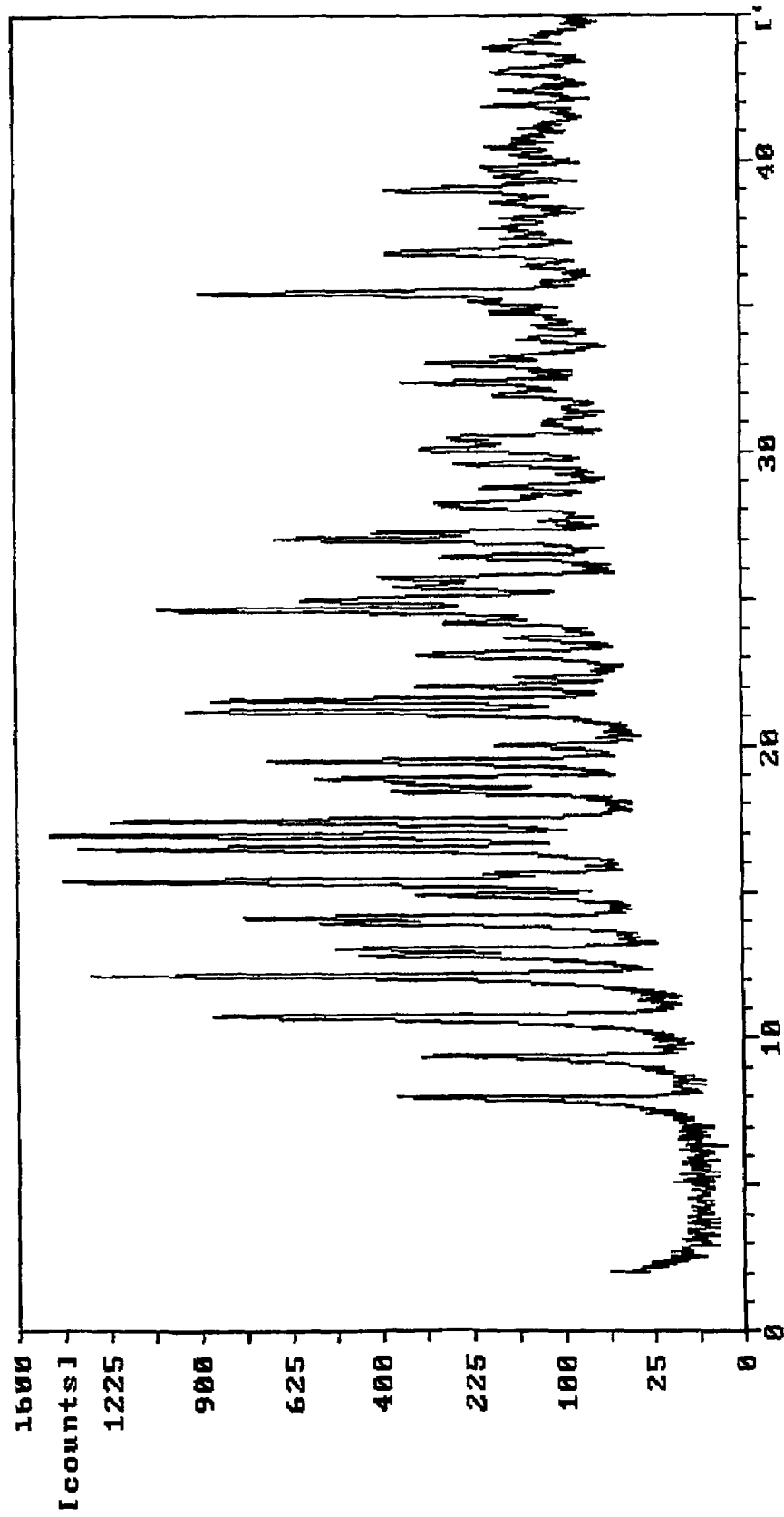
FIG. 31: Enlarged XRPD profile of complexes of the invention with dimethylacetamide
Figure 32:
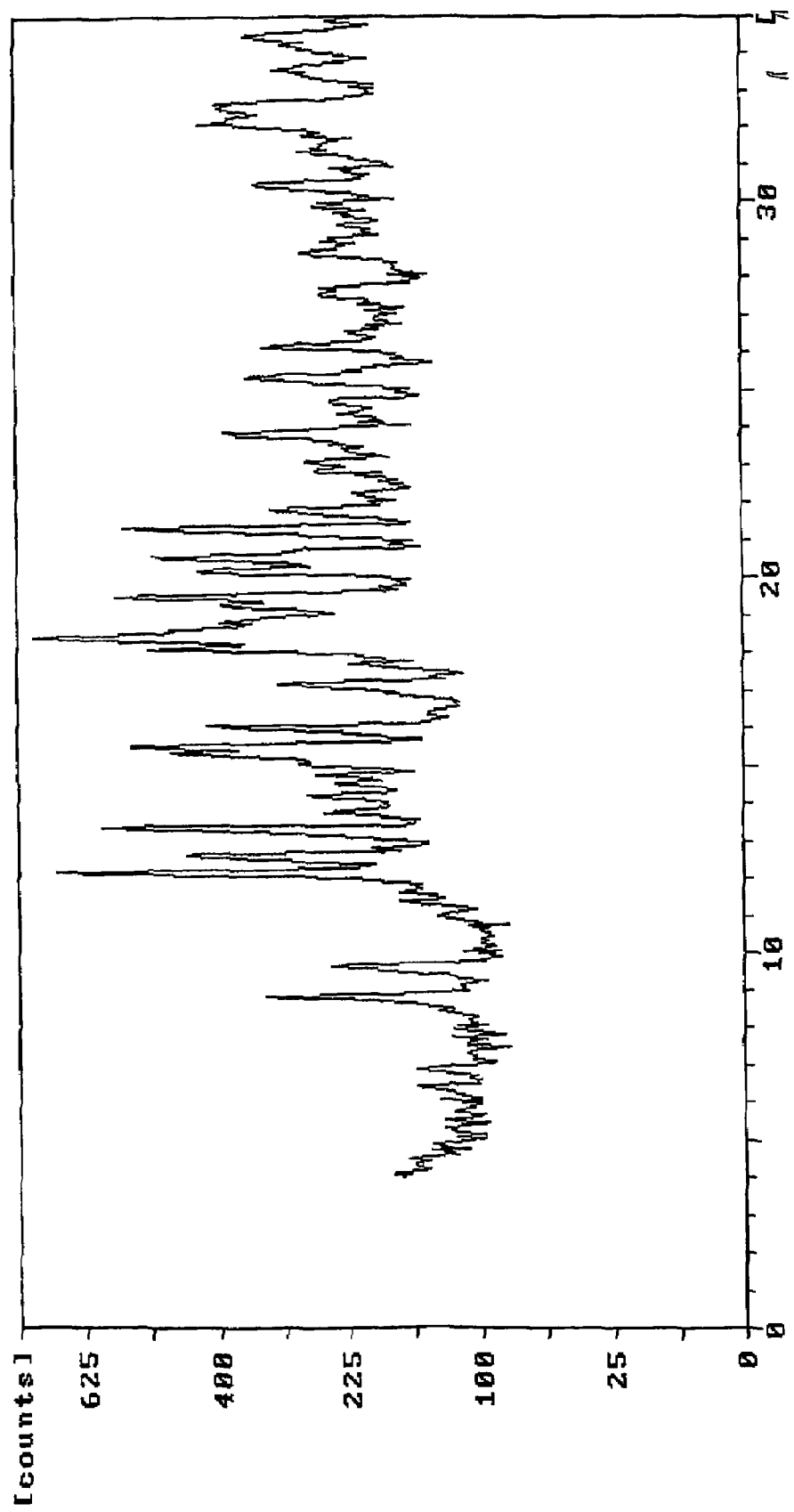
FIG. 32: Enlarged XRPD profile of complexes of the invention with water
Figure 33:
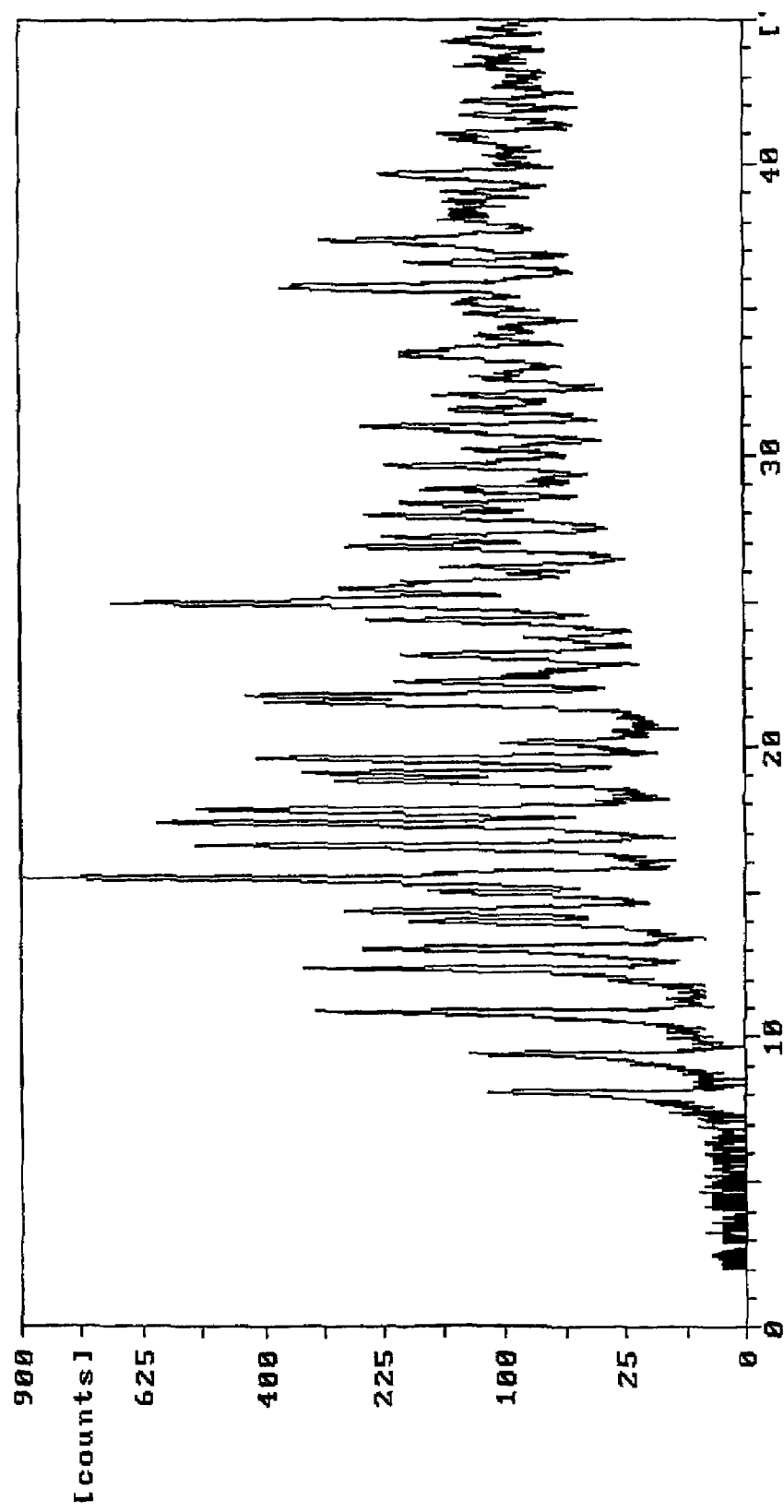
FIG. 33: Enlarged XRPD profile of complexes of the invention with cyclopentanone
Figure 34:
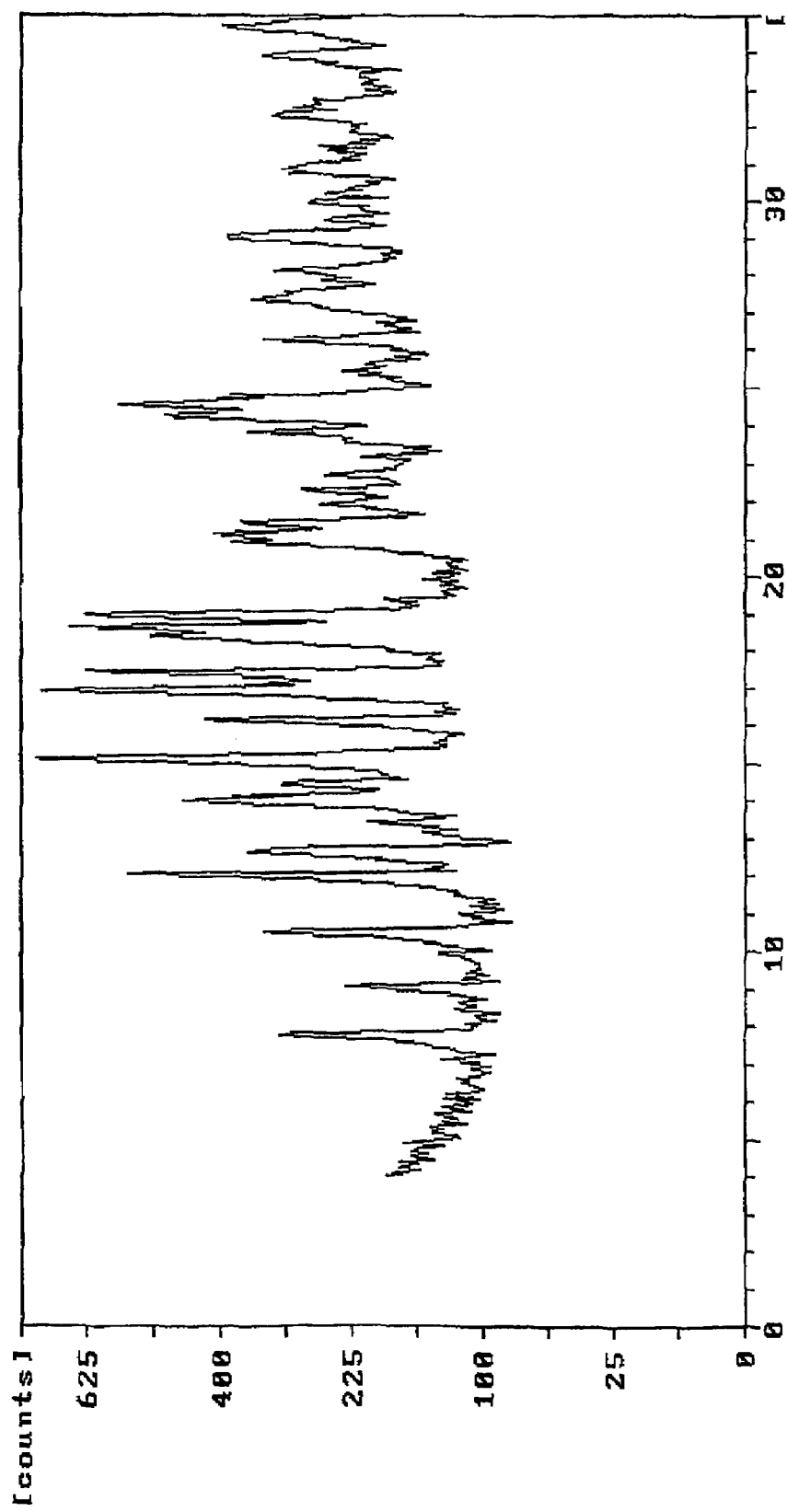
FIG. 34: Enlarged XRPD profile of complexes of the invention with ε-caprolactam.
Figure 35:
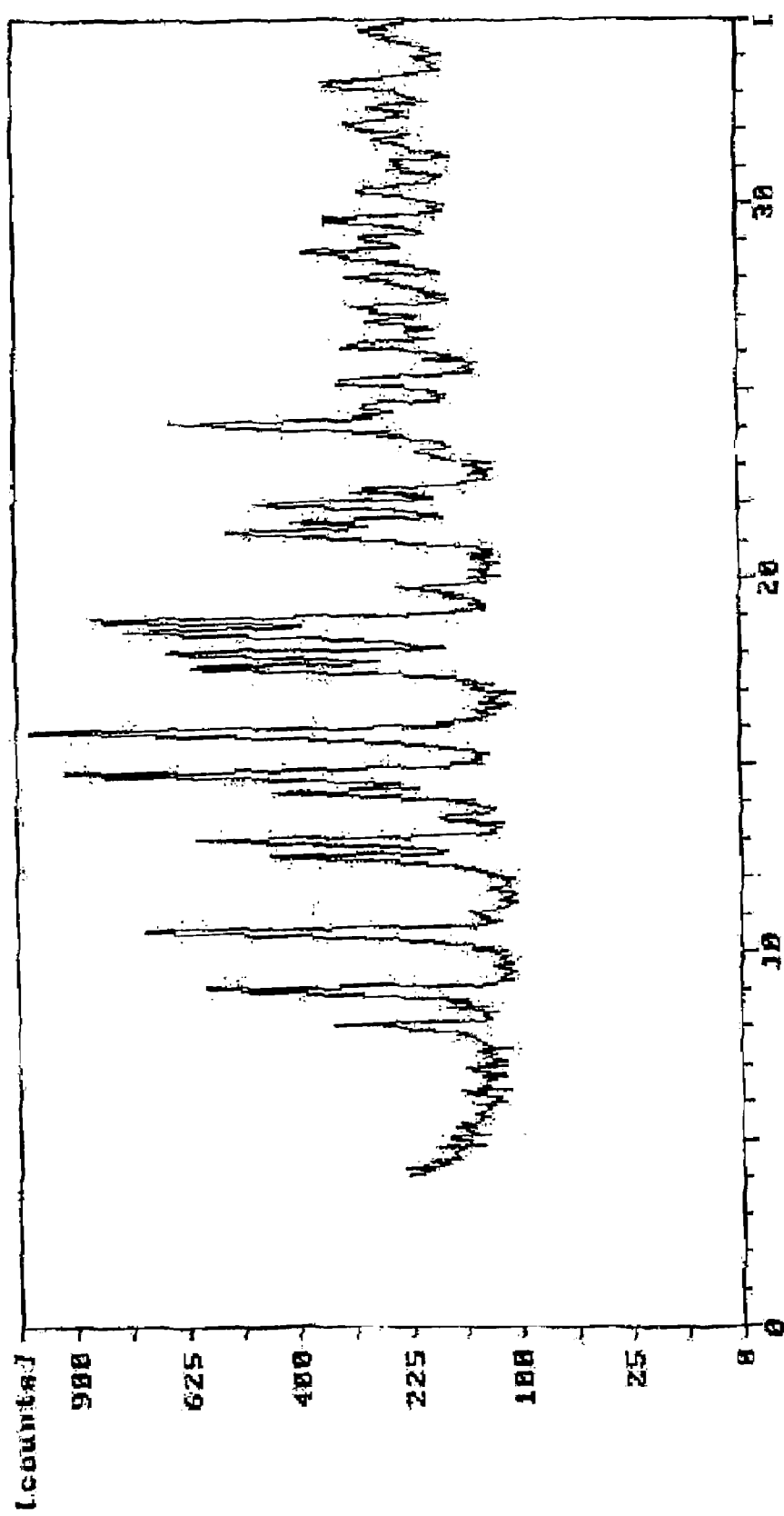
FIG. 35: Enlarged XRPD profile of complexes of the invention with t-butylamine.

The XRPD profiles of various complexes of the invention are provided in FIG. 4 and in detail in FIGS. 17-34.

The Raman spectra of various complexes of the invention are provided in FIGS. 9 to 16.

We also claim complexes of the invention substantially by reference to their XRPD profiles and/or their Raman spectra as shown in the Figures and Tables.

Example A

Dry Powder Composition Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone A dry powder formulation may be prepared as follows:

| | |
|---|---|
| 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with acetone prepared according to Example 1, MMD of 3 μm: | 0.20 mg |
| milled lactose (wherein not greater than 85% of particles have a MMD of 60-90 μm, and not less than 15% of particles have a MMD of less than 15 μm): | 12 mg |

A peelable blister strip containing 60 blisters each filled with a formulation as just described may be prepared.

Example B

Dry Powder Composition Containing 6α,9α-Difluoro-17α-[(2-furanylcarbonyl)oxy]-11β-hydroxy- 16α-methyl-3-oxo-androsta-1,4-diene-17β-carbothioic acid S-fluoromethyl ester complex with acetone and a tong acting β$_2$-adrenoreceptor agonist A dry powder formulation may be prepared as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone prepared according to Example 1, MMD of 3 μm: | 0.20 mg |
| Long-acting β$_2$-adrenoreceptor agonist (micronised to a MMD of 3 μm): | 0.02 mg |
| milled lactose (wherein not greater than 85% of particles have a MMD of 60-90 μm, and not less than 15% of particles have a MMD of less than 15 μm): | 12 mg |

A peelable blister strip containing 60 blisters each filled with a formulation as just described may be prepared.

Example C

Aerosol Formulation Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone Prepared According to Example 1, MMD of 3 μm An aluminium canister may be filled with a formulation as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone prepared according to Example 1, MMD of 3 μm: | 250 μg |
| 1,1,1,2-tetrafluoroethane: | to 50 μl |

(amounts per actuation)

in a total amount suitable for 120 actuations and the canister may be fitted with a metering valve adapted to dispense 50 μl per actuation.

Example D

Aerosol Formulation Containing 6α,9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone and a long acting β$_2$-adrenoreceptor agonist An aluminium canister may be filled with a formulation as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone prepared according to Example 1, MMD of 3 μm: | 250 μg |
| Long-acting β$_2$-adrenoreceptor agonist (micronised to a MMD of 3 μm): | 25 μg |
| 1,1,1,2-tetrafluoroethane: | to 50 μl |

(amounts per actuation)

in a total amount suitable for 120 actuations and the canister may be fitted with a metering valve adapted to dispense 50 μl per actuation.

Example E

Nasal Formulation Containing 6α,9α-Difluoro-17α-[(2-furanylcarbonyl)oxy]-11β-hydroxy-16α-methyl-3-oxo-androsta-1,4-diene-17β-carbothioic Acid S-Fluoromethyl Ester Complex with Acetone A formulation for intranasal delivery may be prepared as follows:

| | |
|---|---|
| 6α, 9α-Difluoro-17α-[(2-furanylcarbonyl)oxy]-11β-hydroxy-16α-methyl-3-oxo-androsta-1,4-diene-17β-carbothioic acid S-fluoromethyl ester complex with acetone prepared according to Example 1, MMD of 3 μm: | 10 mg |
| Polysorbate 20 | 0.8 mg |
| Sorbitan monolaurate | 0.09 mg |
| Sodium dihydrogen phosphate dihydrate | 94 mg |
| Dibasic sodium phosphate anhydrous | 17.5 mg |
| Sodium chloride | 48 mg |
| Demineralised water | to 10 ml |

The formulation may be fitted into a spraypump capable of delivering a plurality of metered doses (Valois).

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The patents and patent applications described in this application are herein incorporated by reference.

TABLE 2

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with acetone.

| Angle °2 Theta | Relative Intensity % |
|---|---|
| 9.5 | 3.3 |
| 10.9 | 26.6 |
| 12.4 | 13.1 |
| 13.1 | 23.9 |
| 14.1 | 21.7 |
| 14.5 | 21.7 |
| 15.1 | 18.9 |
| 15.7 | 100.0 |
| 16.8 | 75.6 |
| 17.4 | 35.5 |
| 17.9 | 50.1 |
| 18.3 | 5.5 |
| 18.9 | 28.6 |
| 19.3 | 32.0 |
| 19.8 | 54.0 |
| 20.3 | 18.2 |
| 21.6 | 41.8 |
| 22.0 | 62.2 |
| 22.4 | 31.5 |
| 22.7 | 13.6 |
| 23.3 | 16.0 |
| 23.6 | 14.2 |
| 24.0 | 7.2 |
| 24.7 | 23.1 |
| 25.1 | 64.6 |

TABLE 2-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with acetone.

| Angle °2 Theta | Relative Intensity % |
|---|---|
| 25.4 | 71.6 |
| 25.8 | 39.8 |
| 26.4 | 13.9 |
| 27.1 | 17.6 |
| 27.5 | 41.8 |
| 28.0 | 16.0 |
| 28.6 | 27.8 |
| 29.1 | 19.2 |
| 30.1 | 28.2 |
| 30.5 | 20.2 |
| 31.2 | 25.4 |
| 31.7 | 11.2 |
| 32.5 | 12.5 |
| 32.9 | 18.2 |
| 33.6 | 15.7 |
| 33.9 | 15.7 |
| 34.3 | 14.5 |
| 34.8 | 13.9 |
| 35.3 | 22.0 |
| 35.7 | 15.1 |
| 36.1 | 41.3 |
| 37.0 | 15.7 |
| 37.6 | 40.8 |
| 38.7 | 20.6 |
| 39.0 | 15.4 |
| 39.6 | 19.9 |
| 40.0 | 23.1 |
| 40.8 | 11.5 |
| 41.2 | 16.0 |
| 41.5 | 13.6 |
| 42.0 | 12.8 |
| 42.8 | 13.6 |
| 43.6 | 9.5 |
| 44.0 | 16.0 |
| 44.7 | 13.4 |

TABLE 3

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with methylethylketone.

| Angle °2 Theta | Relative Intensity % |
|---|---|
| 7.3 | 4.2 |
| 8.0 | 20.0 |
| 8.5 | 5.7 |
| 9.3 | 16.9 |
| 9.8 | 14.1 |
| 10.8 | 71.0 |
| 11.2 | 8.2 |
| 11.8 | 11.8 |
| 12.4 | 40.6 |
| 13.1 | 53.0 |
| 13.5 | 7.8 |
| 13.9 | 39.4 |
| 14.4 | 35.9 |
| 15.0 | 35.9 |
| 15.5 | 100.0 |
| 16.1 | 16.9 |
| 16.6 | 67.4 |
| 17.3 | 55.6 |
| 17.8 | 69.8 |
| 18.6 | 19.8 |

TABLE 3-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with methylethylketone.

| Angle °2 Theta | Relative Intensity % |
|---|---|
| 18.8 | 32.8 |
| 19.1 | 31.0 |
| 19.6 | 47.4 |
| 20.0 | 18.1 |
| 20.3 | 6.8 |
| 20.8 | 6.7 |
| 21.5 | 45.2 |
| 21.7 | 60.8 |
| 22.2 | 24.4 |
| 22.5 | 22.6 |
| 23.1 | 20.5 |
| 23.3 | 14.9 |
| 23.7 | 14.8 |
| 24.5 | 26.7 |
| 25.0 | 51.7 |
| 25.2 | 53.5 |
| 25.5 | 43.6 |
| 25.9 | 12.0 |
| 26.2 | 15.2 |
| 26.9 | 24.6 |
| 27.2 | 28.6 |
| 27.9 | 28.2 |
| 28.4 | 22.6 |
| 28.9 | 28.4 |
| 29.8 | 24.7 |
| 30.1 | 19.2 |
| 30.4 | 20.5 |
| 31.0 | 31.6 |
| 31.6 | 12.5 |
| 32.2 | 18.0 |
| 32.5 | 18.7 |
| 33.3 | 20.3 |
| 33.6 | 23.3 |
| 33.9 | 14.4 |
| 34.2 | 14.2 |
| 34.5 | 13.7 |
| 34.9 | 18.6 |
| 35.2 | 18.7 |
| 35.7 | 38.3 |
| 36.6 | 17.1 |
| 37.3 | 48.4 |
| 38.3 | 21.1 |
| 39.0 | 15.5 |
| 39.5 | 21.8 |
| 39.8 | 25.4 |
| 40.4 | 14.7 |
| 41.0 | 16.3 |
| 41.7 | 15.9 |
| 42.3 | 17.8 |
| 42.7 | 12.9 |
| 43.0 | 11.2 |
| 43.6 | 19.8 |
| 44.2 | 13.6 |

TABLE 4

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with propan-2-ol.

| Angle °2 Theta | Relative Intensity % |
|---|---|
| 8.1 | 8.0 |
| 9.2 | 100.0 |

TABLE 4-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with propan-2-ol.

| Angle °2 Theta | Relative Intensity % |
|---|---|
| 10.8 | 19.4 |
| 11.2 | 0.6 |
| 12.7 | 5.1 |
| 13.0 | 7.3 |
| 13.3 | 5.9 |
| 13.7 | 9.2 |
| 14.5 | 8.1 |
| 14.8 | 7.6 |
| 15.3 | 20.8 |
| 16.4 | 18.9 |
| 17.9 | 5.6 |
| 18.3 | 10.9 |
| 18.5 | 19.6 |
| 19.0 | 7.4 |
| 19.3 | 15.9 |
| 19.8 | 7.8 |
| 21.6 | 9.7 |
| 22.1 | 14.7 |
| 22.7 | 16.4 |
| 22.9 | 1.6 |
| 23.5 | 1.3 |
| 24.2 | 4.8 |
| 24.5 | 3.0 |
| 24.9 | 8.7 |
| 25.1 | 11.6 |
| 25.5 | 4.3 |
| 26.4 | 1.4 |
| 26.9 | 4.8 |
| 27.3 | 4.5 |
| 27.8 | 7.5 |
| 28.4 | 4.6 |
| 28.8 | 2.5 |
| 29.2 | 5.1 |
| 29.8 | 12.0 |
| 31.0 | 2.0 |
| 31.5 | 2.8 |
| 31.8 | 2.5 |
| 32.5 | 5.1 |
| 32.8 | 3.1 |
| 33.4 | 6.4 |
| 34.0 | 3.1 |
| 34.3 | 5.2 |
| 34.9 | 5.1 |
| 35.4 | 1.7 |
| 35.9 | 3.3 |
| 36.3 | 2.6 |
| 37.2 | 2.6 |
| 37.8 | 6.5 |
| 38.4 | 3.8 |
| 38.9 | 2.1 |
| 39.5 | 3.3 |
| 40.2 | 2.8 |
| 40.6 | 2.7 |
| 41.5 | 4.6 |
| 42.2 | 3.6 |
| 42.4 | 4.2 |
| 43.1 | 3.5 |
| 43.4 | 4.5 |
| 44.0 | 2.5 |
| 44.6 | 2.2 |

TABLE 5

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with tetrahydrofuran.

| Angle °2 Theta | Relative Intensity % |
|---|---|
| 2.1 | 11.1 |
| 8.1 | 15.1 |
| 9.5 | 28.2 |
| 9.7 | 23.3 |
| 10.9 | 78.1 |
| 11.6 | 8.9 |
| 12.4 | 39.0 |
| 13.2 | 35.8 |
| 13.7 | 16.9 |
| 14.1 | 21.1 |
| 14.3 | 32.1 |
| 15.1 | 47.5 |
| 15.5 | 100.0 |
| 16.7 | 88.7 |
| 17.3 | 69.2 |
| 17.8 | 68.6 |
| 18.8 | 73.0 |
| 19.1 | 44.4 |
| 19.7 | 57.3 |
| 20.2 | 21.4 |
| 21.5 | 58.8 |
| 21.8 | 65.5 |
| 22.4 | 28.9 |
| 23.3 | 36.6 |
| 23.7 | 13.1 |
| 24.0 | 17.4 |
| 24.4 | 23.6 |
| 25.0 | 58.8 |
| 25.5 | 25.5 |
| 25.9 | 31.0 |
| 26.2 | 24.5 |
| 26.6 | 10.7 |
| 26.9 | 24.8 |
| 27.3 | 30.3 |
| 27.9 | 21.1 |
| 28.5 | 25.2 |
| 28.9 | 20.5 |
| 29.3 | 12.2 |
| 29.8 | 19.1 |
| 30.4 | 31.7 |
| 30.9 | 21.4 |
| 31.5 | 14.6 |
| 32.2 | 15.3 |
| 32.8 | 20.8 |
| 33.6 | 21.4 |
| 34.3 | 19.7 |
| 34.6 | 16.4 |
| 35.1 | 14.6 |
| 36.0 | 28.9 |
| 36.8 | 15.3 |
| 37.4 | 26.1 |
| 38.1 | 14.1 |
| 38.4 | 18.2 |
| 39.2 | 15.6 |
| 39.7 | 25.2 |
| 40.5 | 18.5 |
| 41.3 | 16.4 |
| 41.9 | 12.7 |
| 42.3 | 13.4 |
| 43.1 | 12.7 |
| 43.5 | 11.1 |
| 43.9 | 12.2 |
| 44.5 | 18.2 |

TABLE 6

XRPD characteristic angles and relative intensities for 6α,9α-Difluoro-17α-[(2-furanylcarbonyl)oxy]-11β-hydroxy-16α-methyl-3-oxo-androsta-1,4-diene- 17β-carbothioic acid S-fluoromethyl ester, complex with dimethylformamide.

| Angle °2 Theta | Relative Intensity % |
|---|---|
| 7.9 | 1.1 |
| 9.1 | 0.9 |
| 10.8 | 5.8 |
| 12.4 | 7.7 |
| 13.1 | 12.1 |
| 14.0 | 12.1 |
| 14.4 | 17.7 |
| 15.5 | 65.6 |
| 16.6 | 40.8 |
| 17.4 | 48.9 |
| 17.9 | 56.9 |
| 18.8 | 28.8 |
| 19.1 | 40.8 |
| 19.6 | 37.9 |
| 20.1 | 14.4 |
| 21.5 | 56.9 |
| 21.8 | 65.6 |
| 22.3 | 31.9 |
| 22.6 | 10.8 |
| 23.1 | 24.1 |
| 23.8 | 10.8 |
| 24.4 | 31.4 |
| 25.0 | 100.0 |
| 25.6 | 38.5 |
| 26.0 | 16.6 |
| 26.3 | 24.1 |
| 27.0 | 36.8 |
| 27.2 | 36.8 |
| 28.0 | 36.2 |
| 28.4 | 29.8 |
| 29.0 | 27.9 |
| 29.7 | 33.5 |
| 30.2 | 22.3 |
| 31.1 | 37.9 |
| 31.6 | 19.3 |
| 32.1 | 23.6 |
| 32.7 | 21.4 |
| 33.4 | 39.1 |
| 33.7 | 25.0 |
| 34.5 | 18.5 |
| 34.9 | 25.0 |
| 35.3 | 27.4 |
| 35.8 | 61.2 |
| 36.7 | 34.0 |
| 37.4 | 57.6 |
| 38.2 | 25.9 |
| 38.4 | 28.3 |
| 39.1 | 25.5 |
| 39.6 | 28.8 |
| 39.9 | 32.4 |
| 40.4 | 17.7 |
| 41.1 | 37.3 |
| 41.8 | 24.5 |
| 42.3 | 26.4 |
| 42.7 | 18.1 |
| 43.6 | 24.1 |
| 44.4 | 25.0 |

TABLE 7

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with butan-1-ol.

| Angle °2 Theta | Relative Intensity % |
|---|---|
| 8.0 | 21.5 |
| 9.0 | 46.4 |
| 9.6 | 1.0 |
| 10.6 | 45.5 |
| 11.4 | 1.7 |
| 12.7 | 22.3 |
| 13.2 | 15.7 |
| 13.4 | 27.2 |
| 14.0 | 18.4 |
| 14.4 | 35.0 |
| 15.1 | 100.0 |
| 16.1 | 52.9 |
| 17.5 | 11.0 |
| 17.8 | 11.0 |
| 18.1 | 38.0 |
| 18.6 | 44.3 |
| 18.8 | 77.0 |
| 19.0 | 52.0 |
| 19.4 | 12.4 |
| 21.3 | 25.6 |
| 21.6 | 43.9 |
| 21.9 | 27.8 |
| 22.6 | 10.0 |
| 22.9 | 9.4 |
| 23.3 | 8.9 |
| 24.0 | 28.2 |
| 24.6 | 40.7 |
| 25.0 | 17.1 |
| 25.2 | 15.2 |
| 25.7 | 8.1 |
| 26.6 | 15.7 |
| 27.0 | 11.2 |
| 27.6 | 21.2 |
| 28.0 | 20.3 |
| 28.7 | 16.4 |
| 29.1 | 14.2 |
| 29.4 | 15.7 |
| 30.4 | 9.4 |
| 30.9 | 11.4 |
| 31.3 | 8.9 |
| 31.9 | 14.0 |
| 32.2 | 17.9 |
| 33.2 | 12.4 |
| 33.5 | 16.6 |
| 33.8 | 16.4 |
| 34.1 | 10.4 |
| 35.0 | 9.0 |
| 35.5 | 13.5 |
| 36.3 | 10.4 |
| 37.1 | 7.8 |
| 37.7 | 17.9 |
| 38.5 | 9.4 |
| 39.0 | 14.2 |
| 39.6 | 13.1 |
| 40.3 | 8.0 |
| 41.1 | 8.3 |
| 41.6 | 7.6 |
| 42.1 | 10.6 |
| 43.0 | 10.6 |
| 43.4 | 8.7 |
| 44.1 | 9.4 |

TABLE 8

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with methyl acetate.

| Angle °2 Theta | Relative Intensity % |
|---|---|
| 5.4 | 0.3 |
| 8.1 | 10.0 |
| 9.4 | 17.2 |
| 9.7 | 17.8 |
| 10.8 | 70.0 |
| 11.6 | 5.8 |
| 12.3 | 39.0 |
| 12.9 | 23.3 |
| 13.2 | 29.8 |
| 13.7 | 13.6 |
| 14.0 | 35.1 |
| 14.7 | 11.6 |
| 15.1 | 38.5 |
| 15.5 | 100.0 |
| 15.7 | 20.0 |
| 16.6 | 97.9 |
| 17.2 | 44.9 |
| 17.7 | 57.6 |
| 18.7 | 46.8 |
| 18.9 | 52.3 |
| 19.6 | 47.3 |
| 20.2 | 19.6 |
| 21.4 | 58.7 |
| 21.8 | 71.2 |
| 22.3 | 26.8 |
| 23.3 | 31.8 |
| 23.9 | 16.1 |
| 24.3 | 19.6 |
| 24.9 | 59.8 |
| 25.4 | 26.1 |
| 25.9 | 28.3 |
| 26.0 | 21.9 |
| 26.8 | 19.0 |
| 27.2 | 41.2 |
| 27.7 | 23.3 |
| 28.4 | 22.2 |
| 28.7 | 20.9 |
| 29.2 | 16.9 |
| 29.7 | 18.4 |
| 30.3 | 37.2 |
| 30.8 | 30.6 |
| 31.4 | 11.3 |
| 31.9 | 10.2 |
| 32.1 | 13.6 |
| 32.7 | 30.2 |
| 33.2 | 17.2 |
| 33.5 | 19.6 |
| 34.3 | 17.5 |
| 34.6 | 18.4 |
| 35.0 | 17.5 |
| 35.9 | 37.2 |
| 37.3 | 41.2 |
| 38.3 | 23.6 |
| 39.1 | 20.3 |
| 39.5 | 25.4 |
| 40.3 | 19.3 |
| 41.2 | 18.4 |
| 41.8 | 16.6 |
| 42.3 | 16.1 |
| 43.0 | 14.4 |
| 43.4 | 15.8 |
| 44.4 | 19.0 |

TABLE 9

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with acetic acid.

| Angle °2 Theta | Relative Intensity % |
|---|---|
| 8.2 | 11.2 |
| 9.5 | 12.3 |
| 11.0 | 80.6 |
| 12.5 | 34.8 |
| 13.2 | 16.6 |
| 14.2 | 23.8 |
| 14.5 | 17.6 |
| 15.2 | 18.6 |
| 15.7 | 100.0 |
| 16.8 | 57.0 |
| 17.5 | 42.1 |
| 18.0 | 46.7 |
| 18.3 | 5.9 |
| 19.1 | 25.6 |
| 19.3 | 32.3 |
| 19.9 | 37.1 |
| 20.5 | 13.9 |
| 21.7 | 39.4 |
| 22.1 | 48.4 |
| 22.6 | 20.3 |
| 23.6 | 14.1 |
| 24.7 | 26.9 |
| 25.3 | 61.2 |
| 25.5 | 45.8 |
| 25.8 | 20.0 |
| 26.2 | 23.2 |
| 26.5 | 18.1 |
| 27.2 | 18.4 |
| 27.6 | 25.9 |
| 28.2 | 13.2 |
| 28.8 | 15.3 |
| 29.1 | 17.6 |
| 29.6 | 11.5 |
| 30.2 | 19.2 |
| 30.7 | 14.1 |
| 31.3 | 19.7 |
| 31.9 | 9.5 |
| 32.6 | 9.6 |
| 33.2 | 14.8 |
| 34.0 | 18.6 |
| 34.6 | 11.0 |
| 35.0 | 9.6 |
| 35.4 | 16.3 |
| 35.9 | 12.1 |
| 36.3 | 33.4 |
| 37.2 | 14.1 |
| 37.8 | 30.2 |
| 38.2 | 17.3 |
| 38.8 | 11.9 |
| 39.4 | 13.9 |
| 40.1 | 18.9 |
| 40.7 | 12.8 |
| 41.0 | 12.3 |
| 41.7 | 17.3 |
| 42.3 | 10.6 |
| 42.8 | 12.8 |
| 43.5 | 10.4 |
| 44.1 | 13.0 |

TABLE 10

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with propan-1-ol.

Relative

| Angle °2 Theta | Intensity % |
|---|---|
| 3.7 | 0.1 |
| 8.1 | 26.3 |
| 9.1 | 43.1 |
| 9.7 | 5.1 |
| 10.8 | 62.5 |
| 11.4 | 1.5 |
| 12.7 | 26.7 |
| 13.4 | 36.2 |
| 13.8 | 4.1 |
| 14.2 | 7.5 |
| 14.6 | 57.5 |
| 15.3 | 100.0 |
| 16.3 | 58.0 |
| 17.0 | 2.3 |
| 17.7 | 9.4 |
| 18.0 | 31.6 |
| 18.5 | 46.2 |
| 19.1 | 77.9 |
| 19.6 | 14.9 |
| 20.2 | 3.6 |
| 21.6 | 32.0 |
| 21.9 | 53.1 |
| 22.4 | 34.6 |
| 22.8 | 7.7 |
| 23.0 | 8.1 |
| 23.8 | 9.2 |
| 24.2 | 26.0 |
| 24.9 | 71.1 |
| 25.4 | 17.0 |
| 26.9 | 15.4 |
| 27.2 | 10.0 |
| 27.6 | 22.8 |
| 28.0 | 13.4 |
| 28.3 | 15.6 |
| 29.1 | 22.1 |
| 29.6 | 20.9 |
| 29.9 | 13.6 |
| 30.4 | 8.7 |
| 30.8 | 7.9 |
| 31.4 | 19.5 |
| 32.1 | 13.2 |
| 32.3 | 13.2 |
| 32.6 | 16.4 |
| 32.9 | 14.1 |
| 33.5 | 14.1 |
| 34.1 | 18.0 |
| 34.4 | 25.0 |
| 35.4 | 10.5 |
| 35.8 | 18.6 |
| 36.2 | 12.2 |
| 36.8 | 21.2 |
| 37.3 | 9.4 |
| 37.8 | 26.0 |
| 38.2 | 18.0 |
| 38.7 | 10.5 |
| 39.3 | 12.2 |
| 39.6 | 17.8 |
| 39.9 | 12.2 |
| 40.9 | 12.0 |
| 41.1 | 14.6 |
| 41.7 | 15.4 |
| 42.8 | 12.9 |
| 43.3 | 14.4 |
| 43.9 | 11.3 |
| 44.6 | 12.7 |

TABLE 11

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with ethanol.

| Angle °2 Theta | Relative Intensity % |
|---|---|
| 2.8 | 0.2 |
| 8.2 | 25.7 |
| 9.3 | 31.9 |
| 10.9 | 100.0 |
| 11.3 | 6.3 |
| 12.8 | 29.9 |
| 13.0 | 15.4 |
| 13.4 | 49.7 |
| 13.7 | 14.3 |
| 14.6 | 51.8 |
| 14.9 | 32.7 |
| 15.4 | 84.1 |
| 16.3 | 18.6 |
| 16.5 | 63.8 |
| 18.0 | 42.9 |
| 18.4 | 81.5 |
| 19.2 | 41.0 |
| 19.4 | 48.7 |
| 19.8 | 18.3 |
| 21.8 | 59.8 |
| 22.2 | 41.5 |
| 22.8 | 19.3 |
| 23.5 | 4.7 |
| 24.4 | 21.5 |
| 25.1 | 69.6 |
| 25.6 | 28.3 |
| 26.6 | 9.3 |
| 27.2 | 20.5 |
| 27.6 | 29.5 |
| 28.2 | 17.7 |
| 28.5 | 23.6 |
| 29.2 | 19.0 |
| 29.5 | 25.4 |
| 30.0 | 25.4 |
| 31.5 | 15.9 |
| 32.0 | 14.3 |
| 32.6 | 21.5 |
| 32.9 | 19.6 |
| 33.7 | 20.9 |
| 34.1 | 11.7 |
| 34.5 | 21.2 |
| 35.0 | 19.9 |
| 36.0 | 26.5 |
| 36.7 | 12.9 |
| 37.3 | 11.7 |
| 37.9 | 32.3 |
| 38.7 | 16.8 |
| 39.7 | 17.4 |
| 40.0 | 13.5 |
| 40.3 | 13.7 |
| 40.8 | 15.7 |
| 41.5 | 16.8 |
| 42.1 | 14.3 |
| 42.7 | 12.4 |
| 43.6 | 20.9 |
| 44.3 | 12.9 |

TABLE 12

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with ethyl formate.

| Angle °2 Theta | Relative Intensity % |
|---|---|
| 3.5 | 0.0 |
| 5.0 | 0.1 |
| 8.0 | 11.9 |
| 9.4 | 20.0 |
| 10.9 | 65.3 |
| 11.9 | 2.5 |
| 12.4 | 35.3 |
| 13.1 | 33.1 |
| 13.9 | 35.7 |
| 14.4 | 19.4 |
| 14.9 | 23.9 |
| 15.6 | 100.0 |
| 16.7 | 54.5 |
| 17.4 | 60.8 |
| 17.9 | 80.6 |
| 18.2 | 8.6 |
| 18.8 | 24.2 |
| 19.2 | 45.0 |
| 19.6 | 34.2 |
| 20.0 | 12.4 |
| 21.5 | 41.6 |
| 21.8 | 69.0 |
| 22.1 | 18.6 |
| 22.6 | 8.6 |
| 23.1 | 11.9 |
| 23.4 | 12.6 |
| 23.8 | 12.8 |
| 24.5 | 36.5 |
| 25.0 | 42.5 |
| 25.2 | 40.4 |
| 25.6 | 38.0 |
| 26.0 | 8.8 |
| 26.3 | 23.6 |
| 27.0 | 20.9 |
| 27.3 | 11.9 |
| 28.0 | 22.7 |
| 28.3 | 21.2 |
| 28.9 | 21.2 |
| 29.9 | 20.6 |
| 30.1 | 12.6 |
| 30.4 | 13.5 |
| 30.8 | 16.7 |
| 31.1 | 24.2 |
| 31.6 | 9.8 |
| 32.6 | 19.7 |
| 33.3 | 16.5 |
| 33.6 | 15.7 |
| 34.3 | 11.3 |
| 34.9 | 17.5 |
| 35.7 | 31.6 |
| 36.6 | 11.0 |
| 37.3 | 34.9 |
| 37.7 | 11.7 |
| 38.4 | 17.5 |
| 39.0 | 14.2 |
| 39.5 | 18.3 |
| 39.9 | 13.0 |
| 40.6 | 10.8 |
| 40.9 | 14.9 |
| 41.7 | 11.3 |
| 42.4 | 14.9 |
| 42.9 | 9.2 |
| 43.7 | 14.5 |
| 44.3 | 10.6 |

TABLE 13

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with 1,4-dioxane.

| Angle °2 Theta | Relative Intensity % |
|---|---|
| 8.1 | 7.5 |
| 9.3 | 31.8 |
| 10.8 | 37.1 |
| 12.5 | 31.2 |
| 13.0 | 11.7 |
| 13.2 | 16.0 |
| 13.9 | 10.8 |
| 14.3 | 19.5 |
| 15.1 | 80.7 |
| 16.3 | 100.0 |
| 17.5 | 64.7 |
| 17.8 | 50.2 |
| 18.8 | 48.4 |
| 19.4 | 55.7 |
| 20.2 | 7.8 |
| 21.6 | 89.0 |
| 22.3 | 24.3 |
| 22.9 | 12.5 |
| 23.8 | 16.3 |
| 24.6 | 44.0 |
| 24.8 | 45.3 |
| 25.5 | 18.2 |
| 25.8 | 24.3 |
| 26.1 | 21.0 |
| 26.8 | 35.3 |
| 27.5 | 9.5 |
| 28.1 | 20.2 |
| 28.3 | 14.4 |
| 28.8 | 18.9 |
| 29.4 | 14.8 |
| 30.2 | 14.0 |
| 30.5 | 9.9 |
| 30.9 | 18.4 |
| 31.3 | 18.2 |
| 32.6 | 18.5 |
| 33.6 | 15.6 |
| 34.1 | 18.5 |

TABLE 14

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with dimethylsulfoxide.

| Angle °2 Theta | Relative Intensity % |
|---|---|
| 8.1 | 19.9 |
| 9.4 | 11.5 |
| 10.8 | 73.1 |
| 12.4 | 44.0 |
| 13.0 | 31.0 |
| 14.0 | 21.5 |
| 14.4 | 45.0 |
| 15.0 | 28.5 |
| 15.4 | 100.0 |
| 15.6 | 27.7 |
| 16.5 | 66.2 |
| 17.4 | 65.3 |
| 17.8 | 70.5 |
| 19.0 | 47.1 |
| 19.6 | 68.3 |
| 20.3 | 17.4 |
| 21.5 | 64.5 |
| 21.8 | 49.3 |
| 22.3 | 34.9 |
| 23.1 | 15.9 |
| 23.6 | 6.4 |

TABLE 14-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with dimethylsulfoxide.

| Angle °2 Theta | Relative Intensity % |
|---|---|
| 24.2 | 25.8 |
| 25.0 | 88.0 |
| 25.5 | 24.2 |
| 25.9 | 16.1 |
| 26.8 | 34.9 |
| 27.1 | 16.3 |
| 27.8 | 17.6 |
| 28.5 | 23.7 |
| 28.8 | 26.8 |
| 29.5 | 13.0 |
| 30.3 | 12.2 |
| 30.9 | 18.3 |
| 32.8 | 12.4 |
| 33.7 | 8.9 |

TABLE 15

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with N-methyl-2-pyrrolidinone.

| Angle °2 Theta | Relative Intensity % |
|---|---|
| 7.9 | 14.0 |
| 9.4 | 15.2 |
| 10.8 | 38.5 |
| 12.1 | 60.9 |
| 12.8 | 29.0 |
| 13.0 | 35.5 |
| 14.1 | 48.3 |
| 14.6 | 6.5 |
| 14.9 | 17.9 |
| 15.5 | 100.0 |
| 15.8 | 16.5 |
| 16.6 | 97.3 |
| 17.3 | 69.8 |
| 18.4 | 24.2 |
| 18.6 | 13.8 |
| 18.9 | 37.2 |
| 19.6 | 53.0 |
| 20.0 | 10.9 |
| 21.1 | 45.7 |
| 21.6 | 69.8 |
| 22.0 | 19.3 |
| 22.6 | 8.2 |
| 23.1 | 18.4 |
| 23.4 | 27.0 |
| 23.7 | 11.4 |
| 24.6 | 66.6 |
| 25.0 | 38.5 |
| 25.6 | 35.2 |
| 26.4 | 16.5 |
| 27.2 | 43.8 |
| 28.0 | 23.1 |
| 28.4 | 27.8 |
| 28.9 | 10.2 |
| 29.9 | 28.4 |
| 30.6 | 18.4 |
| 31.4 | 10.7 |
| 31.8 | 11.2 |
| 32.3 | 22.9 |
| 32.8 | 22.9 |
| 33.5 | 18.4 |
| 33.9 | 11.4 |

TABLE 15-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with N-methyl-2-pyrrolidinone.

| Angle °2 Theta | Relative Intensity % |
|---|---|
| 34.8 | 14.8 |
| 35.3 | 38.5 |
| 35.7 | 20.3 |
| 36.6 | 38.9 |
| 37.3 | 20.8 |
| 38.2 | 16.3 |
| 38.4 | 16.1 |
| 38.9 | 20.1 |
| 39.6 | 18.4 |
| 40.5 | 18.4 |
| 41.0 | 14.4 |
| 41.5 | 8.8 |
| 42.3 | 14.6 |
| 43.0 | 12.0 |
| 43.3 | 14.0 |
| 44.0 | 19.8 |

TABLE 16

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with dimethyl acetamide.

| Angle °2 Theta | Relative Intensity % |
|---|---|
| 5.2 | 0.1 |
| 8.0 | 24.9 |
| 9.4 | 19.6 |
| 10.8 | 59.0 |
| 12.1 | 88.2 |
| 12.8 | 30.7 |
| 13.0 | 35.2 |
| 13.9 | 36.5 |
| 14.1 | 53.4 |
| 14.9 | 22.3 |
| 15.4 | 97.4 |
| 15.6 | 12.9 |
| 16.5 | 92.2 |
| 17.0 | 100.0 |
| 17.4 | 83.8 |
| 18.4 | 25.4 |
| 18.7 | 22.6 |
| 18.9 | 35.9 |
| 19.5 | 47.1 |
| 20.0 | 11.9 |
| 21.2 | 65.2 |
| 21.6 | 52.3 |
| 22.0 | 22.3 |
| 22.3 | 8.7 |
| 23.0 | 18.0 |
| 23.1 | 18.3 |
| 23.7 | 9.9 |
| 24.2 | 18.3 |
| 24.6 | 72.2 |
| 24.9 | 41.1 |
| 25.4 | 21.6 |
| 25.7 | 26.7 |
| 26.4 | 18.0 |
| 27.0 | 46.7 |
| 27.2 | 28.1 |
| 27.6 | 7.4 |
| 28.1 | 16.9 |
| 28.8 | 13.1 |
| 29.2 | 6.0 |

TABLE 16-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with dimethyl acetamide.

| Angle °2 Theta | Relative Intensity % |
|---|---|
| 29.5 | 16.9 |
| 30.0 | 21.1 |
| 30.5 | 16.9 |
| 31.0 | 7.2 |
| 31.9 | 12.7 |
| 32.3 | 21.1 |
| 33.0 | 20.4 |
| 33.3 | 11.1 |
| 33.8 | 9.0 |
| 34.2 | 8.1 |
| 34.8 | 11.2 |
| 35.1 | 14.0 |
| 35.4 | 59.0 |
| 36.3 | 9.2 |
| 36.8 | 25.9 |
| 37.3 | 10.5 |
| 37.6 | 11.9 |
| 38.0 | 11.4 |
| 38.5 | 11.2 |
| 38.9 | 25.9 |
| 39.4 | 11.1 |
| 39.7 | 12.9 |
| 40.2 | 9.9 |
| 40.5 | 12.3 |
| 41.2 | 7.7 |
| 41.9 | 11.2 |
| 42.4 | 10.5 |
| 43.1 | 12.1 |
| 43.9 | 12.1 |
| 44.2 | 8.9 |
| 44.3 | 7.7 |

TABLE 17

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with water.

| Angle °2 Theta | Relative Intensity % |
|---|---|
| 6.4 | 5.2 |
| 6.9 | 7.8 |
| 8.8 | 34.6 |
| 9.6 | 23.8 |
| 11.0 | 5.4 |
| 11.4 | 9.2 |
| 12.2 | 86.1 |
| 12.6 | 54.8 |
| 13.3 | 78.1 |
| 13.8 | 25.4 |
| 14.2 | 27.9 |
| 14.8 | 27.0 |
| 15.3 | 55.4 |
| 15.5 | 71.2 |
| 16.0 | 46.2 |
| 17.2 | 34.6 |
| 17.7 | 14.1 |
| 18.1 | 65.3 |
| 18.4 | 100.0 |
| 19.2 | 47.3 |
| 19.5 | 75.3 |
| 20.2 | 53.6 |
| 20.5 | 61.5 |
| 21.3 | 69.9 |

TABLE 17-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with water.

| Angle °2 Theta | Relative Intensity % |
|---|---|
| 21.8 | 34.6 |
| 22.2 | 19.4 |
| 22.9 | 25.0 |
| 23.8 | 44.1 |
| 24.7 | 23.8 |
| 25.3 | 41.5 |
| 26.2 | 37.9 |
| 27.7 | 25.0 |
| 28.6 | 29.2 |
| 29.9 | 21.2 |
| 30.4 | 38.9 |
| 32.1 | 47.9 |
| 32.6 | 47.9 |
| 33.6 | 31.8 |
| 34.5 | 42.0 |

TABLE 18

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with cyclopentanone.

| Angle °2 Theta | Relative Intensity % |
|---|---|
| 2.3 | 0.1 |
| 3.3 | 0.1 |
| 6.3 | 0.1 |
| 8.1 | 11.5 |
| 9.4 | 14.6 |
| 10.9 | 35.7 |
| 12.4 | 38.1 |
| 13.1 | 28.1 |
| 14.0 | 20.5 |
| 14.3 | 27.4 |
| 15.0 | 19.6 |
| 15.5 | 100.0 |
| 16.6 | 50.1 |
| 17.4 | 66.5 |
| 17.8 | 54.0 |
| 18.8 | 32.2 |
| 19.1 | 36.5 |
| 19.6 | 46.9 |
| 20.1 | 9.1 |
| 21.5 | 38.1 |
| 21.7 | 46.4 |
| 22.3 | 18.2 |
| 23.1 | 19.6 |
| 23.7 | 8.5 |
| 24.3 | 26.0 |
| 24.9 | 72.6 |
| 25.4 | 31.4 |
| 26.2 | 16.2 |
| 26.9 | 30.7 |
| 27.2 | 25.7 |
| 27.9 | 26.7 |
| 28.3 | 21.1 |
| 28.8 | 19.9 |
| 29.6 | 21.8 |
| 30.2 | 13.1 |
| 30.9 | 24.7 |
| 31.5 | 15.9 |
| 32.0 | 16.8 |
| 32.6 | 12.9 |
| 33.4 | 21.4 |

TABLE 18-continued

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with cyclopentanone.

| Angle °2 Theta | Relative Intensity % |
|---|---|
| 33.6 | 15.9 |
| 34.0 | 12.4 |
| 34.4 | 10.4 |
| 34.8 | 14.1 |
| 35.1 | 14.9 |
| 35.7 | 39.0 |
| 36.6 | 18.2 |
| 37.3 | 32.5 |
| 38.0 | 15.9 |
| 38.3 | 15.2 |
| 39.0 | 15.7 |
| 39.6 | 24.0 |
| 40.3 | 11.3 |
| 41.0 | 16.8 |
| 41.7 | 15.4 |
| 42.1 | 14.1 |
| 42.7 | 10.6 |
| 43.3 | 12.9 |
| 43.7 | 10.8 |
| 44.2 | 16.2 |
| 44.7 | 11.9 |

TABLE 19

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with t-butylamine.

| Angle °2 Theta | Relative Intensity % |
|---|---|
| 8.1 | 20.6 |
| 9.0 | 49.0 |
| 10.5 | 65.1 |
| 12.5 | 32.1 |
| 13.0 | 45.3 |
| 13.6 | 7.7 |
| 14.2 | 35.6 |
| 14.7 | 90.9 |
| 15.9 | 100.0 |
| 17.6 | 53.3 |
| 18.0 | 60.8 |
| 18.5 | 66.2 |
| 18.9 | 78.6 |
| 19.7 | 11.1 |
| 21.2 | 44.4 |
| 21.5 | 29.5 |
| 22.0 | 36.8 |
| 23.3 | 6.9 |
| 24.1 | 47.6 |
| 24.6 | 15.0 |
| 25.2 | 20.0 |
| 26.2 | 16.5 |
| 26.8 | 12.2 |
| 27.2 | 13.9 |
| 28.0 | 17.1 |
| 28.7 | 22.7 |
| 29.0 | 12.7 |
| 29.6 | 19.1 |
| 30.3 | 13.4 |
| 31.0 | 5.8 |
| 32.2 | 12.7 |
| 32.6 | 8.6 |
| 33.2 | 15.5 |

TABLE 20

XRPD characteristic angles and relative intensities for 6α,9α-Difluoro-17α-[(2-furanylcarbonyl)oxy]-11β-hydroxy-16α-methyl-3-oxo-androsta-1,4-diene-17β-carbothioic acid S-fluoromethyl ester, complex with ε-caprolactam.

| Angle 2 Theta° | Relative Intensity % |
|---|---|
| 7.8 | 32.8 |
| 9.0 | 19.2 |
| 10.5 | 37.5 |
| 12.0 | 71.5 |
| 12.6 | 37.1 |
| 13.3 | 8.6 |
| 13.9 | 47.8 |
| 14.4 | 33.3 |
| 15.1 | 100.0 |
| 16.1 | 47.8 |
| 16.9 | 96.1 |
| 17.4 | 82.6 |
| 18.3 | 51.7 |
| 18.6 | 87.8 |
| 18.9 | 81.9 |
| 21.1 | 48.4 |
| 21.4 | 41.0 |
| 21.9 | 20.7 |
| 22.3 | 28.9 |
| 22.7 | 23.6 |
| 23.8 | 40.0 |
| 24.2 | 60.0 |
| 24.5 | 70.2 |
| 25.5 | 17.9 |
| 26.3 | 36.6 |
| 27.3 | 39.0 |
| 28.1 | 34.7 |
| 29.0 | 45.7 |
| 29.5 | 24.4 |
| 30.0 | 27.2 |
| 30.8 | 31.1 |
| 32.3 | 35.2 |
| 33.9 | 37.5 |
| 34.7 | 46.8 |

TABLE 21

Raman band positions for various complexes with 6α,9α-Difluoro-17α-[(2-furanylcarbonyl)oxy]-11β-hydroxy-16α-methyl-3-oxo-androsta-1,4-diene-17β-carbothioic acid S-fluoromethyl ester

| Guest molecule | Band positions (cm$^{-1}$) |
|---|---|
| Butan-1-ol | 3114, 3056, 2937, 2881, 1727, 1661, 1606, 1470, 1394, 1341, 1312, 1235, 1198, 1151, 1128, 1076, 997, 930, 883, 850, 817, 733, 702, 623, 597, 568, 548, 527, 414, 391, 373, 290, 245, 197, 176, 97 |
| Methyl acetate | 3146, 3047, 2967, 2942, 2882, 1730, 1669, 1636, 1611, 1569, 1471, 1393, 1340, 1309, 1235, 1200, 1151, 1112, 1075, 998, 934, 882, 858, 733, 700, 648, 596, 569, 547, 528, 413, 393, 375, 286, 237, 196, 175, 92 |
| Acetic acid | 3148, 3043, 2977, 2933, 2880, 1731, 1662, 1616, 1600, 1471, 1393, 1343, 1313, 1247, 1199, 1154, 1124, 1076, 998, 974, 931, 881, 734, 701, 598, 570, 554, 529, 415, 374, 286, 240, 184, 87 |
| Propan-1-ol | 3057, 2937, 2881, 1726, 1662, 1608, 1470, 1394, 1341, 1311, 1235, 1199, 1151, 1127, 1076, 997, 930, 883, 851, 733, 702, 622, 597, 567, 547, 528, 461, 414, 392, 374, 290, 244, 196, 176, 94 |
| Ethanol | 3058, 2944, 2881, 1726, 1662, 1620, 1608, 1470, 1393, 1341, 1310, 1235, 1199, 1151, 1125, 1076, 997, 930, 883, 732, 701, 597, 167, 547, 528, 415, 393, 375, 289, 245, 196, 176, 89 |
| Ethyl formate | 3113, 3046, 2975, 2946, 2881, 1729, 1696, 1667, 1394, 1342, 1311, 1236, 1199, 1153, 1124, 1075, 998, 937, 883, 730, 701, 597, 569, 550, 527, 413, 391, 287, 243, 195, |

TABLE 21-continued

Raman band positions for various complexes with 6α,9α-Difluoro-17α-[(2-furanylcarbonyl)oxy]-11β-hydroxy-16α-methyl-3-oxo-androsta-1,4-diene-17β-carbothioic acid S-fluoromethyl ester

| Guest molecule | Band positions (cm$^{-1}$) |
|---|---|
| | 176, 88 |
| 1,4-dioxane | 3149, 3046, 2974, 2936, 2883, 1726, 1669, 1635, 1611, 1568, 1471, 1392, 1342, 1308, 1236, 1200, 1152, 1127, 1075, 1015, 998, 932, 883, 835, 732, 700, 597, 568, 548, 528, 414, 392, 375, 286, 239, 195, 184, 172, 86 |
| Dimethyl-sulphoxide | 3146, 3045, 2983, 2943, 2916, 2878, 1723, 1666, 1633, 1608, 1569, 1470, 1416, 1394, 1342, 1310, 1236, 1199, 1152, 1125, 1075, 1040, 998, 972, 931, 882, 731, 701, 673, 597, 567, 549, 527, 414, 305, 286, 243, 196, 183, 87 |

The invention claimed is:

1. A crystalline complex comprising a compound of formula (I)

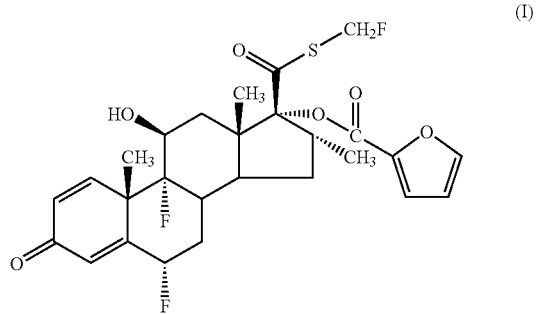

in which the crystal lattice is stabilised by the presence of a guest molecule, characterised in that the crystalline complex is of space group $P2_12_12_1$ having unit cell dimensions of about 12.5±1.0 Å, 15±1.0 Å, and 16.2±1.0 Å when determined at either 120K or 150K, wherein the guest molecule comprises one or more of t-butylamine, cyclohexanone, pyridine, butylamine, cyclohexylamine, or ε-caprolactam.

2. A complex according to claim 1 wherein the guest molecule is liquid at ambient temperature and pressure.

3. A complex according to claim 1 wherein the guest molecule is ε-caprolactam.

4. A complex according to claim 1 wherein the guest molecule is selected from the group consisting of t-butylamine and cyclohexylamine.

5. A complex according to claim 1 wherein the guest molecule is cyclohexanone.

6. A complex according to claim 1 wherein the guest molecule is pyridine.

7. A complex according to claim 1 wherein the guest molecule is t-butylamine.

8. A complex according to claim 1 wherein the guest molecule is cyclohexylamine.

9. A complex according to claim 1 wherein the molar ratio of compound of formula (I) to guest molecule is 1:2.0 to 1:0.3.

10. A pharmaceutical composition comprising a complex according to claim 1 together with a physiologically acceptable diluent or carrier.

* * * * *